United States Patent [19]

Butterfield et al.

[11] Patent Number: 5,273,046
[45] Date of Patent: Dec. 28, 1993

[54] METHOD OF DETERMINING OPTIMUM ARTERY APPLANATION

[75] Inventors: Robert D. Butterfield, Poway; Stephen A. Martin, Carlsbad, both of Calif.

[73] Assignee: IVAC Corporation, San Diego, Calif.

[21] Appl. No.: 869,553

[22] Filed: Apr. 15, 1992

[51] Int. Cl.$^5$ .............................................. A61B 5/02
[52] U.S. Cl. ................................... 128/672; 128/690; 128/687
[58] Field of Search ............... 128/672, 677–687, 128/690; 364/413.03

[56] References Cited

U.S. PATENT DOCUMENTS

| | | |
|---|---|---|
| 4,269,193 | 5/1981 | Eckerle . |
| 4,423,738 | 1/1984 | Newgard . |
| 4,799,491 | 1/1989 | Eckerle . |
| 4,802,488 | 2/1989 | Eckerle . |
| 4,836,213 | 6/1989 | Wenzel . |
| 4,893,631 | 1/1990 | Wenzel et al. . |
| 5,119,822 | 6/1992 | Niwa ................................. 128/690 |
| 5,183,050 | 2/1993 | Kawamura et al. ................ 128/690 |

OTHER PUBLICATIONS

U.S. Ser. No. 07/500,063 Mar. 27, 1990 Drzewiecki et al.
U.S. Ser. No. 07/621,165 Nov. 30, 1990 Butterfield, et al.

Primary Examiner—Lee S. Cohen
Assistant Examiner—Robert L. Nasser, Jr.
Attorney, Agent, or Firm—Dykema Gossett

[57] ABSTRACT

A method, for use in a non-invasive blood pressure monitoring system, of determining optimum artery applanation. The system uses a stress sensor including a stress sensitive element for detecting stress of tissue overlying an artery of interest. The tissue stress sensor is placed in communication with tissue overlying the artery of interest and at least one electrical signal is obtained therefrom representing stress data across the length of the stress sensitive element. The data represents stress datum communicated to a preselected portion of the stress sensitive element. From the stress datum, various algorithms are used, singly or in combination, to provide the best measure of optimum applanation state. Intra-arterial blood pressure is then calculated using datum collected at the optimum applanation state. In addition, to the optimum applanation methods, a method is disclosed for determining which portion of the stress sensitive element is best suited for estimating intra-arterial blood pressure.

59 Claims, 30 Drawing Sheets

METHOD OF DETERMINING OPTIMUM ARTERY APPLANATION

TECHNICAL FIELD

The present invention generally relates to pressure measurement systems, and more particularly relates to a method for non-invasively determining the intra-arterial blood pressure of a wearer.

BACKGROUND OF THE INVENTION

Systems for measuring the intra-arterial blood pressure of a patient can be subdivided into two main groups—those which invade the arterial wall to access blood pressure and those which use non-invasive techniques. Traditionally, the most accurate blood pressure measurements were achievable only by using invasive methods. One common invasive method involves inserting a fluid filled catheter into the patient's artery.

While invasive methods provide accurate blood pressure measurements, the associated risk of infection and potential for complications, in many cases, outweigh the advantages in using invasive methods. Because of these risks associated with invasive methods, a non-invasive method, known as the Korotkoff method is widely used.

The Korotkoff method is known as an auscultatory method because it uses the characteristic sound made as the blood flows through the artery to mark the points of highest (systolic) and lowest (diastolic) blood pressure. Although the Korotkoff method is non-invasive, it only provides a measurement of the highest pressure point and the lowest pressure point along the continuous pressure wave. While systolic and diastolic pressure are sufficient for accurate diagnosis in many instances, there are many applications in which it is desirable to monitor and utilize the entire characteristic curve of the blood pressure wave. In these applications, the Korotkoff method is simply incapable of providing ample information. In addition to this limitation of the Korotkoff method, it necessitates the temporary occlusion (complete closing) of the artery in which blood pressure is being monitored. While arterial occlusion is not prohibitive in many applications, there are occasions where the patient's blood pressure must be monitored continuously (such as when undergoing surgery) and accordingly, the prohibiting of blood flow, even on a temporary basis, is undesirable.

Because of the above-mentioned risks involved with invasive blood pressure measurement, and the shortcomings of the Korotkoff method, extensive investigation has been conducted in the area of continuous, non-invasive blood pressure monitoring and recording. Some of these non-invasive techniques make use of tonometric principles which take advantage of the fact that as blood pressure flows through the arterial vessel, forces are transmitted through the artery wall and through the surrounding arterial tissue and are accessible for monitoring at the surface of the tissue. Because the tonometric method of measuring blood pressure is non-invasive, it is used without the risks associated with invasive techniques. Furthermore, in addition to being more accurate than the Korotkoff method discussed above, it has the capability of reproducing the entire blood pressure wave form, as opposed to only the limited systolic and diastolic pressure points provided by the Korotkoff method.

Because the accuracy of tonometric measurements depend heavily upon the method and apparatus used to sense tissue forces, several sensors have been specifically developed for this purpose. For example, U.S. Pat. No. 4,423,738 issued to Newgard on Jan. 3, 1984 discloses an electromechanical force sensor which is made up of an array of individual force sensing elements, each of which has at least one dimensions smaller than the lumen of the underlying artery wherein blood pressure is to be measured. Also, U.S. Pat. No. 4,802,488 issued to Eckerle on Feb. 7, 1989, discloses an electromechanical transducer that includes an array of transducer elements. The transducer elements extend across an artery with transducer elements at the ends of the array extending beyond opposite edges of the artery. Additionally, U.S. patent application Ser. No. 07/500,063 and U.S. patent application Ser. No. 07/621,165 both disclose tonometric sensors for use in determining intra-arterial blood pressure. Each of the above four mentioned patents/patent applications disclose transducers having sensing portions that span well beyond the lumen (opening) of the underlying artery. One main reason it is advantageous to construct a sensor in this manner is because the arteries of interest are relatively small and difficult to locate. By constructing tonometric sensors which employ a relatively long sensing area, the placement of the sensor by a technician, is not as critical as it would be if the sensor was capable of only sensing along a narrow region.

Although by constructing a tonometric sensor with a long sensing portion, the technician's task is simplified, it introduces certain complexities into the methodology used for determining intra-arterial blood pressure. For example, because the sensor face is made relatively long as compared to the lumen of the underlying artery, only a small fraction of the sensing portion of the tissue stress sensor is overlying the artery, and it is only this portion which is sensing useful forces (i.e. forces which are related to intra-arterial blood pressure). The remaining portion of the sensing portion is in contact with tissue which does not overlie the artery of interest, and accordingly, does not transmit forces to the sensing portion which can be used for determining intra-arterial pressure.

Therefore, in view of the above complexities, when employing tonometric sensors of the type discussed above, before the accurate intra-arterial blood pressure can be determined, a method must be employed for determining which portion of the sensor is best positioned over the artery of interest for determining the intra-arterial blood pressure. One such method is disclosed in U.S. Pat. No. 4,269,193 issued to Eckerle on May 26, 1981. The method disclosed in the '193 patent includes selecting the transducer element which has a maximum pulse amplitude output and then looking to its neighbors and choosing the neighbor having a spatially local minimum of at least one of the diastolic and systolic pressures. Other methods are disclosed in U.S. Pat. No. 4,802,488 issued to Eckerle on Feb. 7, 1989. In the '488 patent the following methods are disclosed, a curve-fit method, a two-humps method, a center-of-gravity method, and a "catch-all" method which includes using one of the three aforementioned methods in conjunction with externally supplied user information (such as sex, height, age, etc.). Also, in U.S. Pat. No. 4,893,631 issued to Wenzel, et al. on Jan. 16, 1990, discloses a method for determining which sensor in an array of sensors best tracks the pulse in an underlying artery using a spatially weighted averaging method. This method employs the steps of finding local diastolic pressure minimums, selecting the number of transducers spanning the local minimums, computing the spatially weighted average from elements centered about the local minimums and computing a weighted average therefrom.

In addition to the sensors function to measure tissue stress, the sensor also functions to applanate (or flatten) the artery of interest. Applanating the artery of interest is critical in correctly determining intra-arterial blood pressure. In fact, it has been found, that when the artery of interest is applanated to an optimum state, extremely accurate determinations of intra-arterial blood pressure can be made. U.S. Pat. No. 4,799,491 issued to Eckerle on Jan. 24, 1989 discloses a method for determining a "correct" hold down pressure. Additionally, U.S. Pat. No. 4,836,213 issued to Wenzel on Jun. 6, 1989 discloses a method for computing optimum hold down pressure for a transducer indicative of blood pressure in an artery.

Although the above-referenced methods may yield some degree of success, the Applicants of the present invention believe that a method which is superior to those heretofore disclosed methods employs the use of stress energy. For example, it is believed, that the best area of the sensor for collecting stress data for determining optimum applanation is that portion which receives the greatest contact stress energy from the tissue overlying the artery of interest.

Many methodologies are disclosed herein which utilize the above-referenced energy transfer theory. Other methodologies disclosed herein do not use the above-referenced energy transfer methodology but utilize techniques which provide superior results to those achievable using the methodologies taught in the above-referenced '491 and '213 patents.

Thus, it is an object of this invention to provide a method or methods of determining the applanation state of an artery of interest which is optimum for determining intra-arterial blood pressure using tonometric techniques.

A number of methodologies are disclosed for achieving this object. Some of the disclosed methodologies include collecting tissue stress information from the area of the stress sensor which receives the greatest contact stress energy from the tissue overlying the artery of interest. This information as used, in conjunction with other information, to determine the optimum applanation state of the artery.

SUMMARY OF THE INVENTION

In light of the foregoing objects, the present invention provides a method of estimating optimum arterial compression by measuring the stress of tissue overlying an artery of interest. The disclosed method is for use in a non-invasive blood pressure monitoring systems of the type including a tissue stress sensor having a stress sensitive element, the stress sensitive element having a length that exceeds the lumen of the artery of interest. The method includes the steps of placing the stress sensitive element of the tissue stress sensor in communication with the tissue overlying the artery of interest; orienting the stress sensitive element such that the length spans beyond the lumen of the artery of interest; using the stress sensitive element to varyingly compress the artery of interest thereby applanating the artery of interest through a plurality of stages, and at each said applanation stage; obtaining from the tissue stress sensor at least one electrical signal representing stress data across the length of the stress sensitive element, the stress data including a plurality of stress datum, each stress datum representing stress communicated to a predetermined portion of the stress sensitive element from the tissue overlying the artery of interest, each predetermined portion of the stress sensitive element lying along the length of the stress sensitive element, and for each applanation stage; selecting and computing an applanation optimization parameter, wherein the applanation optimization parameter is selected from the group comprising pulse parameter, mean distribution breadth parameter, pulse spread parameter, spatially averaged stress parameter, stress spatial curvature parameter, and stress variation parameter and an applanation state parameter; relating the selected applanation optimization parameter to the applanation state parameter; determining a value associated with a characteristic feature of the selected applanation optimization parameter with respect to the artery applanation state parameter, the characteristic feature being indicative of the optimum arterial compression; and estimating the optimum arterial compression to be that degree of artery applanation which produces the applanation optimization parameter value.

In an alternative embodiment one or more applanation optimization parameters can be used and the results thereof can be averaged together to form an overall composite indicator. Individual weighting functions may be applied to the individual applanation optimization parameters so as to weigh the significance of individual factors.

The present invention discloses 12 separate methods for determining when the optimum applanation state is achieved. Each of these methods employ one or more applanation optimization parameters as a function of an applanation state parameter and combine the two parameters in a unique way to provide a method for determining an optimum applanation state.

Still in another aspect, the present invention discloses a method for use in a non-invasive blood pressure monitoring system of the type including a tissue stress sensor having a stress sensitive element, the stress sensitive element having a length that exceeds the lumen of the artery of interest. Specifically, a method is provided of determining which portion of the stress sensitive element is best suited for estimating intra-arterial blood pressure. The method includes the steps of: placing the stress sensitive element of the tissue stress sensor in communication with the tissue overlying the artery of interest; orienting the stress sensitive element such that the length spans beyond the lumen of the artery of interest; using the stress sensitive element to compress the artery of interest thereby applanating the artery of interest; obtaining from the tissue stress sensor at least one electrical signal representing stress data across the length of the stress sensitive element, the stress data including a plurality of stress datum, each stress datum representing stress communicated to a predetermined portion of the stress sensitive element from the tissue overlying the artery of interest, each predetermined portion of the stress sensitive element lying along the length of the stress sensitive element; using the stress datum to define a pulsatily energetic region along the stress sensitive element; and estimating the value of the intra-arterial blood pressure to be the value of the contact stress data found in the pulsatily energetic region of the stress sensitive element.

DETAILED DESCRIPTION OF THE PREFERRED EMBODIMENTS

Figure 1:
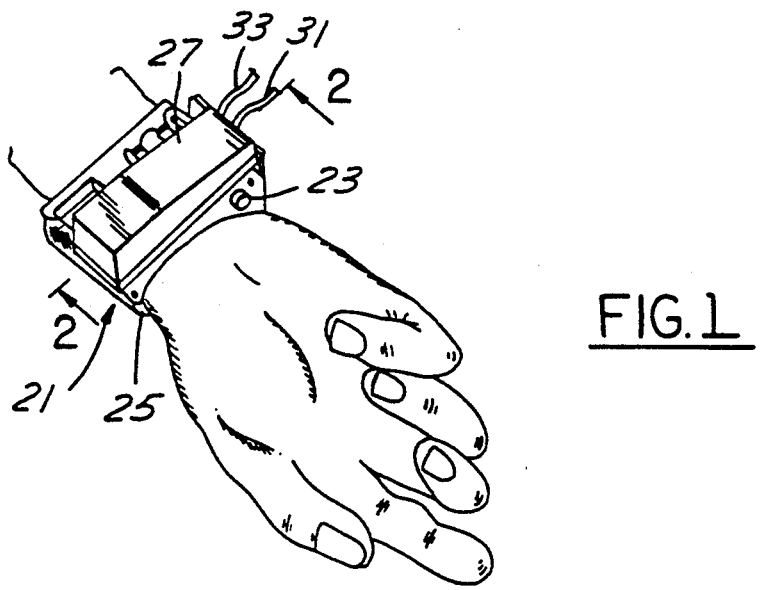
FIG. 1 is a perspective view of a tissue stress sensor attached to the wrist of a wearer.

Now referring to FIG. 1, wrist mount apparatus 21 includes base 23 and flexible strap 25. Flexible strap 25 is adapted to engage base 23 to the wrist of a user. Tissue stress sensor housing 27 is fastened to base 23 and houses a tissue stress sensitive element 34 (tissue stress sensitive element not shown) and a means 29 for moving the tissue stress sensitive element 20 (see FIG. 2) into operative engagement with the tissue overlying an artery of interest. Various electrical signals are derived from the tissue stress sensor located within sensor housing 27 and are made available therefrom via conductors within cable 31. These electrical signals carry data which will be used to derive the intra-arterial blood pressure of the wearer of apparatus 21.

Figure 2:
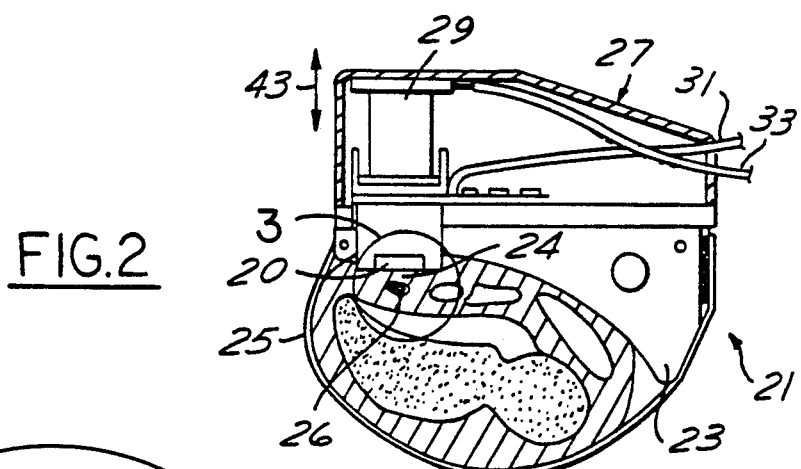
FIG. 2 is a cross-sectional view taken substantially along lines 2—2 of FIG. 1.

Now referring to FIG. 2, sensor housing 27 is mounted to base 23. Within sensor housing 27 is mounted a fluid operated slave bellows 29. Bellows 29 is attached to, at one of its end, tissue stress sensor 20. As bellows 29 receives a displacement fluid from a source of fluid via tubing 33, it expands downwardly 43 thereby causing tissue stress transducer 20 to engage tissue 24 overlying artery of interest 26.

Figure 3:
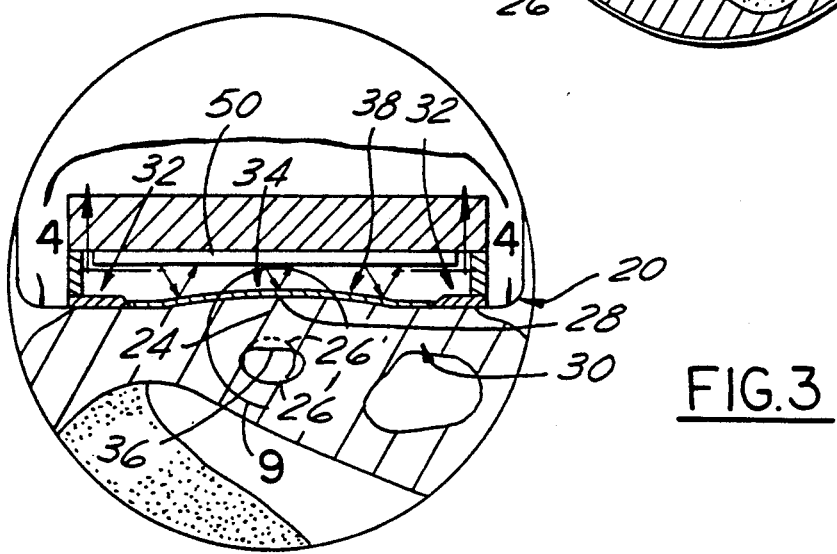
FIG. 3 is an enlarged view of encircled portion 3 of FIG. 2.

Now referring to FIG. 3, tissue stress sensor 20 includes wafer 30 which has a nonresponsive portion 32 and a responsive portion (also denoted as a stress sensitive element or also a diaphragm portion) 34. Nonresponsive portion 32 serves mainly to support responsive portion 34. Under conditions when tissue stress sensor 20 is not being applied against tissue 24, radial artery 26' has a generally rounded opening (or lumen) as depicted at 26'. As wafer 30 of tissue stress transducer 20 is pressed upon tissue 24, radial artery 26' begins to flatten (or applanate) along its top surface 36, thereby causing responsive portion 34 of wafer 30 to deflect slightly inward 38. As the blood pressure within radial artery 26 changes (i.e. pulsates), stress is created in tissue 24 which disturbs the equilibrium between responsive portion 34 of wafer 30 and top surface 28 of tissue 24. This disturbance in equilibrium causes movement between diagram 34 of wafer 30 and top surface 28 of overlying tissue 24. Such movement exists until a new equilibrium is established. The ability of diaphragm 34 to move and assume a unique displacement position for a given blood pressure within radial artery 26 forms the fundamental mechanism whereby tissue stress transducer 20 is capable of sensing the intra-arterial pressure of radial artery 26.

Figure 4A:
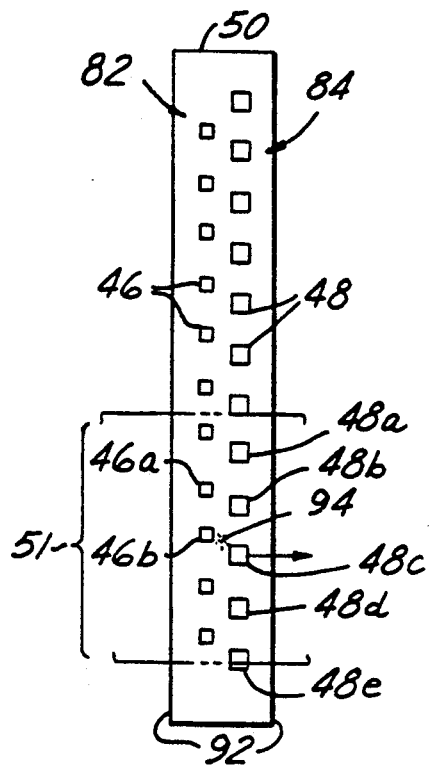
FIGS. 4a and 4b are diagrammatic views of the emitter and detector portions of the semiconductor assembly taken substantially along lines 4—4 of FIG. 3.
Figure 4B:
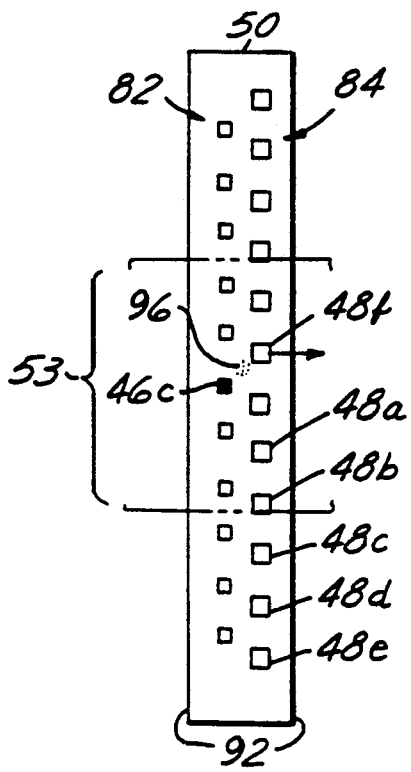

Now referring to FIGS. 4A and 4B, diode array 82 is arranged such that each diode 46 in the array of diodes 82 is generally arranged in a straight row substantially parallel to a long side 92 of electronic substrate 50. Likewise, each receiver 48 in the array of receivers 84 is generally arranged in a straight row which is substantially parallel to a long side 92 of electronic substrate 50. Row of diodes 46 is spaced apart from the row of receivers 48 and each diode 46 is juxtaposed with two receivers 48 such that it lies generally equidistant from its two closest receivers 48. This generally equidistant (or offset) relationship is demonstrated in FIG. 4A by virtue of emitter 46a being generally equidistant from its two closest detector neighbors 48a, 48b. Although this equidistant relationship has some advantages, it is believed that other arrangements between emitters and detectors may also work effectively.

Figure 5:
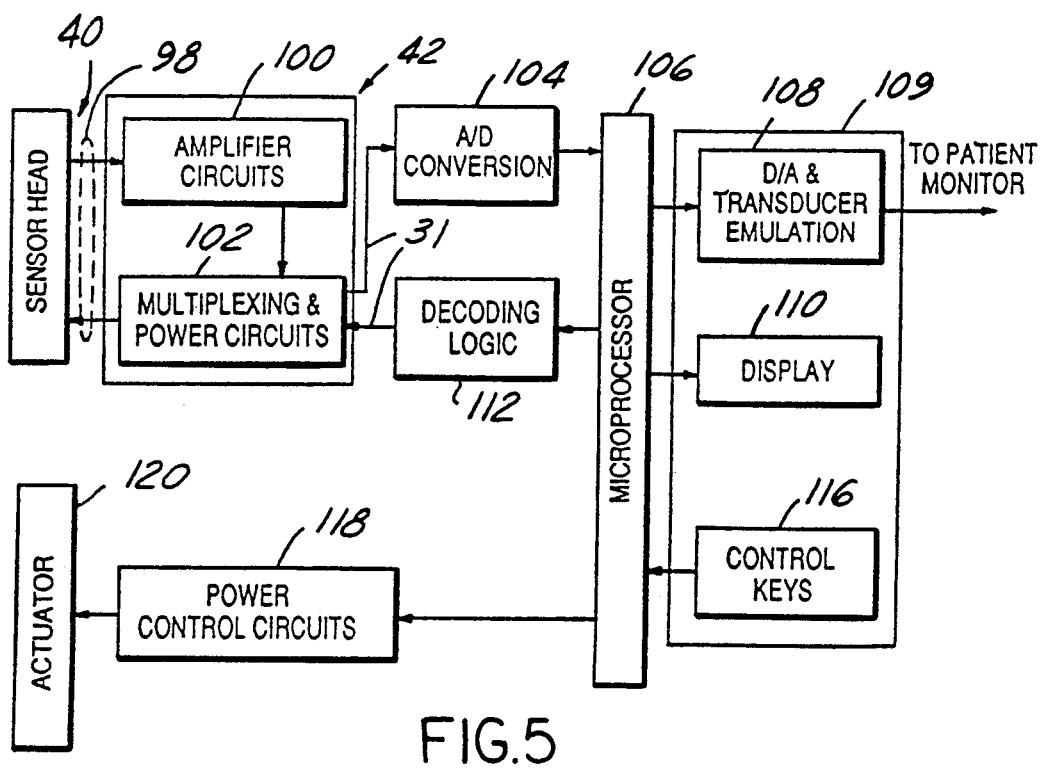
FIG. 5 is an electronic block diagram of the tissue contact stress sensor and associated supporting electronics of the present invention.

Now referring to FIG. 5, sensor head 40 is electronically coupled via multiple communication lines 98 to sensor base portion 42. Sensor base portion 42 provides conversion circuitry 100 to convert the current output signals from the array of detectors 84 to voltage output signals. These voltage signals are sent through multiplexer 102 where they are selectively digitized by A/D converter 104 and passed along to microprocessor 106. Microprocessor 106 performs the error correction spoken of earlier in the application and can also perform various other data compilation/analysis tasks. The blood pressure data can then be sent to any number of outputs such as a digital to analog converter 108 in cases where an analog representation of blood pressure is desirable. Blood pressure data may also be sent to display device 110 where it can provide the user with a continuously updated digital readout of blood pressure. Microprocessor 106 can be programmed to control decoding logic circuitry 112 which in turn activates select power circuits within multiplexing and power circuits 102.

The user of the system of the present invention can be given certain control options which can be input to microprocessor 106 via control keys 116. Power control circuit 118 can be used to interface microprocessor 106 to any number of mechanical actuators 120 which may be used to respond to various commands from microprocessor 106 in the utilization of sensor 40. For example, a routine may be used by microprocessor 106 which periodically queries whether sensor head 40 is properly applanating the artery of interest. If it is determined that the artery of interest is not properly applanated by wafer 30, microprocessor 106 may activate power control circuit 118 to command actuator 120 to move sensor 20 such that it properly applanates the artery of interest. Other applications may be devised where it is desirable to move, or otherwise control sensor head 20.

Figure 6:
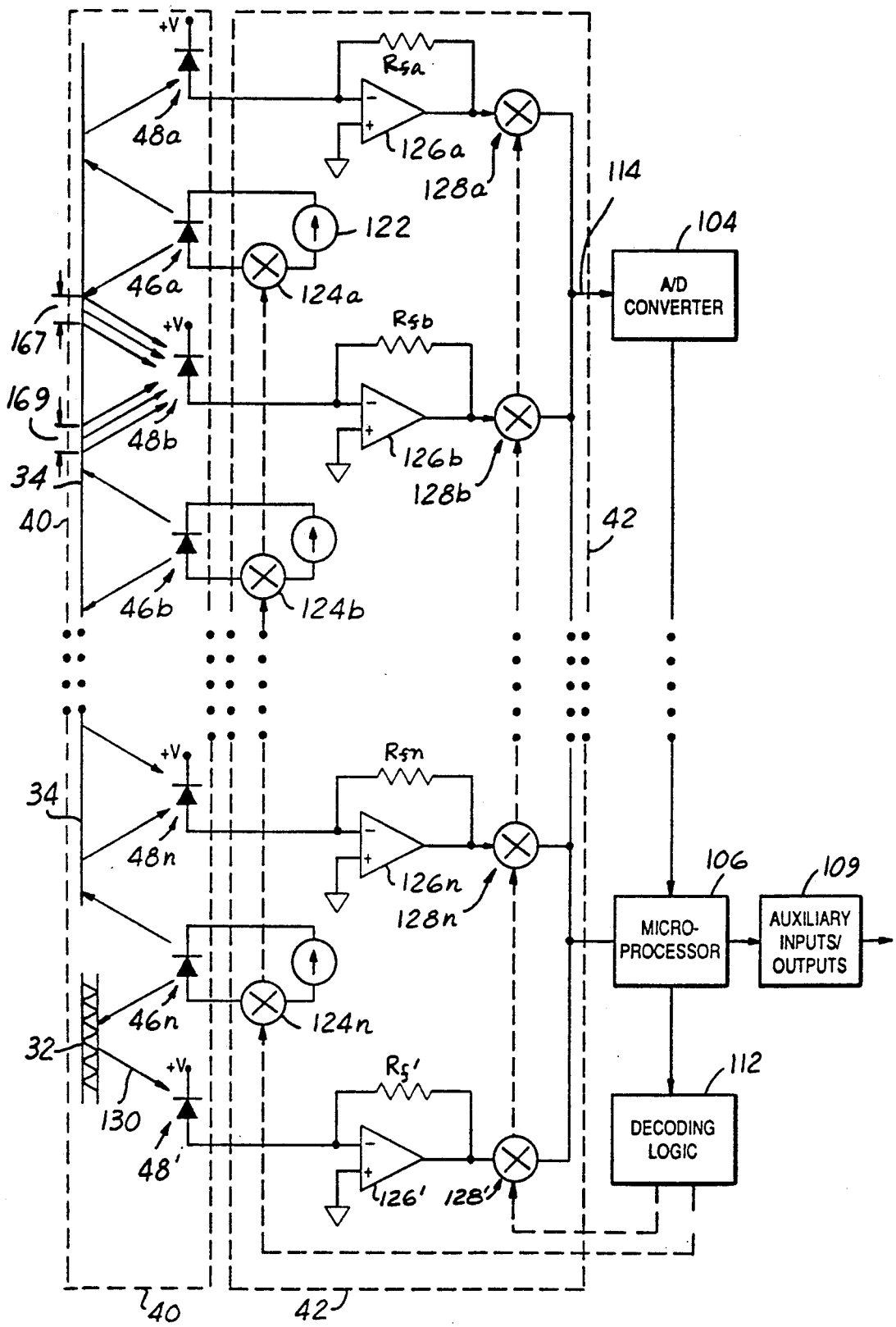
FIG. 6 is a detailed schematic of blocks 40 and 42 of FIG. 5.

Now referring to FIG. 6, sensor head 40 is comprised of a continuous reponsive diaphragm portion 34 which reflects light from diodes 46(a-n) and onto receivers 48(a-n). Each diode 46 is fed by current source typified at 122 which can be selectively switched on and off via a respective switch 124(a-n). These switches 124a through 124n are all individually controlled via decoding logic circuit 112. This is the fundamental mechanism whereby each diode 46a through 46n can be selectively activated to determine what portion of diaphragm 34 is best suited to be used to transduce the tissue stress signal. Each receiver 48a through 48n receives a portion of the light reflected from diaphragm 34 and converts this reflected light into an electrical current signal which is converted to a voltage by each receiver's respective converter 126a through 126n. Converters 126a through 126n are configured as current to voltage converters which effect a linear current-to-voltage conversion of the current signal derived from the respective receiver. Current-to-voltage converter circuits are well known to those skilled in the art and, accordingly, will not be discussed in detail here. The output of each converter is made available to its respective switch 128a through 128n. Switches 128a through 128n are controlled via decoding logic 112 which enables microprocessor 106 to select any output from converter 126a through 126n and place it on cable 31 where it is digitized by A/D converter 104.

One detector 48' is adapted to receive light 130 which is reflected from nonresponsive portion 32 of wafer 30. Detector 48' is used to generate a reference signal which will be used by microprocessor 106 to compensate for offset and gain errors due to temperature, aging and other environmental factors.

Figure 7:
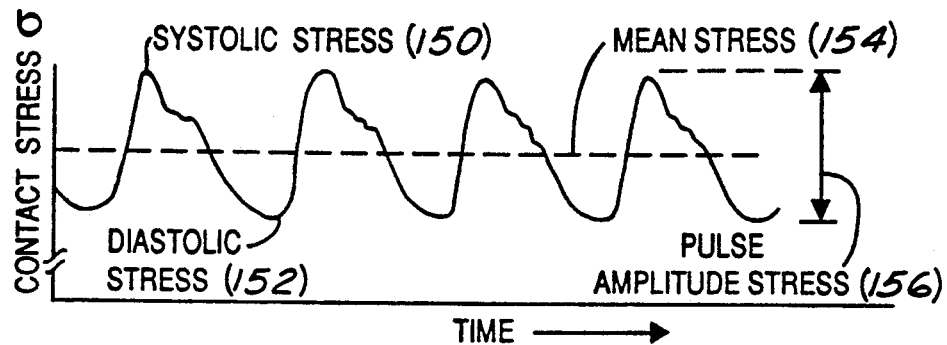
FIG. 7 is a graphic representation of a typical blood pressure waveform.
Figure 8:
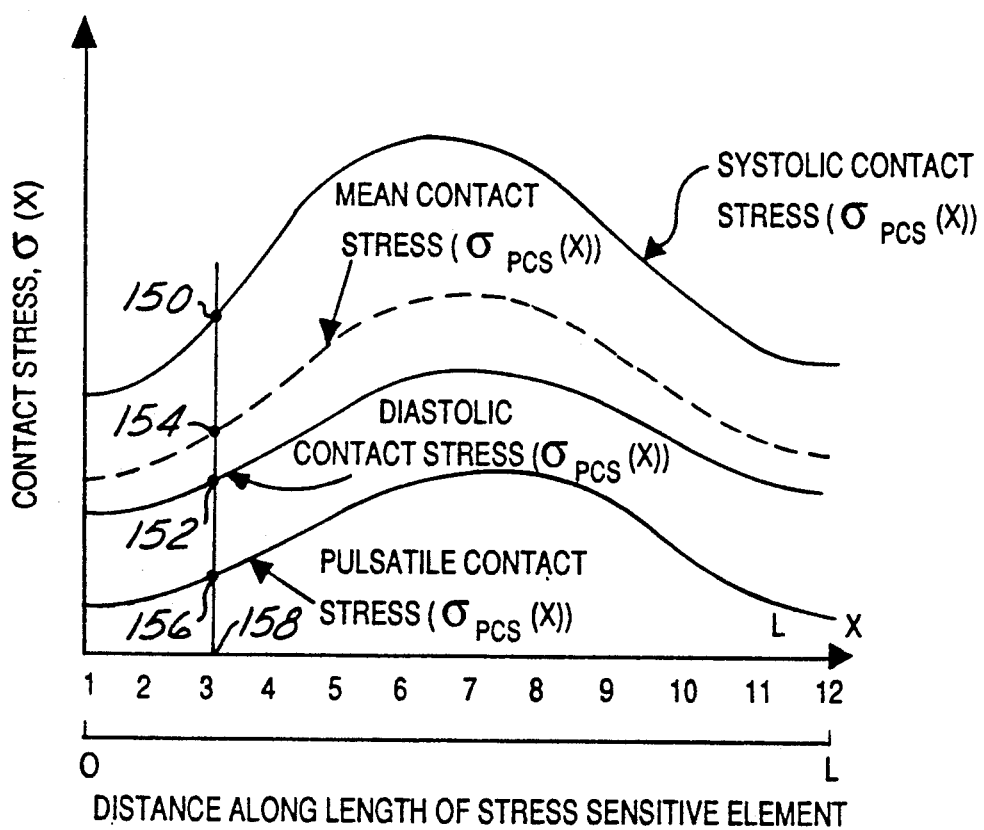
FIG. 8 is a graphical representation of contact stress versus distance along the length of the stress sensitive element.

Now referring to FIGS. 3, 4A and 4B, 6 and 7, when responsive portion 34 of wafer 30 (responsive portion 34 also known as tissue stress sensitive element or diaphragm) is placed against tissue 24, such that the artery of interest (outlined at 51 of FIG. 4A) is spanned by receivers 48a–48e, each receiver 48a–48e will generate a contact stress signal having the characteristic waveform shown in FIG. 7. Receivers which are close to center 94 of artery 51 will generate a characteristic waveform of greater magnitude than those at the peripheral edges of artery 51. The characteristic contour of the contact stress waveform generated by any one of the receivers 48a–48e will exhibit the following characteristics: a point of maximum (or systolic stress) 150 which corresponds to a peak or systolic blood pressure within artery 26, and a point of minimum (diastolic) stress 152 which corresponds to the diastolic blood pressure within artery 26. Mean stress 154 and pulse amplitude stress 156 are mathematically computed based on the following formula:

$$\sigma_{mean} = \frac{\int_{t_1}^{t_1 + \tau} \sigma(t) \cdot dt}{\int_{t_1}^{t_1 + \tau} dt},$$

where $\tau$ = one heartbeat $\sigma_{pulse\ amplitude} = \sigma_{systolic} - \sigma_{diastolic}$ Now referring to FIGS. 7 and 8, although contact stress can be plotted as a function of time (as depicted in FIG. 7), it can also be plotted as a function of distance along the length of the stress sensitive element 34 (as shown in FIG. 8). For example, if the characteristic contact stress curve of FIG. 7 represented the stress sensed at location 3 (referenced at 158 in FIG. 8), the characteristic points of systolic stress 150, diastolic stress 152, mean stress 154, and pulse amplitude stress 156 of FIG. 7 would correspond to the similarly marked points in FIG. 8. If the characteristic stress points from all of the locations 1–12 along stress sensitive element 34 are plotted, a contact stress curve resembling that of FIG. 8 would result. The stress information present in FIG. 8 is used in conjunction with the methodologies set forth hereinafter to determine optimum arterial applanation.

Theory of Blood Pressure Tonometry

As was described in conjunction with FIG. 3, a typical tonometric technique for monitoring blood pressure involves positioning a transducer over artery of interest 26 wherein the transducer is pressed against tissue overlying the artery so as to flatten (or applanate) the top surface 36 of artery 26. The transducer may comprise a stress sensitive element 34 which, in turn, may be comprised of a plurality of individual stress sensitive elements or a single, continuous stress sensitive element which is capable of sensing stress along overlapping portions of its length. The stress sensitive element is designed such that it is able to detect (and distinguish between) stresses created along its length. The portion of the stress sensitive element which is typically selected for monitoring blood pressure is that portion which is centered over the artery inasmuch as this portion provides an accurate measure of intra-arterial blood pressure. The portions of the stress sensitive elements which do not directly overlie the artery of interest do not provide as accurate a measure of intra-arterial blood pressure as the output from the centered portion.

In addition to selecting a portion of the stress sensitive element which directly overlies the artery of interest, other factors influence the accuracy to which intra-arterial blood pressure can be measured. One primary factor influencing the accuracy to which intra-arterial blood pressure can be measured is the degree, or extent, to which the artery of interest is applanated at the time the stress sensitive element is measuring tissue stress. Although fairly accurate blood pressure measurements may be made over a wide range of applanation states, it is generally accepted that there exists a substantially unique applanation state which produces the most accurate indication of intra-arterial blood pressure. This unique applanation state is commonly known as the optimum applanation state. Much of the prior art, including those references disclosed and discussed herein in the background portion, attempt to relate optimum artery applanation to hold down pressure (hold down pressure is defined as the pressure applied against the pressure transducer as the transducer is forced against the tissue overlying the artery of interest).

It is Applicant's theory that the techniques taught in the prior art are improperly focused and accordingly may not produce results as accurate as the methodologies disclosed herein. Specifically, while hold down pressure is a parameter which may loosely correlate to artery applanation state, it is believed that there are a number of parameters which may perform this function much better. The methodologies disclosed herein set forth a number of applanation state parameters (ASP) which are believed to provide a superior measure (or indication) of applanation state. This belief is founded on the fact that the methodologies disclosed herein for determining optimum arterial applanation are based upon tonometric parameters which are sensitive to the physical events which take place when an artery is applanated. These physical events will now be explained in conjunction with FIGS. 3 and 9A–9E.

Figure 9A:
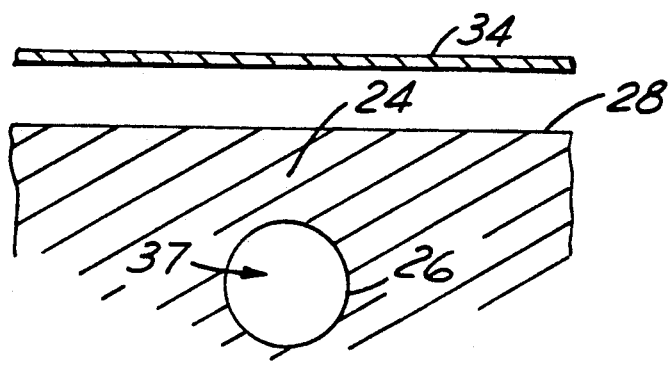
FIGS. 9a–9e are diagrammatic representations of the distortion which an artery undergoes when it is compressed.
Figure 9B:
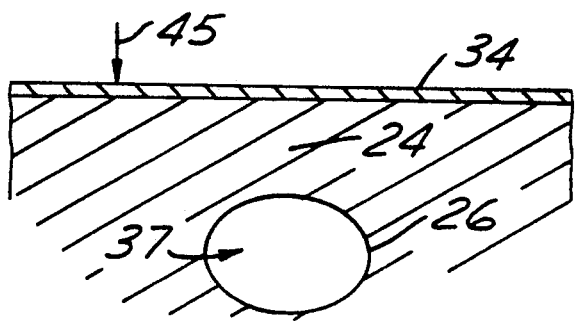
Figure 9C:
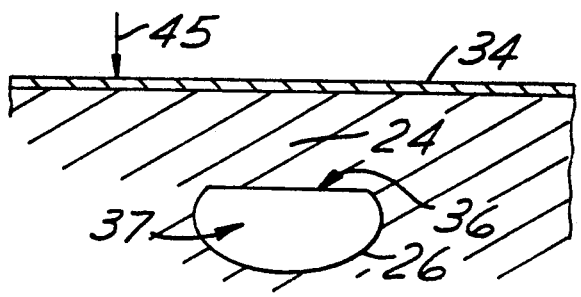
Figure 9D:
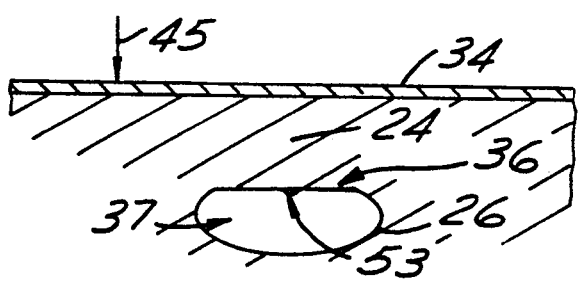
Figure 9E:
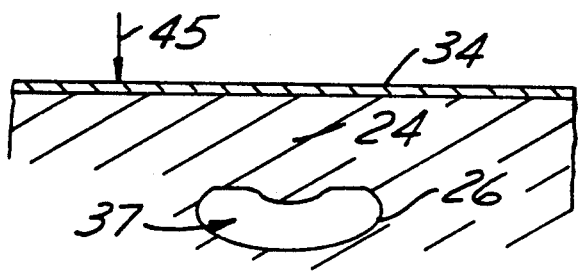

Now referring to FIGS. 3 and 9A–9E, when stress sensitive element 34 is not in contact with top surface 28 of tissue 24, opening (or lumen) 37 of artery 26 maintains a generally circular cross-section (see FIG. 9A). When stress sensitive element is brought in contact with surface 28 of tissue 24 and forced there against, different degrees of artery distortion take place depending, in part, upon the displacement caused by stress sensitive element 34 against surface 28. FIG. 9B–9E depict various stages of deformation of artery 26 as downward displacement 45 increases. As is seen in FIG. 9B, when downward displacement 45 is small lumen 37 of artery 26 is generally elliptical. As displacement 45 increases beyond that of FIG. 9B to that shown in FIG. 9C, the top surface 36 of artery 26 assumes a generally planar orientation. At this applanation state the localized contact stresses at the tissue surface (over the vessel center) are balanced with the stresses caused by the intra-arterial blood pressure. When the applanation conducting depicted in FIG. 9C exists (i.e. top surface 36 of artery 26 is generally planar), artery 26 is said to be in an optimally applanated state. If displacement 45 is increased beyond that shown in FIG. 9C to that shown in 9D, a condition of buckling 53 (or collapsing) occurs in a very small localized region of the vessel wall. In this buckled (or collapsed) state, region 53 is incapable of carrying significant additional localized contact stress. Accordingly, if displacement 45 is increased from that shown in FIG. 9D to that shown in FIG. 9E, the additional contact stresses created along buckled portion 53 are shed (or transferred) to adjacent (not yet buckled) regions. By shedding stress from one buckled region to adjacent non-buckled regions (thereby causing the previously unbuckled regions to then buckle) the stress contour exhibits a non-linear behavior. Many of the methodologies disclosed herein take advantage of this non-linear phenomenon to predict optimum applanation state.

Generalized Tonometric Estimation Methodology

Figure 10:
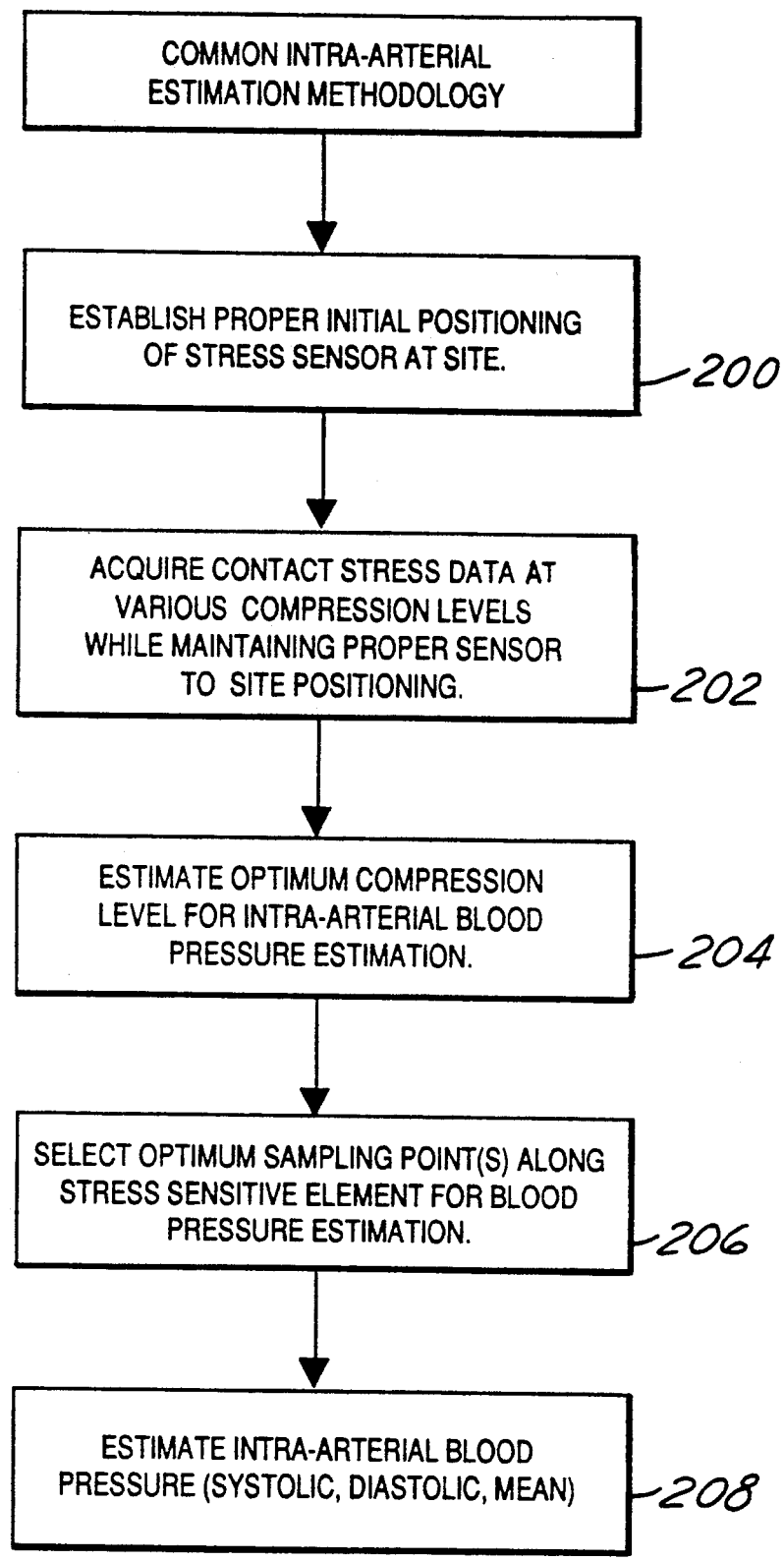
FIG. 10 is a block diagram showing the logic flow which is common to Methods 1-12 disclosed herein.

Each of the methods herein disclosed for determining the optimum arterial applanation state are utilized in a common methodology for ultimately determining (or estimating) intra-arterial blood pressure. The fundamental components of this common methodology are disclosed in FIG. 10. Now referring to FIGS. 3 and 10, preparation of monitoring intra-arterial blood pressure begins at establishing proper initial positioning of stress sensor 20 (see FIG. 3) on the user's wrist or other appropriate site 200. Once proper initial positioning is established 200, stress sensor 20 collects contact stress data 202 (see FIG. 8). Once this stress data has been collected, applanation means 29 (see FIG. 2) moves sensor 20 thereby establishing a new compression level. This process of collecting stress data continues for each unique applanation state. The movement of applanation means 29 can be accomplished in a step-wise fashion or in a continuously varying fashion. Once applanation means 29 has completed its applanation cycle, systolic, diastolic, pulsatile, and waveform mean contact stresses are derived as functions of position along the stress sensitive element (see FIG. 8) and also as functions of applanation state. From the acquired contact stress data, one or more optimum applanation methodologies are utilized for determining the optimum applanation compression level for intra-arterial blood pressure estimation 204. Once the optimum arterial compression level is determined, certain portions of the data which was collected during the optimum applanation level are selected for blood pressure estimation 206. Those selected sample points of contact stress data are then used for estimating intra-arterial blood pressure 208. This disclosure focuses upon methods used to determine optimum arterial compression 204 and methods used for selecting optimum sampling points along the stress sensitive element once the optimum arterial compression level has been found 206.

General Discussion of Applanation Optimization Parameters and Applanation State Parameters When implementing methodologies for non-invasively determining intra-arterial blood pressure, it is helpful and convenient to develop various classifications of functions. Two particular classes of parameters (or functions) disclosed herein are Applanation Optimization Parameters and Applanation State Parameters. Applanation Optimization Parameters (AOP) are parameters which provide guidance in selecting the optimum amount of artery applanation. The Applanation State Parameters (ASP) are parameters which indicate the degree to which the artery has been flattened or distorted as it is acted upon by tissue stress sensor 20. To generalize the relationship between the Applanation Optimization Parameters and the Applanation State Parameters, the Applanation Optimization Parameter AOP is a function of the Applanation State Parameter AOP(ASP). In the methods set forth herein to determine optimum states, one or more AOP(ASP) are used for determining the "best" or optimum artery applanation state. Each method disclosed herein generally operates by adjusting a selected ASP until a preferred or optimum AOP(ASP) is found. For example, in one method which is disclosed herein in detail, when AOP(ASP) equals 1.00, preferred conditions exist for estimating intra-arterial blood pressure based upon collected contact stress data.

An example of an Applanation State Parameter would be simply monitoring the displacement which is applied against the stress sensor as it is displaced against the tissue overlying the artery of interest. For example, a displacement of 10 mills (one mill is equal to one-one thousandth of an inch) may receive an Applanation State Parameter value of 1, 20 mills equals an Applanation State Parameter value of 2, etc. Another method of deriving Applanation State Parameters is simply to measure the force against tissue stress sensor 20 (see FIG. 2) as it is displaced into tissue 24 by moving means (or bellows) 29. Still another applanation state parameter may be derived by calculating the average contact stress across the entire length of the stress sensitive element. This method may include applanating an artery to a first state and then, while held in that state, calculating the average contact stress across the entire length of the stress sensitive element. Mathematically, this method is express as follows:

$$AASI_1 = \sigma_{AVG(AAS1)} = \frac{\int_0^L \sigma(x)_{AAS1}}{\int_0^L dx}$$

where:

$\sigma_{AVG(AAS1)}$ = average stress value across the length of the stress sensitive element while the artery of interest undergoes the first artery applanation state $AAS_1$ = First Artery Applanation State $AASI_1$ = First Artery Applanation State Index $\sigma(x)_{AAS1}$ = stress data sensed by stress sensing element at location x while the artery of interest undergoes the first artery applanation state x = location along the length of stress sensitive element O, L = limits of integration across the length of stress sensitive element Preferred Applanation State Parameters ASP The following list sets forth several applanation state parameters which are believed to be unique measures or indicators of the degrees or state of artery applanation. As later disclosed herein, the use of the applanation state parameters (either individually or combined) to form a composite indicator representing state of artery applanation is a key in forming functional relationships which are used in the methodologies to determine optimum arterial applanation.

A. AVERAGE DIASTOLIC CONTACT STRESS FACTOR (STRESS COLLECTED IN PASSIVE REGIONS REMOTE FROM VESSEL). [1]

(1) Average tissue diastolic contact stress collected from the most passive regions of tissue (most remote from vessel).

B. DIASTOLIC CONTACT STRESS DISTRIBUTION BREADTH FACTOR. [1],[2]

(1) Average tissue diastolic contact stress (across full length of stress sensitive element) divided by tissue diastolic contact stress at maximum tissue pulsatile stress location, or (2) Average tissue diastolic contact stress in passive tissue regions (remote from vessel) divided by average tissue diastolic contact stress in active tissue regions (over vessel), or (3) Average tissue diastolic contact stress (across full length of stress senstive element) divided by average tissue diastolic contact stress over a select portion of the stress sensitive element having maximum tissue pulsatile stress.

C. AVERAGE DIASTOLIC CONTACT STRESS (STRESS COLLECTED OVER ENTIRE LENGTH OF STRESS SENSITIVE ELEMENT). [1]

D. NORMALIZED OR DIMENSIONLESS AVERAGE DIASTOLIC CONTACT STRESS FACTOR (STRESS COLLECTED IN PASSIVE REGIONS REMOTE FROM VESSEL). [1]

(1) Ratio of the index computed by method A(1) above at applanation state of interest to that index method computed at applanation state for maximum pulsatile contact stress, or (2) Ratio of the index computed by method A(1) above at applanation state of interest to that same index method computed at any particular characteristic applanation state selected for the normalization process.

E. NORMALIZED OR DIMENSIONLESS AVERAGE DIASTOLIC CONTACT STRESS FACTOR (STRESS COLLECTED OVER ENTIRE LENGTH OF THE STRESS SENSITIVE ELEMENT). [1]

(1) Ratio of the index computed by method C above at applanation level of interest to index C above computed at applanation level for maximum pulsatile stress, or (2) Ratio of the index computer by method C above at applanation level of interest to index C above computed at any particular characteristic applanation state selected for the normalization process.

F. HOLD DOWN FORCE FACTOR (DIRECTLY MEASURED HOLD DOWN FORCE [9] APPLIED TO THE SENSOR HEAD).

G. NORMALIZED OR DIMENSIONLESS HOLD DOWN FORCE FACTOR. [9]

(1) Ratio of index computed by method F above at applanation level of interest to index F above computed at applanation level for maximum pulsatile stress, or (2) Ratio of index computed by method F above at applanation level of interest to index F above computed at any particular characteristic applanation state selected for the normalization process.

H. WRIST GEOMETRY FACTOR (MEASURED RELATIVE DISPLACEMENT WITH RESPECT TO WRIST GEOMETRICAL FEATURES).

(1) Displacement of sensor head relative to radial bone [3], [5], [6], or (2) Change in inside dimension of artery in direction of sensor head displacement [4], [5], [6], or (3) Displacement of sensor head relative to surface of skin remote from influence of sensor head. [5], [7]

I. NORMALIZED WRIST GEOMETRY FACTOR (NORMALIZED OR DIMENSIONLESS MEASURED RELATIVE DISPLACEMENT WITH RESPECT TO WRIST GEOMETRICAL FEATURES).

(1) Ratio of the index computer by method H above at applanation state of interest to that index method computed at applanation state for maximum pulsatile contact stress.

(2) Ratio of index computed by method H above at applanation level or interest to index H above computed at any particular characteristic applanation state selected for the normalization process.

J. TISSUE PULSATILE CONTACT STRESS SPATIAL DISTRIBUTION BREADTH FACTOR. [1], [2], [3]

(1) Number of sampled locations along stress sensitive element having a normalized pulsatile contact stress (with respect to spatial distribution) above some threshold level (such as 40%), or (2) Percentage (of total sampling points of the sampled locations along the stress sensitive element having a normalized pulsatile contact stress (with respect to spatial distribution) above some threshold level (such as 40%).

K. AVERAGE PULSATILE CONTACT STRESS FACTOR (STRESS COLLECTED IN THE MOST PASSIVE REGIONS OF THE DIAPHRAGM). [1], [2], [3]

(1) Average of the spatially normalized pulsatile contact stresses along a relatively small portion of the stress sensitive element (i.e. 10% to 50%) that have the smallest values of normalized pulsatile contact stress.

L. AVERAGE PULSATILE CONTACT STRESS IN THE MOST ACTIVE REGION FACTOR. [1]

M. NORMALIZED OR DIMENSIONLESS AVERAGE PULSATILE CONTACT STRESS [1] IN ACTIVE REGION FACTOR.

(1) Ratio of index calculated in L above at applanation state of interest to max value applanation state of index.

N. WRIST BAND FACTOR (WRIST BAND CIRCUMFERENCE OR CHANGE IN CIRCUMFERENCE (DISPLACEMENT) PRODUCED TO CREATE DESIRED VESSEL APPLANATION BY TONOMETER SENSOR HEAD IN A WRIST WORN TONOMETRY CONFIGURATION). [7]

O. WRIST BEND TENSION FACTOR (WRIST BAND TENSION OR TENSILE FORCE PRODUCED TO CREATE DESIRED VESSEL APPLANATION BY TONOMETER SENSOR HEAD IN A WRIST WORN TONOMETER CONFIGURATION). ALSO INCLUDES THE NORMALIZED VERSION OF THIS METHOD WITH RESPECT TO STATE OF APPLANATION.

P. NUMBER OF TURNS FACTOR. NUMBER OF TURNS, ANGULAR DISPLACEMENT, OR LINEAR DISPLACEMENT OR A WRIST TIGHTENING MECHANISM [8] (MANUAL OR MOTOR DRIVEN) OR ANY RELATED COMPONENTS THEREOF (SUCH AS ARMATURE OR GEARS) PRODUCED TO CREATE DESIRED VESSEL APPLANATION BY TONOMETER SENSOR HEAD IN A WRIST WORN TONOMETER CONFIGURATION.

Q. DIRECT SENSOR HEAD TO SENSOR HOUSING FACTOR. DIRECTLY MEASURED RELATIVE DISPLACEMENT BETWEEN [7] SENSING HEAD AND ADJACENT TONOMETER SENSOR HOUSING TO TISSUE CONTACT INTERFACE (EITHER HAND HELD OR WRIST WORN TONOMETER).

R. INDIRECT SENSORHEAD TO SENSOR HOUSING FACTOR. INDIRECTLY MEASURED RELATIVE DISPLACEMENT BETWEEN [8] SENSING HEAD AND ADJACENT TONOMETER SENSOR HOUSING TO TISSUE CONTACT INTERFACE (EITHER HAND HELD OR WRIST WORN TONOMETER).

S. SINGLE PARAMETER FACTOR. METHODOLOGY WHEREBY EACH OF THE PARAMETERS LISTED ABOVE ARE INDIVIDUALLY CONSIDERED TO BE INDICATORS OF THE STATE OR LEVEL OR APPLANATION OR DISTORTION OF THE ARTERIAL VESSEL UNDERLYING THE SENSOR HEAD/TISSUE INTERFACE.

T. MULTIPLE PARAMETER FACTOR. METHODOLOGY WHEREBY ANY TWO OR MORE OF THE PARAMETERS LISTED ABOVE ARE ANALYTICALLY COMBINED TOGETHER TO FORM A COMBINED OR COMPOSITE INDICATOR OF THE STATE OR LEVEL OR APPLANATION OR DISTORTION OF THE ARTERIAL VESSEL UNDERLYING THE SENSOR HEAD/TISSUE INTERFACE.

(1) Methodology for combining the individual applanation parameters into a composite applanation index whereby appropriate conditioning and weighting factors are applied to the individual parameters prior to their combination.

U. USE OF A VESSEL APPLANATION INDEX AS DESCRIBED IN A-T ABOVE (EITHER INDIVIDUALLY OR COMPOSITE COMBINED APPLANATION INDEXES INDICATING STATE OF VESSEL APPLANATION, STATE OF VESSEL DISTORTION, OR STATE OF HOLD DOWN) AS A KEY INGREDIENT OR ELEMENT UTILIZED IN FUNCTIONAL RELATIONSHIPS AND CRITERIA EMPLOYED IN METHODOLOGY TO ESTABLISH OPTIMUM STATE OF VESSEL APPLANATION (OR DISTORTION) ALLOWING ACCURATE BLOOD PRESSURE PREDICTIONS.

NOTES:
(1) THESE APPLANATION STATE PARAMETERS ARE ESPECIALLY IMPORTANT IN THAT THEY UTILIZE TISSUE CONTACT STRESS DATA ALREADY BEING UTILIZED FROM THE STRESS SENSOR ITSELF AND DO NOT REQUIRE DATA FROM A SEPARATE SENSOR OR TRANSDUCER.
(2) THIS APPLANATION STATE PARAMETER IS UNIQUE IN THAT IT IS A MEASURE OF THE CHANGE IN "SHAPE" OF THE CONTACT STRESS DISTRIBUTION PROFILE (ALONG THE LENGTH OF THE STRESS SENSITIVE ELEMENT) AS ONE CHANGES THE STATE OR LEVEL OF VESSEL APPLANATION. IT IS A DIMENSIONLESS INDEX.
(3) THIS IS AN INDICATION OF PHYSICAL DISTORTION OR "FLATTENING" OF THE UNDERLYING ARTERY.
(4) THIS IS UNIQUE IN THAT IT IS A DIRECT MEASURE OF VESSEL DISTORTION IN THE UNDERLYING ARTERY.
(5) DIRECT MEASURES OF DISPLACEMENT OR RELATIVE DISPLACEMENT (NOT OF FORCE).
(6) ONE METHOD COULD UTILIZE TISSUE ACOUSTIC/ULTRASONIC DISTANCE MEASURING PRINCIPLES EMBODYING AN ULTRASONIC SENSOR IN THE TONOMETER HEAD ITSELF.
(7) EXAMPLES WOULD BE UTILIZATION OF A LINEAR DISPLACEMENT TRANSDUCER, CAPACITIVE DISTANCE MEASURING SYSTEM, AN OPTICAL DISTANCE MEASURING SYSTEM, OR AN ACOUSTIC DISTANCE MEASURING SYSTEM.
(8) POSITION OF DRIVING OR POSITION ADVANCEMENT MECHANISM (EITHER HAND OR MOTOR ACTUATED, TURNED, OR DRIVEN) IN TERMS OF NUMBER OF TURNS OF SCREW, GEAR OR SHAFT OR ARMATURE OR ANGULAR DISPLACEMENT OF ANY RELATED PORTIONS OR COMPONENTS OF SUCH AND OR MOTOR OPERATED POSITION ADVANCEMENT MECHANISM.
(9) SUCH AS WITH A LOAD CELL OR OTHER FORCE TRANSDUCER (E.G. TACTILE SENSOR) OR VIA STRAIN GAGING A BEAM OR OTHER ATTACHMENT STRUCTURE THAT TRANSMITS THE HOLD DOWN FORCE DIRECTLY TO THE TONOMETER SENSOR HEAD.

Preferred Applanation Optimization Parameters

In addition to the above listed applanation state parameters, the methodologies for determining optimum arterial applanation utilized applanation optimization parameters. Below is a list of applanation optimization parameters used in the methods disclosed herein for determining optimum arterial applanation. A short definition follows each listed applanation optimization parameter.

A. SPATIALLY AVERAGED STRESS PARAMETERS
  1). PULSATILE STRESS PARAMETER (PPAR)
    At any given state of applanation, it is a measure of the spatial average (or weighted a spatial average) change in stress between systole and diastole [pulse stress] in the region of the sensor receiving maximum pulse energy.
  2). DIASTOLIC STRESS PARAMETER (DPAR)
    At any given state of applanation, it is a measure of the spatial average (or weighted spatial average) contact stress at diastole in the region of the sensor receiving maximum pulse energy.
  3). SYSTOLIC STRESS PARAMETER (SPAR)
    At any given state of applanation, it is a measure of the spatial average (or weighted spatial average) contact stress at systole in the region of the sensor receiving maximum pulse energy.
  4). MEAN STRESS PARAMETER (MPAR)
    At any given state of applanation, it is a measure of the spatial average (or weighted spatial average) contact stress corresponding to the blood pressure waveform mean in the region of the sensor receiving maximum pulse energy.

B. DIASTOLIC DISTRIBUTION BREADTH PARAMETER (DDBP)
  A measure of the spatial uniformity of the diastolic stress distribution profile over the length of the stress sensitive element (normalized to the most pulsatily energetic region(s) of the stress sensitive element).

C. MEAN DISTRIBUTION BREADTH PARAMETER (MDBP)
  A measure of the spatial uniformity of the waveform mean stress distribution profile over the length of the stress sensitive element (normalized to the most pulsatily energetic region(s) of the stress sensitive element).

D. PULSE SPREAD PARAMETER (PSP)
  A measure of the maximum deviation in pulse stress occurring in the most pulsatily energetic region(s) of the stress sensitive element.

E. PULSE DISTRIBUTION BREADTH PARAMETER (PDBP)
  A measure of the spatial uniformity of the pulse stress distribution profile over the length of the stress sensitive element.

F. STRESS SPREAD PARAMETERS (SSPAR)
  (1) Pulsatile Spread Parameter (PSP)
    At any given state of applanation, it is a measure of the maximum spread or difference between the maximum pulsatile stress and the minimum pulsatile stress occurring in the region of the stress sensitive element receiving maximum pulse energy $PSP = \sigma_{PCSMAX} - \sigma_{PCSMIN}$ within the pulsatily energetic region.
  (2) Diastolic Spread Parameter (DSP)
    At any given state of applanation, it is a measure of the maximum spread or difference between the maximum diastolic stress and the minimum diastolic stress occurring in the region of the stress sensitive element receiving maximum pulse energy. $DSP = \sigma_{DCSMAX} - \sigma_{DCSMIN}$ within the pulsatily energetic region.
  (3) Systolic Spread Parameter (SSP)

At any given state of applanation, it is a measure of the maximum spread or difference between the maximum systolic stress and the minimum systolic stress occurring in the region of the stress sensitive element receiving maximum pulse energy. $SSP = \sigma_{SCSMAX} - \sigma_{SCSMIN}$ within the pulsatily energetic region.

(4) Mean Spread Parameter (MSP)

At any given state of applanation, it is a measure of the maximum spread of difference between the maximum waveform mean stress and the minimum waveform mean stress occurring in the region of the stress sensitive element receiving maximum pulse energy. $MSP = \sigma_{MCSMAX} - \sigma_{MCSMIN}$ within the pulsatily energetic region.

G. STRESS DEVIATION PARAMETERS (SDPAR)

(1) Pulsatile Deviation Parameter (PDP)

At any state of applanation, it is a measure of standard deviation in pulsatile stress values $\sigma_{PCS}(x)$ sampled along the stress sensitive element in the region of the stress sensitive element receiving maximum pulse energy.

(2) Diastolic Deviation Parameter (DDP)

At any state of applanation, it is a measure of standard deviation in diastolic stress values $\sigma_{DCS}(x)$ sampled along the stress sensitive element in the region of the stress sensitive element receiving maximum pulse energy.

(3) Systolic Deviation Parameter (SDP)

At any state in applanation, it is a measure of standard deviation in systolic stress values $\sigma_{SCS}(x)$ sampled along the stress sensitive element in the region of the stress sensitive element receiving maximum pulse energy.

(4) Mean Deviation Parameter (MDP)

At any state of applanation, it is a measure of standard deviation in mean stress values $\sigma_{MCS}(x)$ sampled along the stress sensitive element in the region of the stress sensitive element receiving maximum pulse energy.

G. STRESS SPATIAL CURVATURE PARAMETERS (1) PULSATILE CURVATURE PARAMETER (PCPAR)

At any given state of applanation, it is a measure of the spatial curvature of the pulsatile contact stress versus distance (along the stress sensitive element) function in the pulsatily active region of the stress sensitive element. It is defined as the 2nd derivative of the pulsatile contact stress versus distance function evaluated at the effective center of the pulsatily active region of the stress sensitive element.

$$PCPAR = \left. \frac{\partial^2 \sigma_{PCS}(x)}{\partial x^2} \right|_{x=\bar{x}}$$

(2) DIASTOLIC CURVATURE PARAMETER (DCPAR)

At any given state of applanation, it is a measure of the spatial curvature of the diastolic contact stress versus distance (along the stress sensitive element) function in the pulsatily active region of the stress sensitive element. It is defined as the 2nd derivative of the diastolic contact stress versus distance function evaluated at the effective center of the pulsatily active region of the stress sensitive element.

$$DCPAR = \left. \frac{\partial^2 \sigma_{DCS}(x)}{\partial x^2} \right|_{x=\bar{x}}$$

(3) SYSTOLIC CURVATURE PARAMETER (SCPAR)

At any given state of applanation, it is a measure of the spatial curvature of the systolic contact stress versus distance (along the stress sensitive element) function in the pulsatily active region of the stress sensitive element. It is defined as the 2nd derivative of the systolic contact stress versus distance function evaluated at the effective center of the pulsatily active region of the stress sensitive element.

$$SCPAR = \left. \frac{\partial^2 \sigma_{SCS}(x)}{\partial x^2} \right|_{x=\bar{x}}$$

(4) MEAN CURVATURE PARAMETER (MCPAR)

At any given state of applanation, it is a measure of the spatial curvature of the mean contact stress versus distance (along the stress sensitive element) function in the pulsatily active region of the stress sensitive element. It is defined as the 2nd derivative of the mean contact stress versus distance function evaluated at the effective center of the pulsatily active region of the stress sensitive element.

$$MCPAR = \left. \frac{\partial^2 \sigma_{MCS}(x)}{\partial x^2} \right|_{x=\bar{x}}$$

List of Methods for Estimating Optimum Arterial Applanation

Below is a list of twelve methods disclosed herein for estimating optimum arterial compression.

Method 1: The pulsatile stress parameter reaches an optimum fraction of its maximum value.

Method 2: The mean distribution breadth parameter reaches an optimum value.

Method 3: The diastolic distribution breadth parameter reaches an optimum value.

Method 4: The pulse distribution breadth parameter reaches an optimum value.

Method 5: The incremental change in pulse distribution breadth parameter reaches an optimum value.

Method 6: The derivative of the pulse spread parameter reaches an optimum value.

Method 7: The derivative of the pulse distribution breadth parameter reaches an optimum value.

Method 8: The derivative of the diastolic distribution breadth parameter reaches an optimum value.

Method 9: Second derivative of spatially averaged stress parameters reaches an optimum value.

Method 10: Second derivative of stress spatial curvature parameters reaches an optimum value.

Method 11: The derivative of the stress spread parameters or the derivative of the stress deviation parameter reaches an optimum value.

Method 12: Two or more methods are selected from Methods 1 through 11 and combined to form additional methodologies for estimating optimum arterial applanation.

DETAILED DISCUSSION OF METHOD 1

This method utilizes the Pulsatile Stress Parameter (PPAR) to determine the optimum applanation state of the artery of interest. The Pulsatile Stress Parameter PPAR is defined as the average difference between the systolic contact stress $\sigma_{SCS}(x)$ and diastolic contact stress $\sigma_{DCS}(x)$ in the region or regions of the stress sensitive element having the greatest pulse energy content. Mathematically, PPAR is defined as follows:

$$PPAR = \frac{1}{c-b} \int_b^c (\sigma_{SCS}(x) - \sigma_{DCS}(x)) \cdot dx$$

Figure 11:
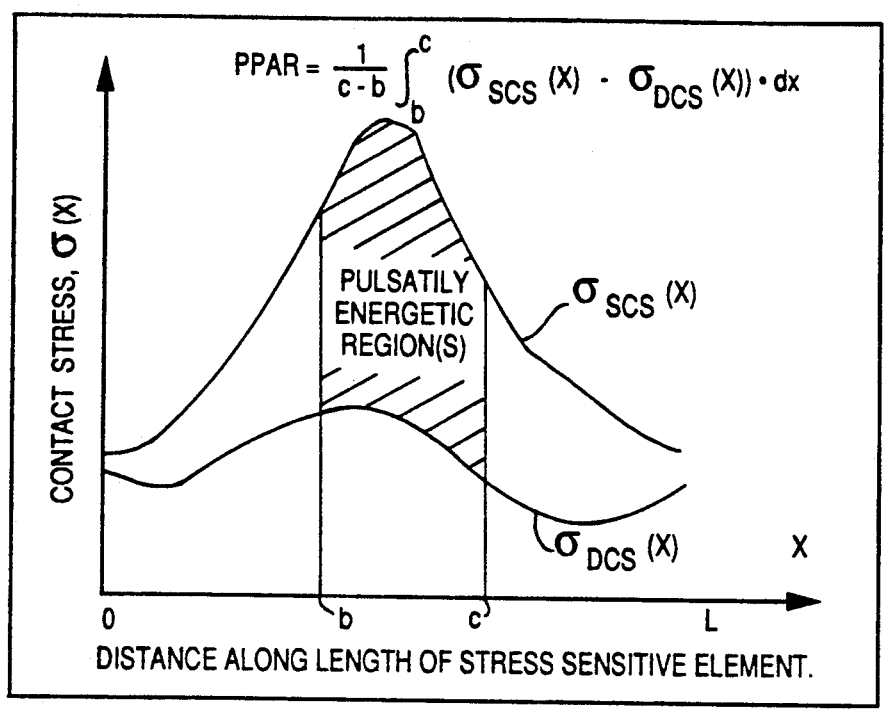
FIG. 11 is a graphical representation of the calculation of the PPAR parameter.

A graphical representation of the method of calculating PPAR is shown in FIG. 11. It is important to note that the PPAR parameter is calculated between bounds b and c. Bounds b and c represent the region having the greatest pulse energy content. Method of determining the bounds for the region of greatest pulse energy content are found later in this disclosure under the subheading Methods of Determining Limits of Integration When Calculating PPAR.

Because the following relationship exists:

$$\sigma_{SCS}(x) - \sigma_{DCS}(x) = \sigma_{PCS}(x)$$

PPAR as defined in FIG. 11 is equivalently expressed as follows:

$$PPAR = \frac{1}{c-b} \int_b^c \sigma_{PCS}(x) \cdot dx$$

Figure 12:
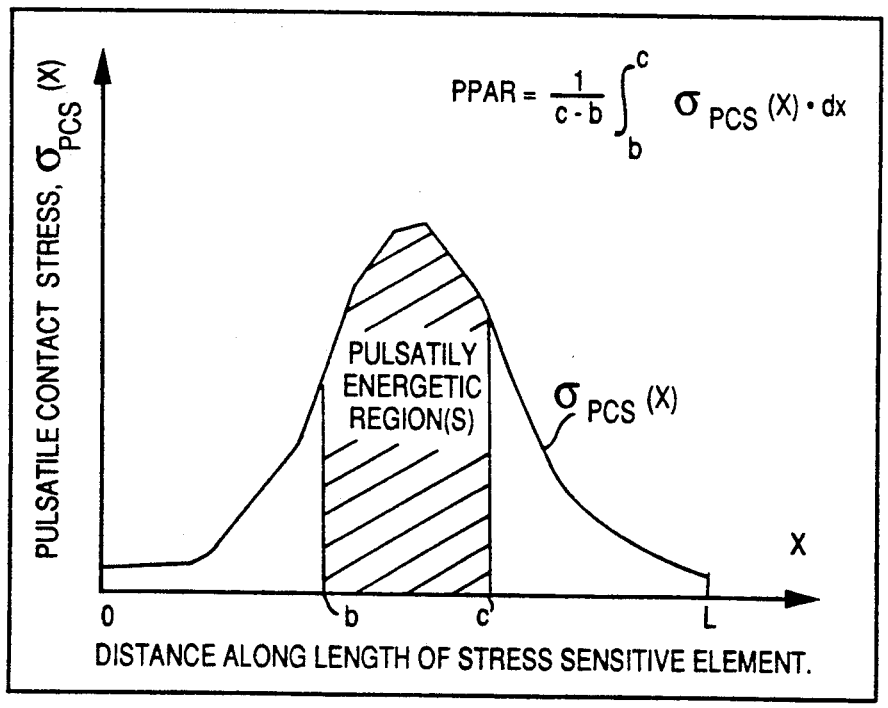
FIG. 12 is a graphical representation of an equivalent manner of calculating the PPAR parameter.

This equivalent manner of calculating PPAR is graphically depicted in FIG. 12.

Figure 13:
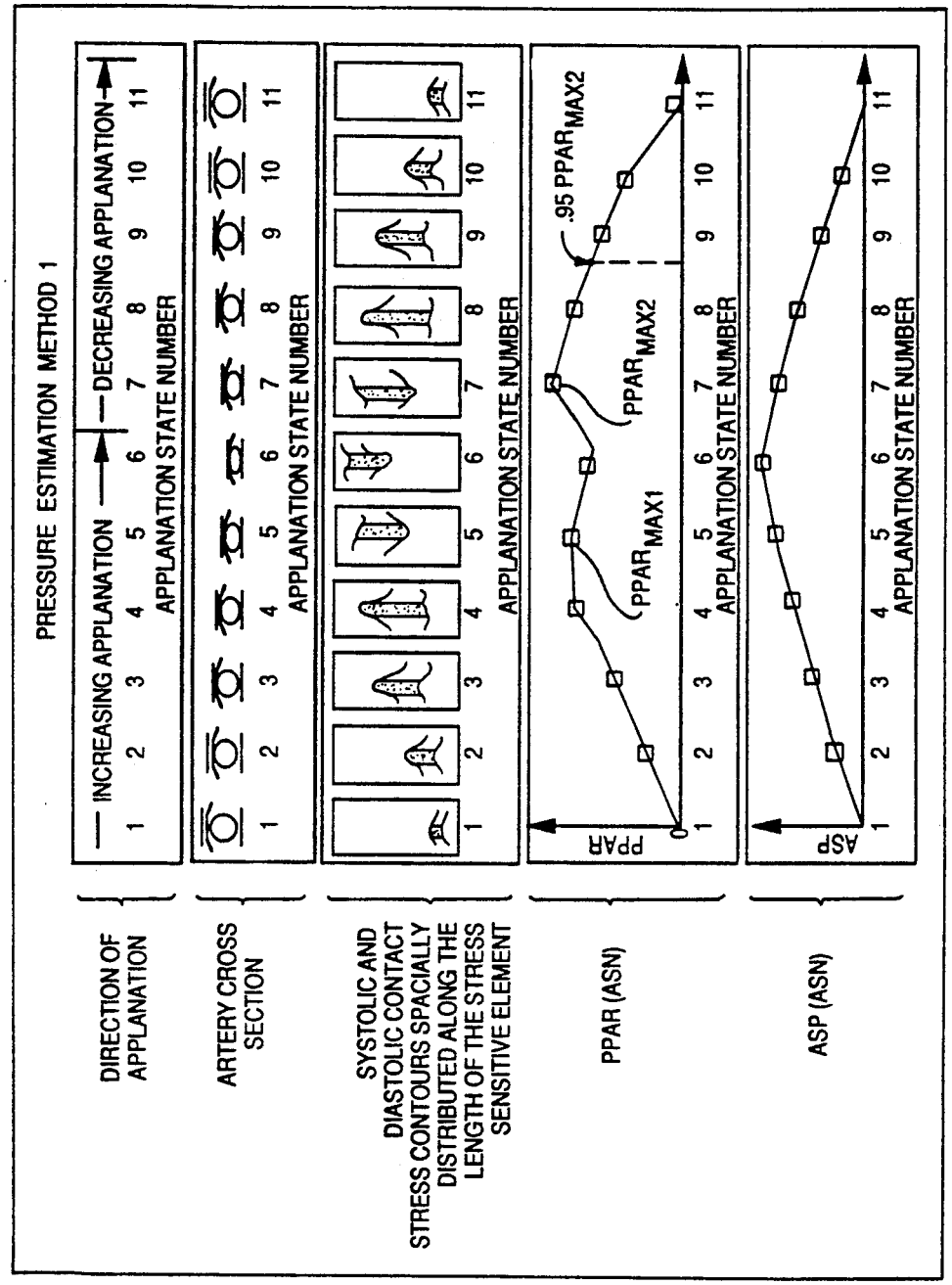
FIG. 13 is a combined graphical and diagrammatical representation of the method steps utilized in generating the PPAR parameter as a function of ASP.

Now referring to FIG. 13, the implementing of Method 1 includes the following steps:

1) Using the artery applanation control mechanism 29 (see FIG. 2) to adjust the state of artery applanation through a broad range of applanation states (the applanation states are represented by the applanation state numbers shown in FIG. 13) while acquiring contact stress data (as depicted in FIG. 11) at various applanation states.

2) At each applanation state, computing PPAR and computing ASP. The preferred ASP for Method 1 is either displacement (as set forth in paragraphs C and D in the previous discussion dealing with applanation state parameters) or the average diastolic contact stress computed as follows:

$$\sigma_{DCSAVG} = \frac{1}{L} \int_0^L \sigma_{DCS}(x) \cdot dx$$

3) Creating a function relating PPAR to the selected ASP (i.e. PPAR (ASP)).
4) Defining the optimum applanation state to be when PPAR (ASP) reaches 95% of its maximum value.
5) Calculating the optimum applanation state as follows:

$$PPAR_{opt} = PPAR_{max} \times 0.95$$

In implementing the above-discussed applanation optimization process, the optimum applanation state is found by first increasing the arterial applanation until the PPAR reaches a first maximum $PPAR_{max_1}$ and then diminishes by a specified fraction of the maximum value. Next, the applanation is reduced, and typically, PPAR will increase temporarily to a second maximum $PPAR_{max_2}$. Upon further reduction of applanation, when PPAR reaches approximately 95% of the second maximum, conditions are met for estimation of true arterial blood pressure. This process is shown in the graph of PPAR(ASN) found in FIG. 13. Alternatively, the estimation can be made at other points including the interval prior to $PPAR_{max_1}$ in which applanation is increasing.

As discussed above, and as evidenced in the graph of PPAR(ASN) found in FIG. 13, stress data is collected during the interval of increasing applanation as well as during the interval of decreasing applanation. Although stress data collected during either or both of the intervals may be used for computing the applanation optimization parameter as well as the applanation state parameter, the preferred method is to use the stress data which is collected during decreasing applanation. This is the preferred method because it is believed that stress data collected during the decreasing applanation interval more closely predicts the actual intra-arterial blood pressure than that collected during the increasing applanation interval. Unless otherwise stated, the decreasing applanation interval will be the preferred interval for all methods (Methods 1-11) disclosed herein.

Although 95% has been disclosed herein as the optimum fraction to use when determining optimum arterial applanation, a preferred method of determining the exact optimum fraction is to use empirically collected data in which tonometric versus automatic cuff or invasive blood pressure values are statistically correlated. The preferred fraction may also vary depending on certain factors such as whether applanation is increasing/decreasing, sex (and age) of person being examined, etc. Initial studies indicate that results are more uniform when applanation is decreasing and therefore it is the preferred mode when collecting contact stress data.

Methods of Determining Limits of Integration When Calculating PPAR

A preferred method for determining the limits of integration (b and c) employs the concept of energy transfer. This concept is based on the theory that the energy coupling between the artery of interest and the contact stress element is greatest in the immediate vicinity of the artery of interest. The boundaries of this high energy region are used to define the integration limits (b, c). Thus, one can determine the limits of integration (b, c) by determining which portion (or portions) of the stress sensitive element is in receipt of the maximum contact stress energy. This method uses the square of the contact stress values to obtain a measure of contact stress energy and thereby construct a relationship between contact stress energy and position along the length of the stress sensitive element.

Figure 14:
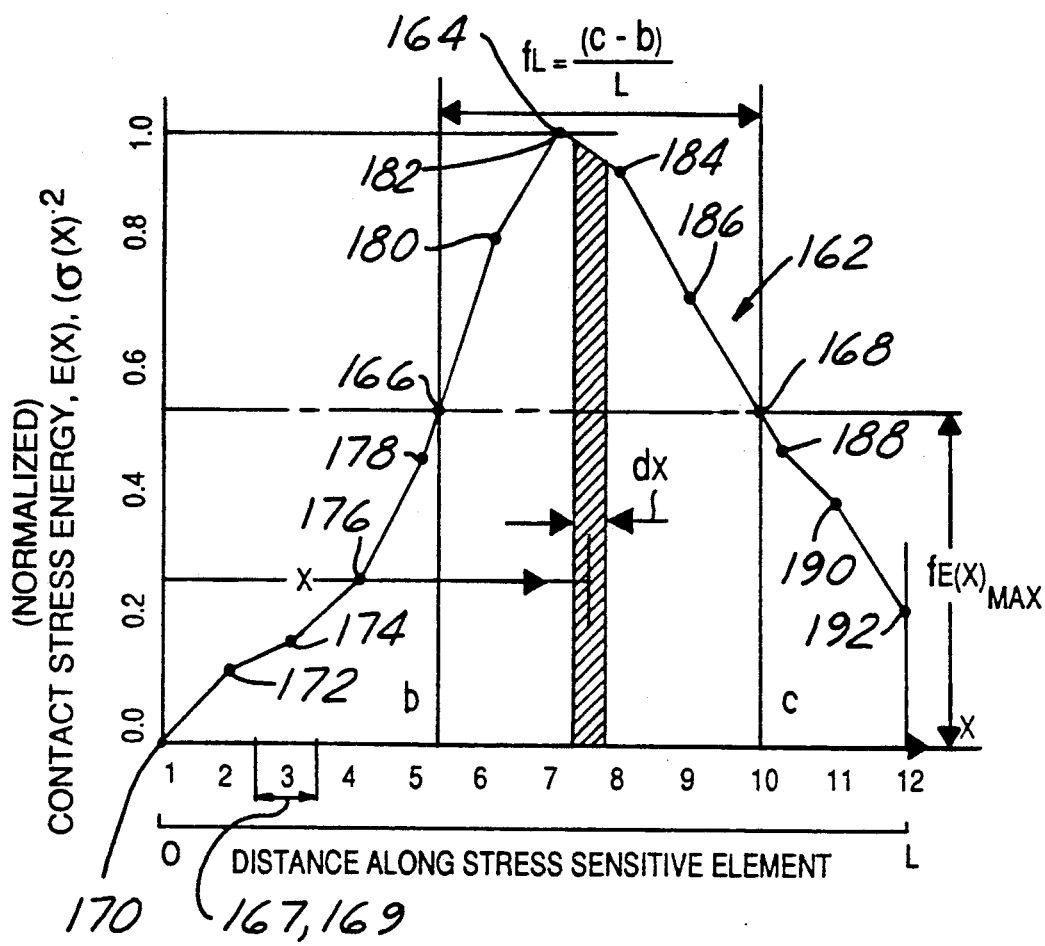
FIG. 14 is a graph showing contact stress energy as a function of distance along the stress sensitive element.

The above-referenced methodology is demonstrated graphically in FIG. 14. To implement this method of finding the limits of integration (b, c), one must first select one of the stress contours as set out in FIG. 8. While any one of the four stress contours may perform satisfactorily when implementing this method, the pulsatile stress energy contour is preferred. Thus, after obtaining pulsatile stress values across the length of the stress sensitive element (as depicted in graph 160 of FIG. 8), each pulsatile stress value (exemplified at 156) is squared thereby relating pulsatile contact stress energy $E(x)$ to distance along the stress sensitive element.

This method is in stark contrast with the approach of the prior art of simply calculating various parameters over the entire length of the stress sensitive element. The reason this approach is believed to be superior over that of calculating parameters of the full length of the stress sensitive element is simply that this method ignores the portions along the stress sensitive element which make only a minor contribution to the function being examined. Accordingly, this approach eliminates from consideration portions of the function being considered which are not centered over the artery of interest. Two methods will now be discussed, each of which can be used for determining the region (or regions) over which the PPAR parameter can be computed.

Percent of Maximum Method

The first method for determining the limits over which the centroid of a selected function will be computed, includes using only those regions of the select function which exceed an arbitrarily selected threshold fraction of the maximum value of the function. For example, applying this method to the contact stress energy function as set out in FIG. 14, first, maximum 164 is determined and then a predetermined portion of the maximum is taken. Suppose, for example, that 50 percent of maximum 164 will serve as the threshold fraction. This fraction intersects the contact stress energy function at points 166 and 168 thereby forming the limits (b, c) over which the PPAR function will be calculated. It is important to note that although the function depicted in FIG. 14 is shown having only one contiguous region which satisfies the percent of maximum condition, it is probable that under actual use conditions, several discontiguous regions will satisfy the percent maximum condition. In this case, one would simply calculate the PPAR function over each of the discontiguous regions of the energy curve which satisfy the percent of maximum condition.

Percent of Stress Sensitive Element Method

The second method of determining limits (b, c) includes using selected portions of greatest magnitude of the contact stress energy function that have a cumulative total length equal to a predetermined percentage of the total length of the stress sensitive element. This method can be easily explained in conjunction with FIGS. 6 and 14. As seen in FIG. 6, sensing diode 48b is capable of sensing deflections along stress sensitive element 34 along regions or portions 167, 169 of stress sensitive element 34. Thus, when viewing point 174 of FIG. 14 (which we are assuming is the representative output of detector 48b), we see that this output does not represent a point along stress sensitive element 34, but rather represents the composite stresses served along continuous portion 167 and 169 of stress sensitive element 34. Accordingly, each output value 170 through 192 corresponds to one or more portions along stress sensitive element 34. Thus for example, in applying the present method of determining limits (b, c) from the contact stress energy function disclosed in FIG. 14, the following steps are followed:

1. Ordering the contact stress energy values 170–192 according to magnitude.
2. Associating each of the contact energy stress values with a predetermined segment length, or lengths along the length of the stress sensitive element (e.g. stress value 174 is associated with lengths 167 and 169).
3. Selecting the contact stress energy values of greatest magnitude as previously ordered and totaling the lengths of each predetermined segment that is associated with the selected contact stress energy values.
4. Setting n equal to the number of contact stress energy values selected when the cumulative predetermined segment lengths (as totaled in step 3) exceed a predetermined percentage of the length of the stress sensitive element.
5. Computing the centroid of contact stress energy using only those n segments selected.

As with the previously disclosed percent of maximum method of determining boundaries (b, c), this method may produce selected regions which are noncontiguous. Nonetheless, the disclosed method is applied identically regardless of whether the regions are contiguous or non-contiguous.

Although the above two methods for determining limits of integration (b, c) have been discussed in the context of calculating the PPAR parameter, they are equally applicable to methods 2 through 12 discussed hereinafter. Because the above two methods of determining the limits of integration are executed the same, regardless of which method is used, they will not be discussed in conjunction with methods 2 through 12.

Selection of Stress Sensitive Element Region for Estimating Intra-Arterial Blood Pressure Once the PPAR parameter is determined and optimized, the systolic and diastolic contact stress contours which correspond to the optimized PPAR parameter are analyzed to determine the best physical location (or locations) along the length of the stress sensitive element from which intra-arterial blood pressure may be estimated. There are two preferred techniques for estimating which locations along the stress sensitive element are best suited for estimated intra-arterial pressure. These two techniques—Technique A and Technique B—will now be explained in detail in conjunction with FIGS. 13, 15 and 16.

ESTIMATING TECHNIQUE A

Figure 15:
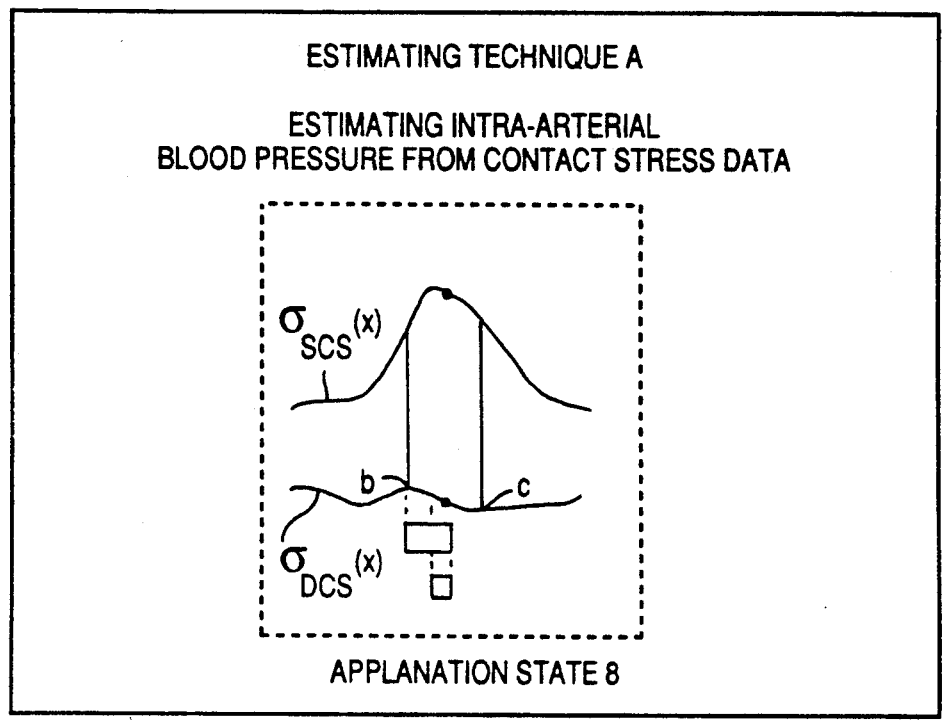
FIG. 15 is a graphical representation showing estimating technique for estimating intra-arterial blood pressure from contact stress data.

Now referring to FIGS. 13 and 15, assume for the moment that when the PPAR parameter was calculated, and optimized, the result of that optimization was that applanation state 8 (see FIG. 13) was the optimum applanation state. The systolic contact stress $\sigma_{SCS}(x)$ and the diastolic contact stress $\sigma_{DCS}(x)$ as they exist for applanation state 8, are shown in FIG. 15. In implementing Technique A, we first chose a subregion 210 of the defined area having maximum pulse energy 208. Subregion 210 will typically be two-thirds of the width of region 208. Subregion 210 will be chosen at that fraction of the width of 208 which have the greatest pulsatile contact stress $\sigma_{PCS}(x)$. Then, a yet smaller fraction 212 (typically one-half of the width of subregion 210) is determined by finding the subregion within region 210 having the smallest diastolic contact stress $\sigma_{DCS}(x)$. The diastolic contact stress point 214 and the systolic contact stress point 216 corresponding to subregion 212 is then used as the estimate of intra-arterial blood pressure systole and diastole points respectively.

ESTIMATING TECHNIQUE B

Figure 16:
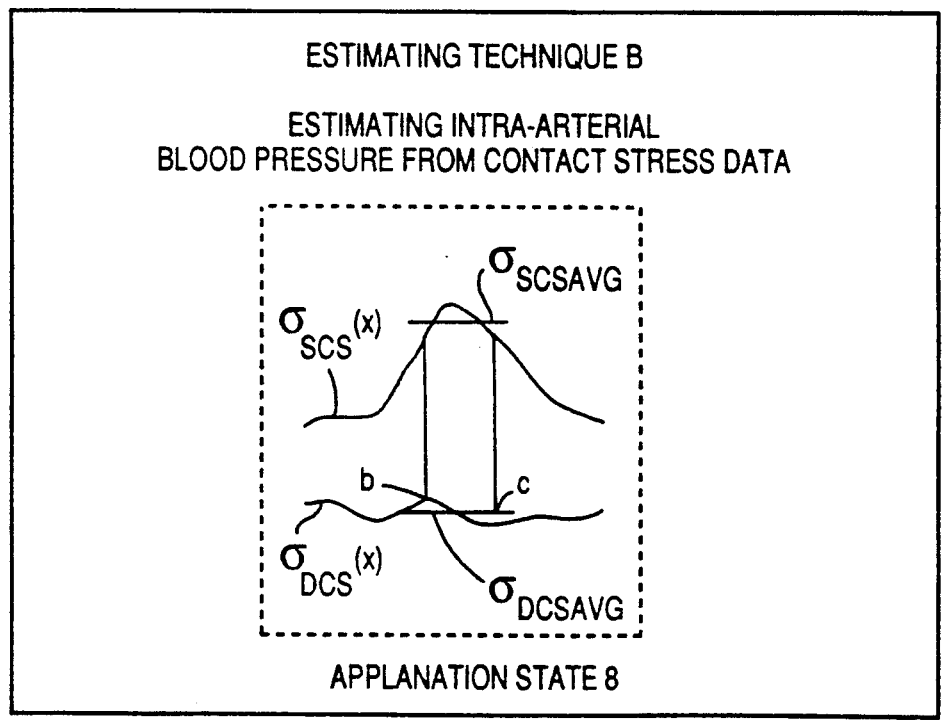
FIG. 16 is a graphical representation of Estimating Technique B for estimating intra-arterial blood pressure from contact stress data.

Now referring to FIGS. 13 and 16, assuming that applanation state 8 is determined to be the optimum applanation state after applying the PPAR criteria, Technique B estimates the intra-arterial systolic and diastolic blood pressure points to be the average diastolic contact stress $\sigma_{DCSAVG}$ and the average systolic contact stress $\sigma_{SCSAVG}$ respectively over the interval bounded by b, c. The mathematical formula for computing $\sigma_{DCSAVG}$ is as follows:

$$\sigma_{DCSAVG} = \frac{1}{b-c} \int_b^c \sigma_{DCS}(x) \cdot dx$$

The mathematical formula for computing $\sigma_{SCSAVG}$ is as follows:

$$\sigma_{SCSAVG} = \frac{1}{b-c} \int_b^c \sigma_{SCS}(x) \cdot dx$$

Although Techniques A and B have been presented in the context of estimating intra-arterial blood pressure after applying the optimization methodology of Method 1, they are also applicable to optimization methodologies 2 through 12, and their application to those methodologies is directly analogous to that which has been shown in connection with Method 1 (the optimization of the PPAR parameter). For that reason, the application of Estimation Techniques A and B will not be detailed in conjunction with the disclosure of Methodologies 2 through 12.

INTERPOLATION BETWEEN APPLANATION LEVELS

In the previous example, we assumed that the calculation of $PPAR_{OPT}$ generated an optimum applanation level corresponding to applanation state No. 8. Of course, there will be some cases where the optimum applanation state will fall between two applanation state numbers (such as is the case shown in FIG. 13 wherein 95% of $PPAR_{max2}$ falls between applanation states 8 and 9). In practice when a finite number of applanation states are used (and it happens that the optimum applanation state falls between two applanation states), it may be necessary to interpolate between the two states in order to approximate, as close as possible, the intra-arterial systolic and diastolic blood pressure points. Two preferred interpolation techniques will now be disclosed. The first interpolation technique—Interpolation Technique A—is the preferred interpolation technique used in conjunction with Estimating Technique A. The second disclosed interpolating technique—Interpolation Technique B—is the preferred interpolation technique used in conjunction with Estimating Technique B.

INTERPOLATION TECHNIQUE A

Figure 17:
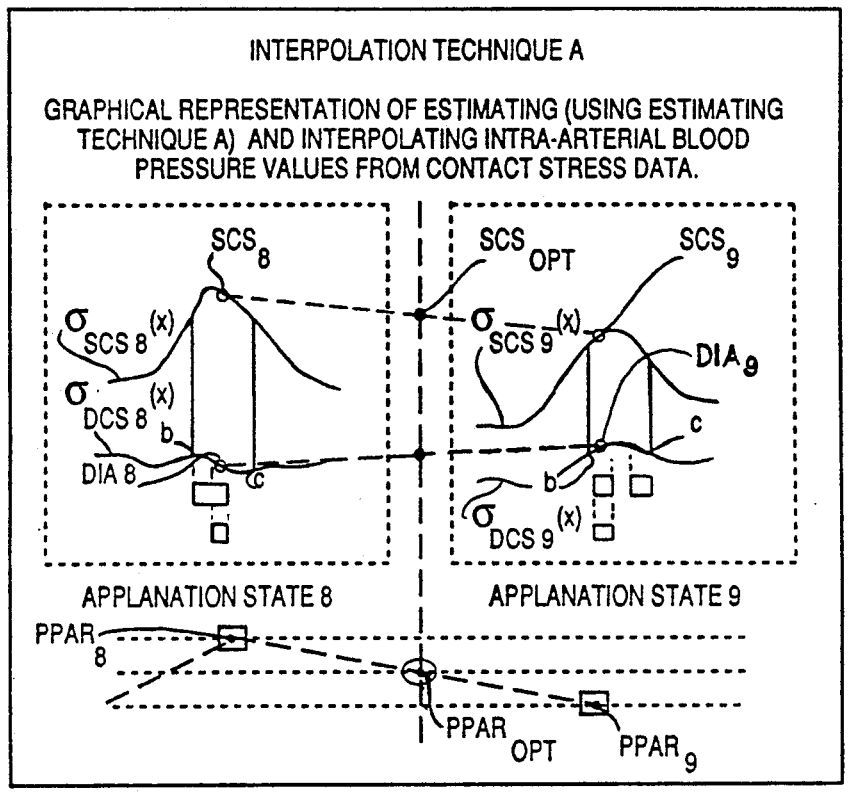
FIG. 17 is a graphical representation showing Interpolation Technique A for interpolating intra-arterial blood pressure values from contact stress data.
Figure 18:
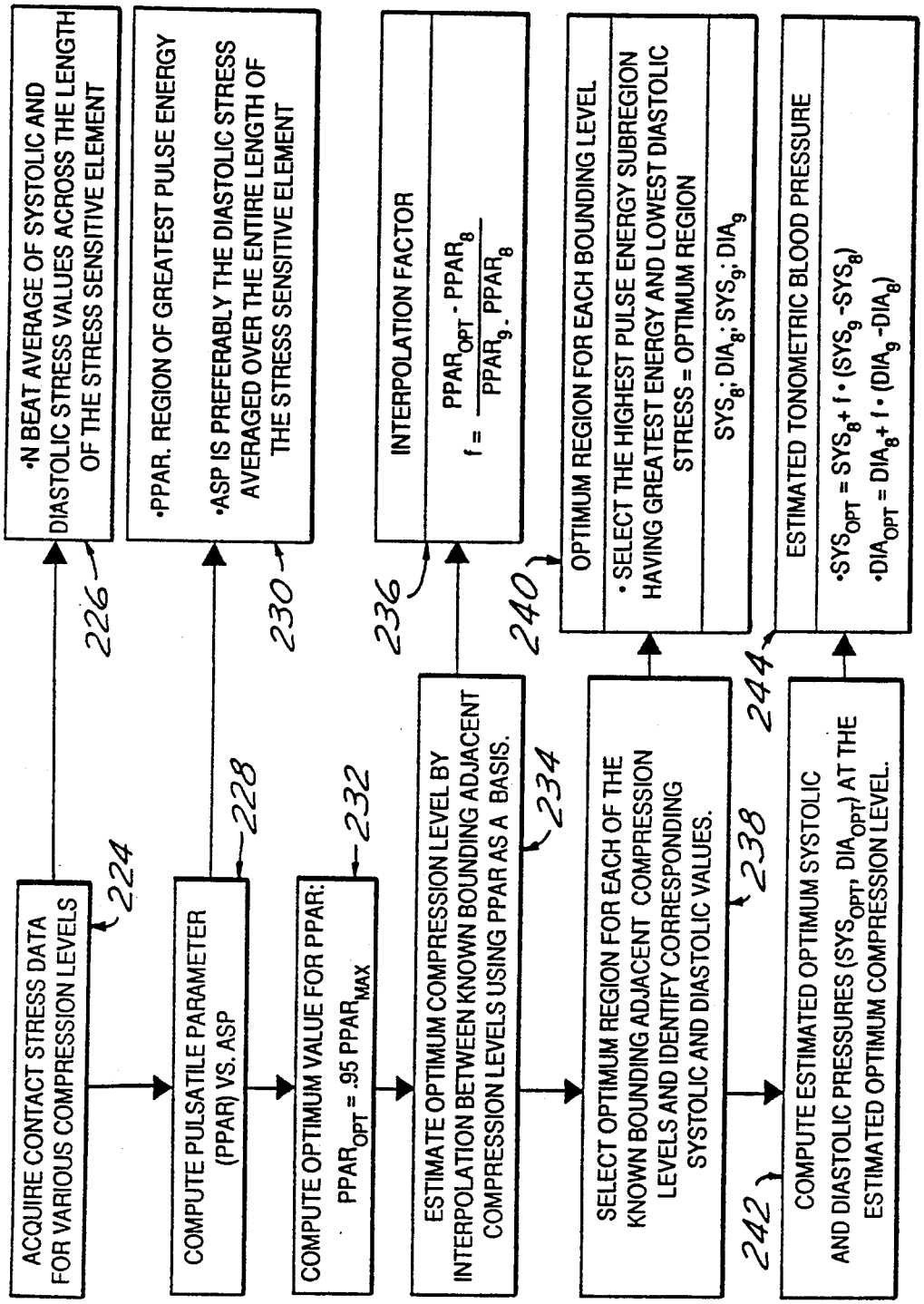
FIG. 18 is a flow diagram of selecting and interpolating arterial blood pressure values from contact stress data.

Now referring to FIGS. 15, 17, and 18, firstly, as has already been discussed in conjunction with Method 1, contact stress data must be acquired for various compression levels over the entire length of the stress sensitive element 224, 226. For a given compression level and a given portion along the length of the stress sensitive element, systolic and diastolic stresses are collected over a pre-determined number of heart beats 226. Next, the PPAR is computed 228 as a function of a selected ASP. A preferred ASP to be used with the PPAR parameter is the diastolic stress averaged over the entire length of the stress sensitive element 230 (see Section C under the earlier disclosed Section entitled, Preferred Applanation State Parameters). Next, the PPAR is computed and optimized 232, and if $PPAR_{OPT}$ falls between two applanation states 220, 222 (as shown in FIG. 17), an interpolation factor 236 is computed as follows:

$$f = \frac{PPAR_{OPT} - PPAR_8}{PPAR_9 - PPAR_8}$$

Once interpolation factor 236 is computed, the selected optimum region 208, 208' for each of the known bounding adjacent compression levels is selected and the corresponding systolic 216, 216' and diastolic 214, 214' values are computed as has already been disclosed in conjunction with Estimating Technique A. Finally, the optimum systolic 246 and diastolic 248 pressures are estimated at the estimated optimum compression level 242 by applying the following formula:

$$SYS_{OPT} = SYS_8 + f \cdot (SYS_9 - SYS_8)$$

$$DIA_{OPT} = DIA_8 + f \cdot (DIA_9 - SDI_8)$$

INTERPOLATION TECHNIQUE B

Figure 19:
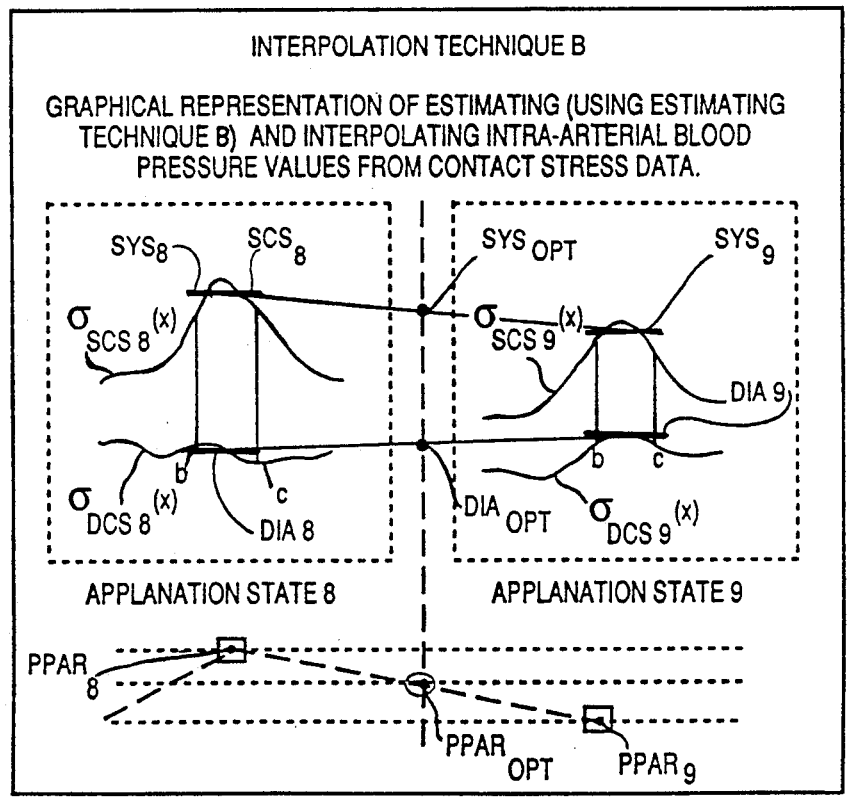
FIG. 19 is a graphical representation of interpolation technique B depicting interpolating arterial blood pressure values from contact stress data.

Now referring to FIGS. 16, 18, and 19, Interpolation Technique B is completely analogous to Interpolation Technique A, the only point of difference being that methodology 238, 240 shown in the flow diagram of FIG. 18 is altered to reflect the application of Estimating Technique B which has already been discussed in detail under the Section of this disclosure entitled Technique B. Specifically, instead of selecting the highest pulse energy subregion having the greatest energy and lowest diastolic stress 240, Interpolation Technique B calls for determining points 216, 216', 214, 214' by computing the average systolic and diastolic stress over the interval bounded by b, c. With the exception of replacing Estimating Technique A with Estimating Technique B, Interpolation Technique B is used and applied identically to the teaching of Estimating Technique A.

Although Interpolation Techniques A and B have been presented in the context of Estimating intra-arterial blood pressure after applying the optimization methodology of Method 1, they are equally applicable to optimization methodologies 2–12 and their application to those methodologies is directly analogous to that which has been shown in connection with Method 1 (the optimization of PPAR parameter). For that reason, the application of Interpolation Techniques A and B will not be detailed in conjunction with the disclosure of methodologies 2–12.

SUMMARY OF METHOD 1

$$AOP\!:\, PPAR = \frac{1}{c-b} \int_b^c \sigma_{PCS}(x) \cdot dx$$

Preferred $ASP$: $\sigma_{DCSAVG} = \frac{1}{L} \int_0^L \sigma_{DCS}(x) \cdot dx$ Optimization Rule: $PPAR_{OPT} = PPAR_{MAX} \times .95$ AOP Definition: The PPAR is defined as the average pulse stress occurring in a region (or multiple non-contigous regions) of the stress sensitive element selected as having the greatest pulse energy content.

The Theory Behind the Method: At a slightly reduced applanation state than that which causes $PPAR_{MAX}$, localized arterial wall collapses occurs due to an imbalance between internal arterial pressures and external arterial pressures. The optimum fraction is statistically determined from test data.

Method Steps:
1. Using the arterial applanation control mechanism to adjust the state of applanation through a broad range of applanation states, and acquiring contact stress data (spatially distributed across the length of the stress sensitive element) at each applanation state.
2. For each applanation state, computing PPAR and ASP.
3. Creating a function wherein PPAR (ASP).
4. Determining the optimum applanation state as defined by that value of ASP which corresponds to:

$$PPAR_{OPT} = PPAR_{MAX} \times 0.95$$

DETAILED DISCUSSION OF METHOD 2

This method utilizes the Mean Distribution Breadth Parameter (MDBP) to determine the optimum applanation state of the artery of interest. The Mean Distribution Breadth Parameter is a measure of the waveform mean stress distribution profile over the length of the stress sensitive element (normalized to the most pulsatily energetic regions) of the stress sensitive element. It is defined as the ratio of the spatial average waveform mean stress over the entire length of the stress sensitive element to the spatial average waveform mean stress occurring in a region (or multiple non-contiguous regions) of the stress sensitive element selected as having the greatest pulse energy content.

Figure 20:
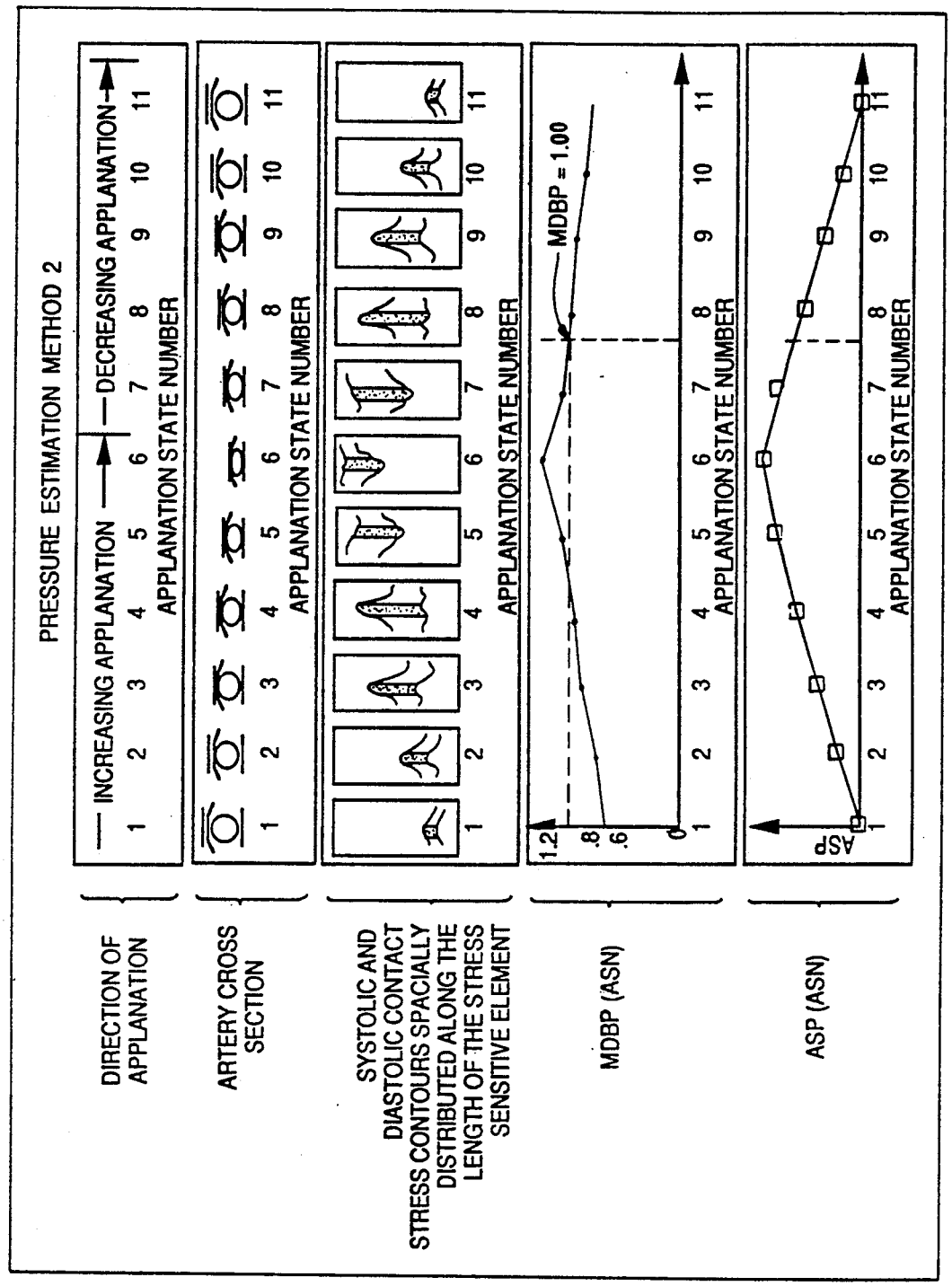
FIG. 20 is a diagrammatic and graphic representation of the method steps of Method 2 utilized in generating the MDBP parameter as a function of ASP.
Figure 21:
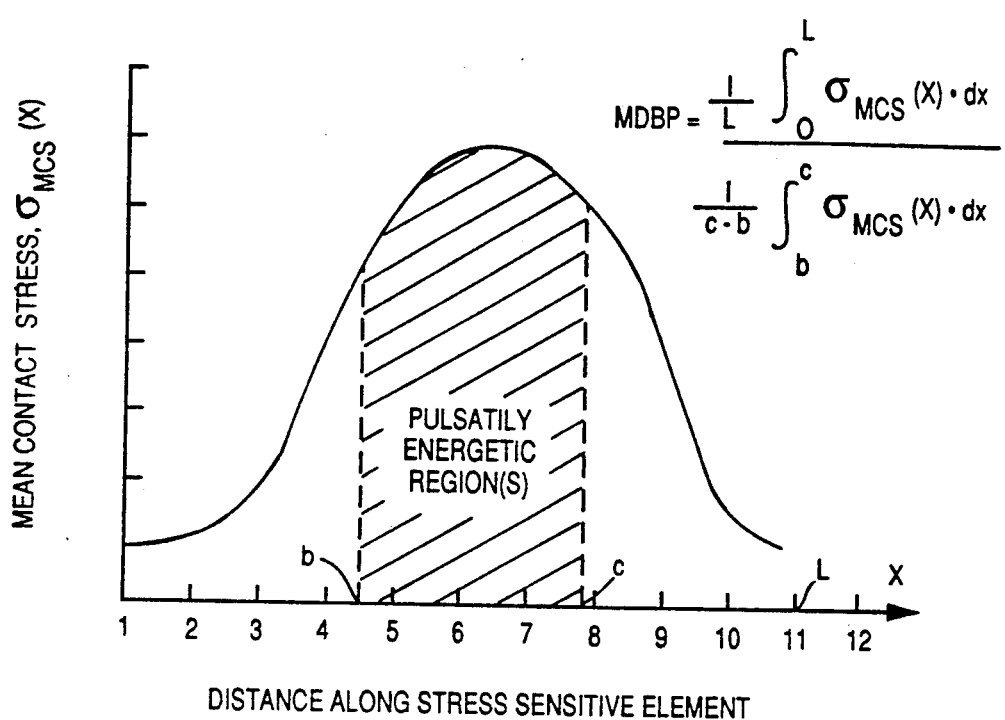
FIG. 21 is a graphical representation showing the calculation of the MDBP parameter as a function of a given applanation state.

Under Method 2, the optimum value occurs when MDBP is equal to approximately 1. Preferably, the exact optimum value to use is statistically determined from actual test data in which tonometric versus automatic cuff or invasive blood pressure values are correlated. FIGS. 20 and 21 will now be used to explain the implementation of Method 2.

Now referring to FIGS. 20 and 21, by using means 29 (see FIG. 2) for moving tissue stress sensor 20, the applanation state of artery 26 is changed through a broad range while acquiring contact stress data (spatially distributed across the length of stress sensitive element 34) at each applanation state. Next, for each applanation state, the mean distribution breadth parameter (MDBP) is computed according to the following formula:

$$MDBP = \frac{\frac{1}{L} \int_0^L \sigma_{MCS}(x) \cdot dx}{\frac{1}{c-b} \int_b^c \sigma_{MCS}(x) \cdot dx}$$

where $\sigma_{MCS}(x)$ is the mean contact stress averaged over n heartbeats and is calculated according to the following formula:

$$\sigma_{MCS}(x) = \frac{\int_{t_1}^{t_1 + n\tau} \sigma(x, t) \cdot dt}{\int_{t_1}^{t_1 + n\tau} dt}$$

where:
$\tau$ = time period of one heartbeat
n = the number of heartbeats selected for time averaging Next, a function is created of MDBP versus a preferred ASP. A preferred ASP for this method is the diastolic contact stress averaged over the entire length of the stress sensitive element. Mathematically, this ASP is computed as follows:

$$\sigma_{DCSAVG} = \frac{1}{L} \int_0^L \sigma_{DCS}(x) \cdot dx$$

Finally, the function MDBP(ASP), is used to find the optimum applanation state which corresponds to MDBP approximately equal to one.

SUMMARY OF METHOD 2

$$AOP: MDBP = \frac{\frac{1}{L} \int_0^L \sigma_{MCS}(x) \cdot dx}{\frac{1}{c-b} \int_b^c \sigma_{MCS}(x) \cdot dx}$$

$$\text{Preferred } ASP: \sigma_{DCSAVG} = \frac{1}{L} \int_0^L \sigma_{DCS}(x) \cdot dx$$

where $\sigma_{MCS}(x)$ is the mean contact stress averaged over n heartbeats and is calculated according to the following formula:

$$\sigma_{MCS}(x) = \frac{\int_{t_1}^{t_1 + n\tau} \sigma(x, t) \cdot dt}{\int_{t_1}^{t_1 + n\tau} dt}$$

where:
$\tau$ = time period of one heartbeat
n = the number of heartbeats selected for time averaging Optimization Rule: MDBP approximately equal to one.

AOP Definition: MDBP is the ratio of the spatial average waveform mean stress over the entire length of the stress sensitive element to the spatial average waveform mean stress occurring in a region (or multiple non-contiguous regions) of the stress sensitive element selected as having the greatest pulse energy content.

Theory behind the Method: Conditions exist for localized vessel wall collapse due to external versus internal pressure imbalance when mean stresses neighboring the artery are approximately equal to mean stresses over the artery. The optimum value of MDBP is statistically determined from actual test data.

Method Steps:
1. Using the vessel applanation control mechanism to adjust the state of arterial applanation through a broad range of applanation states while acquiring contact stress data (spatially distributed across the length of the stress sensitive element) at each applanation state.
2. For each applanation state, computing MDBP and ASP.
3. Creating a function wherein MDBP(ASP).
4. Determining the optimum applanation state as defined by that value of ASP which corresponds to MDBP = 1.00.

DETAILED DISCUSSION OF METHOD 3

This method utilizes the Diastolic Distribution Breadth Parameter (DDBP) to determine the optimum applanation state of the artery of interest. The Diastolic Distribution Breadth Parameter DDBP is defined as the ratio of the average diastolic stress over the entire length of the stress sensitive element to the average diastolic stress occurring in a region (or multiple non-contiguous regions) of the stress sensitive element selected as having the greatest pulse energy content. The DDBP parameter can be generally thought of as describing the ratio between representative diastolic stresses in the pulsatily inactive region of the stress sensitive element versus the diastolic stresses in the pulsatily active regions of the stress sensitive element. Mathematically DDBP is expressed as follows:

$$DDBP = \frac{\frac{1}{L}\int_0^L \sigma_{DCS}(x) \cdot dx}{\frac{1}{c-b}\int_b^c \sigma_{DCS}(x) \cdot dx}$$

where:
L = length of stress sensitive element
b, c = limits of integration
x = distance along length of stress sensitive element
$\sigma_{DCS}(x)$ = diastolic contact stress as a function of x The graphic illustration of the calculation of DDBP (for a given applanation state) is shown in FIG. 22.

Figure 22:
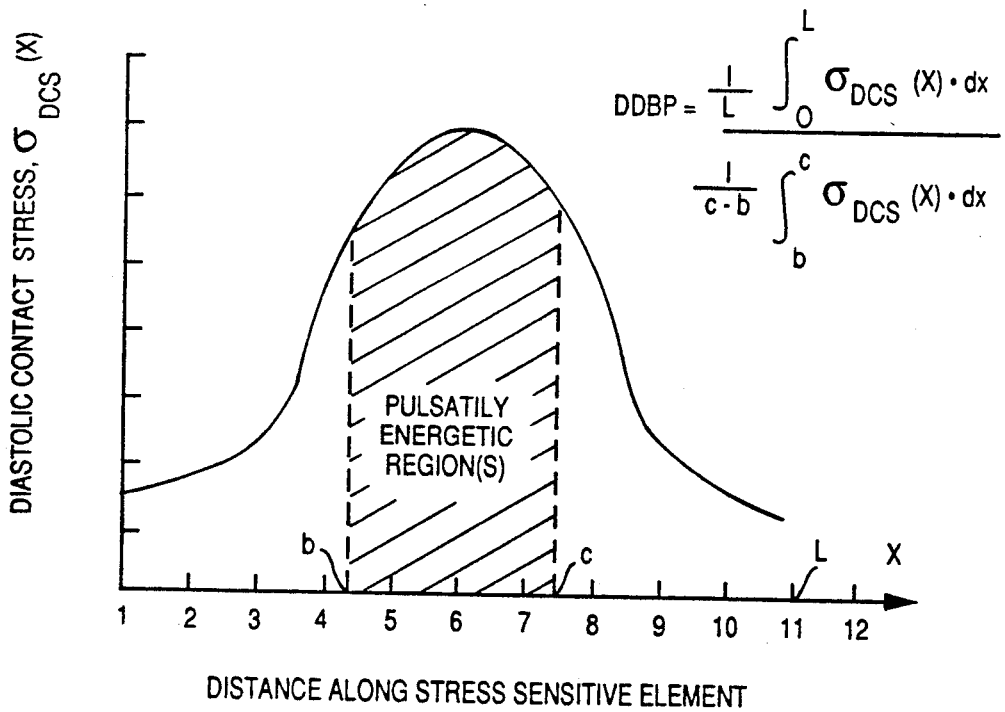
FIG. 22 is a graphical representation showing the calculation of the DDBP parameter for a given applanation state.
Figure 23:
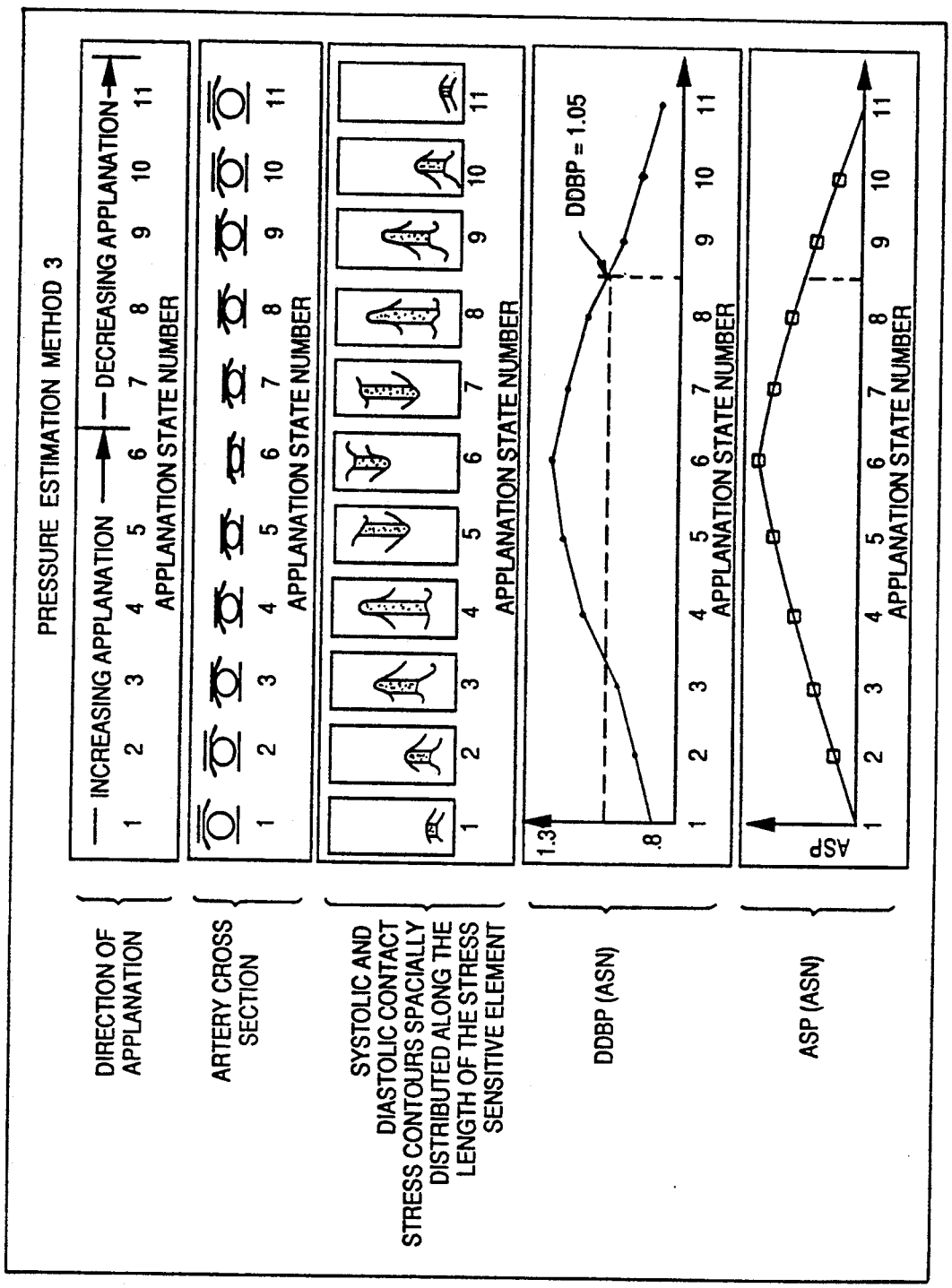
FIG. 23 is a diagrammatic and graphic representation of the method steps of Method 3 utilized in generating the DDBP parameter as a function of ASP.

Now referring to FIGS. 22 and 23, the optimum value of DDBP occurs when DDBP equals 1.05. Of course, as we have discussed in the earlier Methods, the value to be used in indicating the optimum applanation state, is preferably statistically determined by comparing tonometry data and actual intra-arterial blood pressure data.

Method 3 is conducted as follows. First, using the arterial applanation control mechanism, the applanation state of artery 26 (see FIG. 2) is changed through a broad range of applanation states while acquiring contact stress data (spatially distributed across the stress sensitive element 32) at each applanation state. Next, for each applanation state, the DDBP is calculated along with a preferred ASP. A special function is created wherein DDBP is a function of the selected ASP. The optimum applanation point occurs when DDBP equals approximately 1.05, from the function DDBP (ASP) the optimum value of the ASP corresponding to DDBP = 1.05 is determined.

The preferred ASP to use in Method 3 is the average diastolic contact stress calculated as follows:

$$\sigma_{DCSAVG} = \frac{1}{L}\int_0^L \sigma_{DCS}(x) \cdot dx$$

where:
$\sigma_{DCSAVG}$ = average diastolic stress across the length of the stress sensitive element.
L = length of stress sensitive element
x = location along the stress sensitive element
$\sigma_{DCS}(x)$ = diastolic contact stress as a function of x

SUMMARY OF METHOD 3

$$AOP: DDBP = \frac{\frac{1}{L}\int_0^L \sigma_{DCS}(x) \cdot dx}{\frac{1}{c-b}\int_b^c \sigma_{DCS}(x) \cdot dx}$$

Preferred $ASP: \sigma_{DCSAVG} = \frac{1}{L}\int_0^L \sigma_{DCS}(x) \cdot dx$

Optimization Rule: DDBP = 1.05

AOP Definition: The DDBP is defined as the ratio of the average diastolic stress over the entire length of the stress sensitive element to the average diastolic stress occurring in a region (or multiple non-contiguous regions) of the stress sensitive element selected as having the greatest pulse energy content.

Theory Behind the Method: Conditions exist for localized arterial wall collapse due to external versus internal pressure imbalance when the diastolic stresses neighboring the artery are slightly greater than the diastolic stresses over the artery (e.g. approximately 1.05). The optimum value of DDBP is to be statistically determined from actual test data.

Method Steps:
1. Using the arterial applanation control mechanism to adjust the state of arterial applanation through a broad range of applanation states while acquiring contact stress data (spatially distributed across the length of the stress sensitive element) at each applanation state.
2. For each applanation state, computing the Diastolic Distribution Breadth Parameter DDBP and ASP.
3. Creating a function wherein DDBP(ASP).
4. Determining the optimum applanation state as defined by that value of ASP which corresponds to DDBP = 1.05

DETAILED DISCUSSION OF METHOD 4

This method utilizes the Pulse Distribution Breadth Parameter (PDBP) to determine the optimum applanation state of the artery of interest. The PDBP is defined as the number of sampling locations along the stress sensitive element (or cumulative amount of stress sensitive element length) sensing normalized pulse stress values greater than some selected threshold value. The PDBP is a measure of the spatial uniformity of the pulse stress distribution profile over the length of the stress sensitive element. It is an indication of the broadening out or widening of the pulsatily active regions of the stress sensitive element with increasing applanation. A graphical representation of the method of calculating the PDBP parameter is graphically illustrated in FIG. 25.

Mathematically, PDBP is defined as follows:

$$PDBP = \int_b^c dx = W_{TH}$$

where:
$W_{TH}$ = cumulative width at $\sigma_{PCSTHR}$
$\sigma_{PCSTHR}$ = predetermined threshold value of pulsatile contact stress Method 4 estimates the optimum applanation state of the artery of interest by assuming that the optimum value of the applanation state parameter occurs at the mid-point in the range of the maximum value of the pulsatile distribution breadth parameter PDBP (considering only vessel compression levels at or below the level producing the maximum value in the pulsatile parameter (PPAR$_{MAX}$)). A variation of this method considers that several versions of PDBP can be computed and used in which the optimum value of the applanation state parameter is a composite of the optimum values of the ASP for each of the several versions of PDBP. The composite optimum value of ASP is computed by a centroidal location method using location of individual optimum ASP values in the computation. Various weighting factors can also be used in a further variation (the selection of which is statistically determined from actual tonometer tests in which tonometer versus automatic cuff or invasive blood pressures are correlated). The approach which results in the best correlation is preferably used for the basis of selecting the best weighting factors. The implementation of Method 4 will now be discussed in conjunction with FIGS. 24 and 25.

Figure 24:
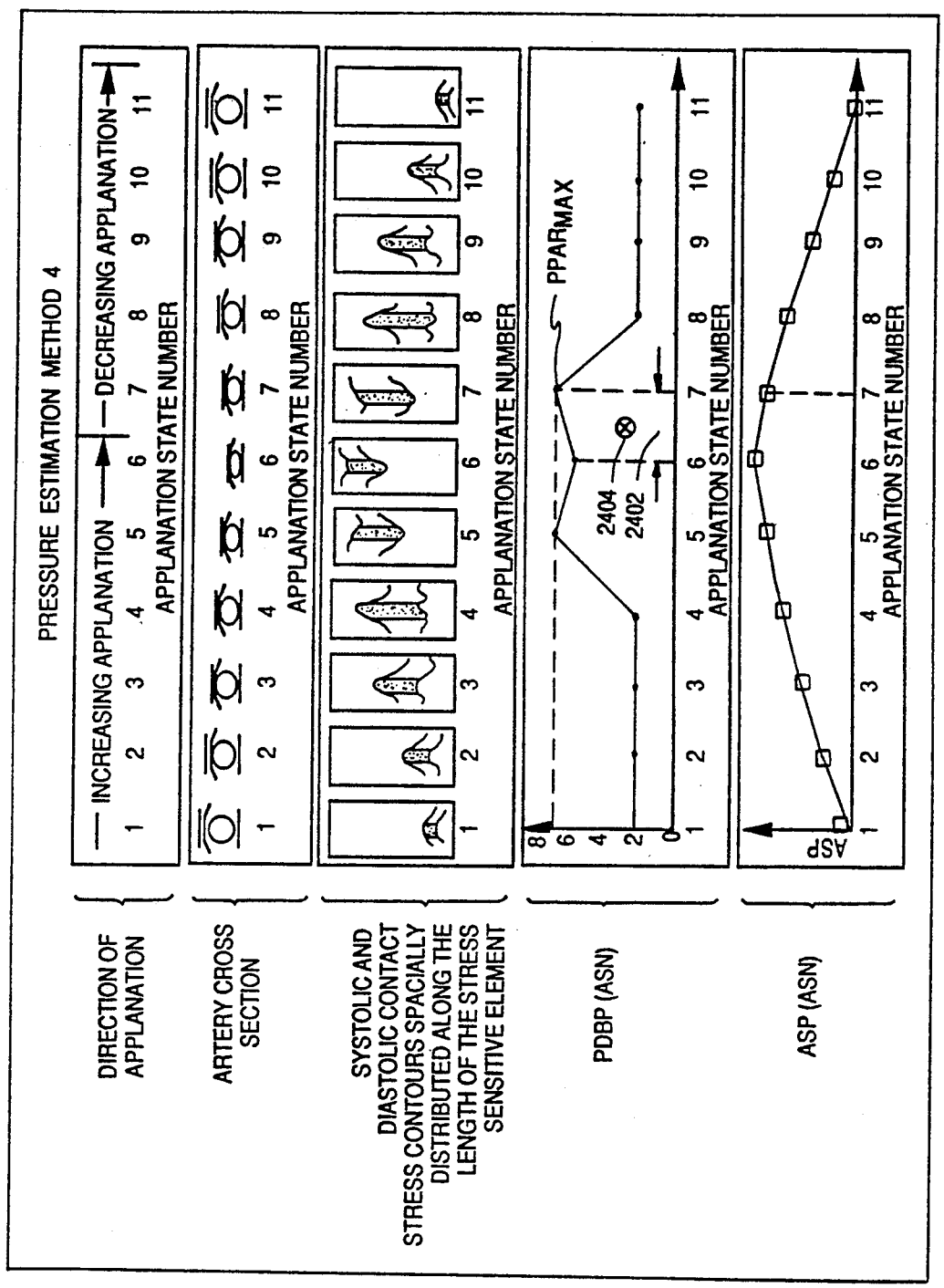
FIG. 24 is a diagrammatic and graphical representation of the method steps of Method 4 utilized in generating the PDBP parameter as a function of ASP.
Figure 25:
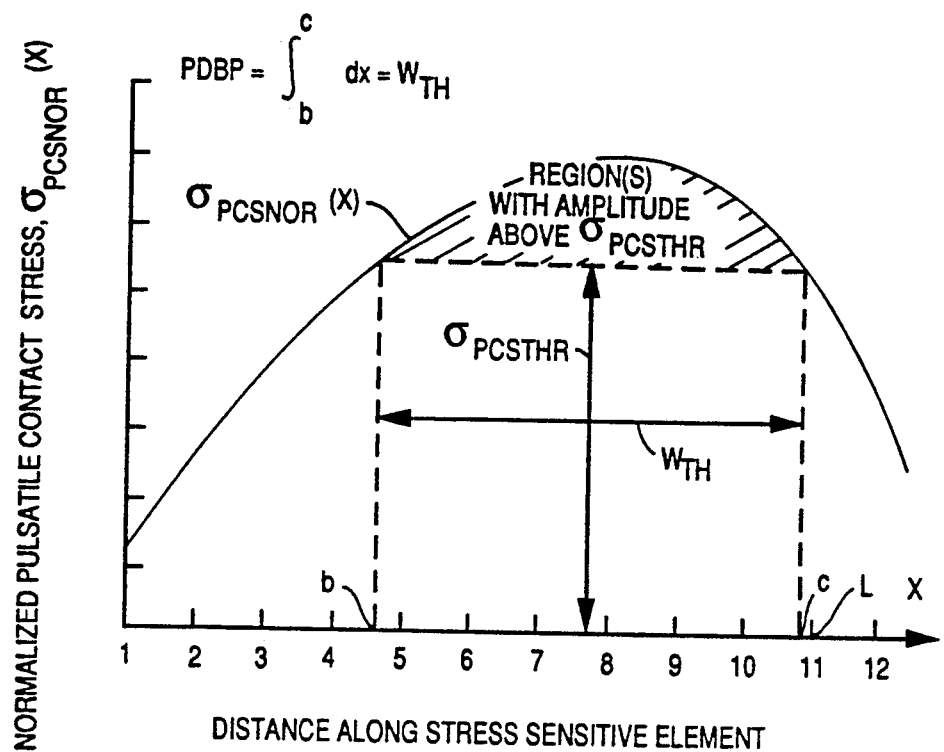
FIGS. 25 and 26 are identical graphical representations showing the calculation of the PDBP parameter for a given applanation state.

Now referring to FIGS. 24 and 25, when implementing Method 4, first the artery applanation control mechanism is used to adjust the applanation state of artery 26 through a broad range of applanation states while acquiring contact stress data (spatially distributed across the length of the stress sensitive element 32) at each applanation state. Then, for each applanation state, the PDBP and ASP are calculated. The preferred ASP for use in Method 4 is mean diastolic stress, computed as follows:

$$\sigma_{DCSAVG} = \frac{1}{L} \int_0^L \sigma_{DCS}(x) \cdot dx$$

where:

$\sigma_{DCSAVG}$=average diastolic stress across the length of the stress sensitive element.
L=length of stress sensitive element
x=location along the stress sensitive element
$\sigma_{DCS}(x)$=diastolic contact stress as a function of x Next, a special function is created PDBP(ASP) between PDBP and ASP. Then, a range of applanation state parameter values is established 2402 encompassing the region or plateau of maximum PDBP (occurring at applanation states with less applanation than that for PPAR$_{MAX}$). Then, defining a mid-point 2404 in the range of applanation state parameter values established in the previous step. Next, consider that the optimum applanation state parameter occurs at the mid-point ASP value established in the previous step. The above referenced methodology can be used using several versions of PDBP (each having a different threshold value for computation). The overall optimum applanation state parameter is the combined result of the individually computed optimum ASP values.

SUMMARY OF METHOD 4

$$AOP: PDBP = \int_b^c dx = W_{TH}$$

where:

W$_{TH}$=cumulative width at $\sigma_{PCSTHR}$ $\sigma_{PCSTHR}$=predetermined threshold value of pulsatile contact stress $$\text{Preferred } ASP: \sigma_{DCSAVG} = \frac{1}{L} \int_0^L \sigma_{DCS}(x) \cdot dx$$

where:

$\sigma_{DCSAVG}$=average diastolic stress across the length of the stress sensitive element.
L=length of stress sensitive element
x=location along the stress sensitive element
$\sigma_{DCS}(x)$=diastolic contact stress as a function of x
Optimization Rule: PDBP$_{OPT}$=PDBP$_{mid-point}$ AOP Definition: The PDBP parameter is defined as the cumulative width W$_{TH}$ in a region (or multiple non-contiguous regions) above a predetermined pulsatile contact stress threshold value.

Theory Behind the Method: Applanation state parameter is optimum at the mid-point in the range of the maximum value of the PDBP (considering only the range of applanation levels below that for which PPAR$_{MAX}$ occurs). Mid-point in PDBP maximum plateau range occurs with localized vessel wall collapse due to localized internal versus external pressure balance.

Method Steps:

1. Using the vessel applanation control mechanism, adjust the state of applanation through a broad range while acquiring contact stress (spatial distribution) data at various applanation states.

2. At each applanation state, computing the pulse distribution breadth parameter (PDBP) and the applanation state parameter (ASP).

3. Creating a special function of the PDBP versus the ASP: PDBP(ASP).

4. Establishing a range of ASP values that encompass the region or plateau of maximum PDBP (occurring at applanation states with less applanation than that for PPAR$_{MAX}$).

5. Defining a mid-point in the range of ASP of values established in Step 4 above.

6. Considering that the optimum ASP occurs at the mid-point ASP value established in Step 5 above.

7. Considering the use of several versions of PDBP (each having a different threshold value for computation). The overall optimum ASP is the combined result of the individually computed optimum ASP values.

DETAILED DISCUSSION OF METHOD 5

This method compares incremental changes in the Pulse Distribution Breadth Parameter (for approximately equal changes or steps in ASP).

Figure 26:
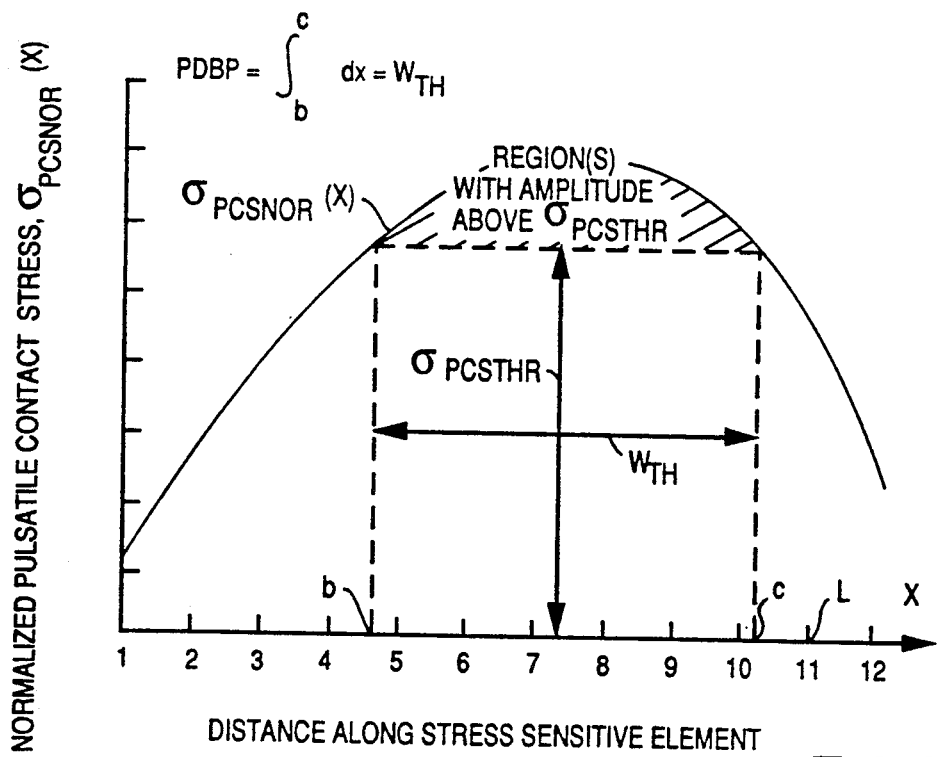
Figure 27:
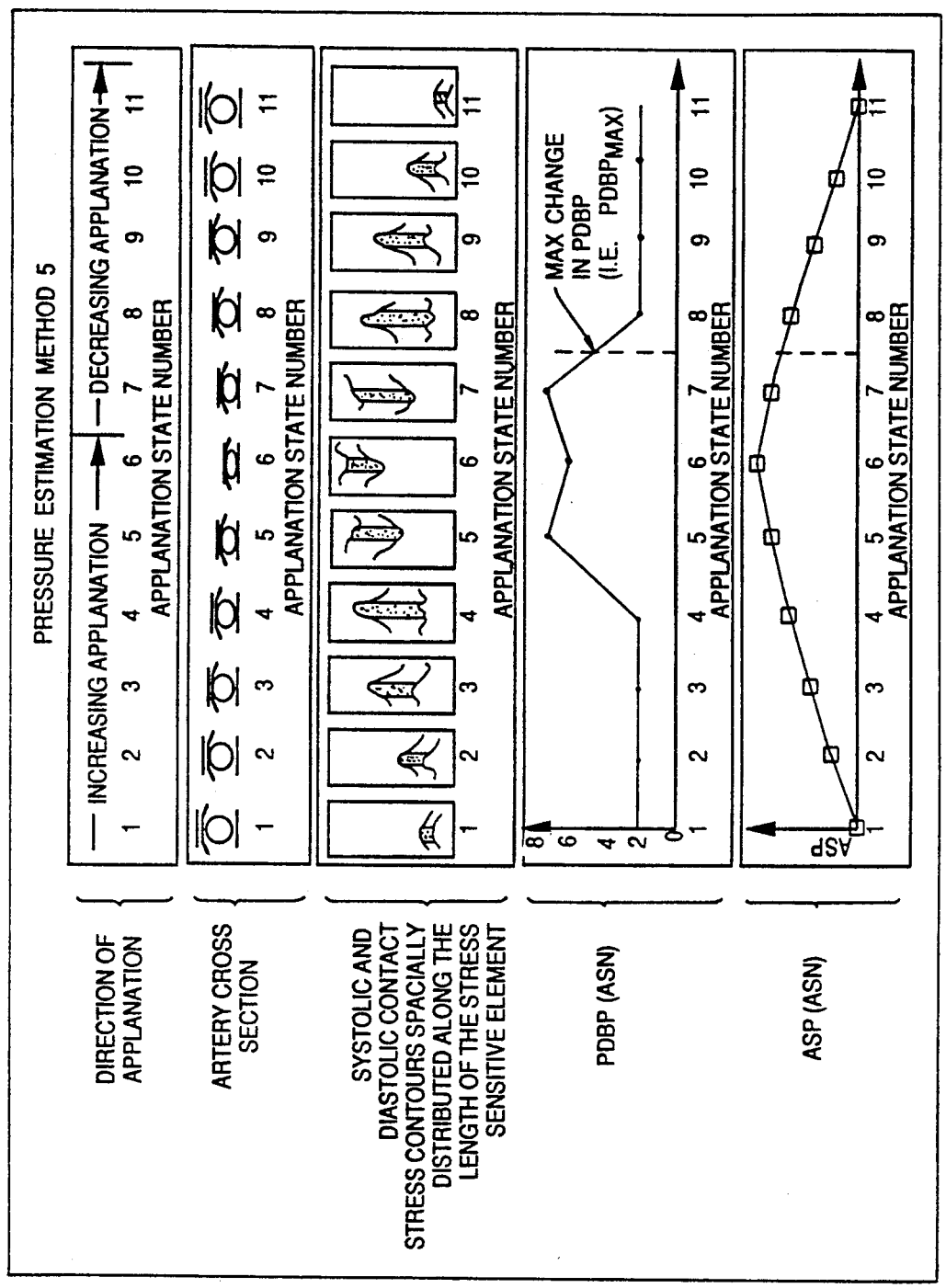
FIG. 27 is a diagrammatic and graphical representation of the method steps of Method 5 utilized in generating the Δ PDBP parameter as a function of ASP.

The Pulse Distribution Breadth Parameter (PDBP) is a measure of the spatial uniformity of the pulse stress distribution profile over the length of the stress sensitive element. It is defined as a number of sampling locations along the stress sensitive element (or cumulative amount of length along the stress sensitive element) having normalized pulse stress values greater than some selected threshold value. It is an indication of the broadening out or widening of the pulsatively active regions of the stress sensitive element with increasing applanation. The graphic illustration of the calculation of PDBP (for a given applanation state) is shown in FIG. 26. Mathematically, PDBP is defined as follows:

$$PDBP = \int_b^c dx = W_{TH}$$

where:

$W_{TH}$ = cumulative width at $\sigma_{PCSTHR}$ $\sigma_{PCSTHR}$ = predetermined threshold value of pulsatile contact stress Now referring to FIGS. 26 and 27. In Method 5, the optimum value of the PDBP parameter occurs when the incremental change $\Delta$PDBP is a maximum assuming the range in applanation states has been covered with approximately equal applanation increments or steps. The applanation state range of interests lies at less applanation than that when the pulsatile parameter PPAR is a maximum. Mathematically, $\Delta$PDBP is calculated as follows:

$$\Delta PDBP(i) = W_{TH}(i) - W_{TH}(i+1)$$

where:

$\Delta$PDBP(i) = change in pulse distribution breadth parameter for the ith applanation state $W_{TH}(i)$ = cumulative width at $\sigma_{PCSTHR}$ for the ith applanation state $W_{TH}(i+1)$ = cumulative width at $\sigma_{PCSTHR}$ for the i+1 applanation state i = a given applanation state The implementation of Method 5 will now be discussed in conjunction with FIGS. 26 and 27.

Now referring to FIGS. 26 and 27, when implementing Method 5, first the artery applanation control mechanism is used to adjust the applanation state of artery 26 to a broad range of applanation states while acquiring contact stress data (spatially distributed across the length of the stress sensitive element 32) at each applanation state. For each applanation state, the PDBP is calculated along with a preferred ASP. A special function is created wherein PDBP is a function of the preferred ASP. Next, a special function $\Delta$PDBP(ASP) is created. The optimum applanation point occurs when $\Delta$PDBP is maximum. From the function $\Delta$PDBP(ASP), find the optimum value of the ASP corresponding to:

$$\Delta PDBP_{OPT} = \Delta PDBP_{MAX}$$

A preferred mode of calculating the $\Delta$PDBP parameter involves implementing a criteria for ignoring $\Delta$PDBP calculations which are conducted at high applanation states and low applanation states. By ignoring $\Delta$PDBP values at these extreme states, it has been found that more reliable predictions of optimum applanation state are possible. Implementing this type of high/low criteria is not only preferable in Method 5, but is also preferable in any of the following methods (Method 6-11) which employ the use of a difference (or delta $\Delta$) function, a first derivative function, or a second derivative function.

SUMMARY OF METHOD 5

$$AOP: PDBP = \int_b^c dx = W_{TH}$$

where:

$W_{TH}$ = cumulative width at $\sigma_{PCSTHR}$ $\sigma_{PCSTHR}$ = predetermined threshold value of pulsatile contact stress $$\text{Preferred } ASP: \sigma_{DCSAVG} = \frac{1}{L} \int_0^L \sigma_{DCS}(x) \cdot dx$$

where:

$\sigma_{DCSAVG}$ = average diastolic stress across the length of the stress sensitive element.

L = length of stress sensitive element x = location along the stress sensitive element $\sigma_{DCS}(x)$ = diastolic contact stress as a function of x Optimization Rule: $\Delta$PDBP = MAXIMUM AOP Definition: $\Delta$PDBP is defined as a measurement of incremental changes in the PDBP for approximate equal changes or steps in the ASP. PDBP is a measure of the spatial uniformity of the pulse distribution profile over the length of the stress sensitive element. It is defined as the number of sampling locations along the stress sensitive element (or cumulative amount of stress sensitive element length) having normalized pulse stress values greater than some selected threshold value.

Theory Behind the Method: The optimum value of the applanation parameter occurs when the increment change $\Delta$PDBP is a maximum assuming the range in applanation state has been covered with approximately equal applanation increments. The largest value of the change in $\Delta$PDBP occurs with localized vessel wall collapse due to localized internal versus external pressure balance.

Method Steps:

1. Using the vessel applanation control mechanism, adjusting the state of applanation through a broad range while acquiring contact stress (spatial distribution) data at various applanation states. Acquiring data at roughly equal steps or increments in applanation state.

2. At each applanation state, computing the PDBP, the change in the PDBP, $\Delta$PDBP, and the ASP.

3. Create a special function of the change in PDBP $\Delta$PDBP versus the ASP: $\Delta$PDBP(ASP).

4. Considering that the optimum applanation state occurs when $\Delta$PDBP is a maximum.

5. From the function $\Delta$PDBP(ASP), find the optimum value of the ASP corresponding to:

$$\Delta PDBP_{OPT} = \Delta PDBP_{MAX}$$

DETAILED DISCUSSION OF METHOD 6

This method utilizes the Pulse Spread Parameter (PSP) to determine the optimum applanation state of the artery of interest. The PSP is defined as the maximum spread (or deviation) in pulse stress occurring in a region (or multiple non-contiguous regions) of the stress sensitive element selected as having the greatest pulse energy content. A graphical representation of the method of calculating PSP for a given applanation state is disclosed in FIG. 29. Mathematically, PSP is defined as follows:

$$PSP = \sigma_{PCSMAX} - \sigma_{PCSENG}$$

where $\sigma_{PCSENG}$ is set equal to either $\sigma_{PCSb}$ or $\sigma_{PCSc}$, which ever is the lesser.

Method 6 estimates the optimum applanation state of the artery of interest by computing the first derivative of PSP with respect to a selected ASP. Thus, when PSP'(ASP) is a maximum, the optimum arterial applanation state occurs. The first derivative operation will be represented hereinafter with an apostrophe after the function it relates to. For example, the first derivative of the PCP(ASP) function is represented as PSP'(ASP). Likewise, the second derivative will be represented with a double apostrophe PSP''(ASP). The implementation of Method 6 will now be discussed in conjunction with FIGS. 28 and 29.

Figure 28:
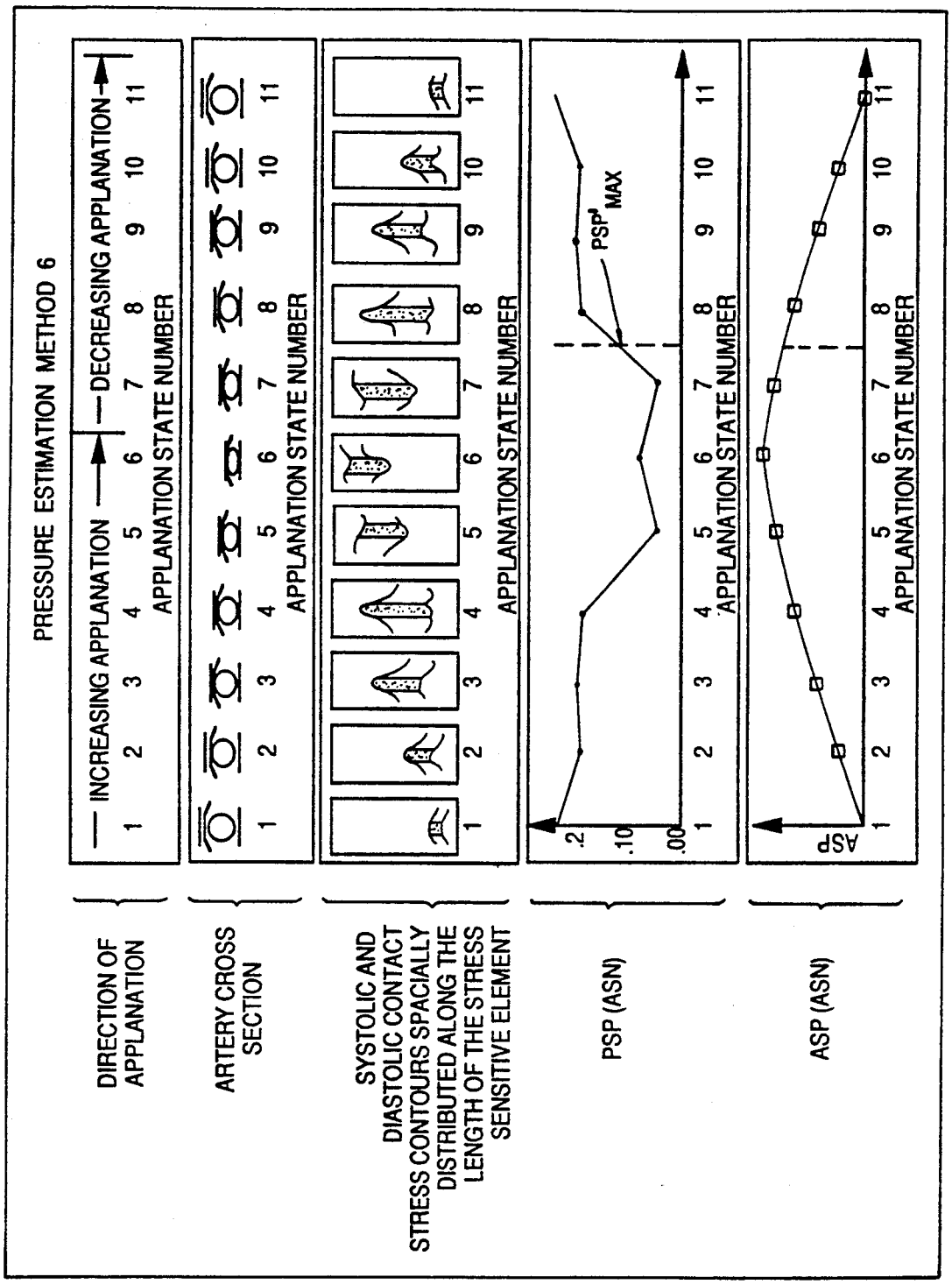
FIG. 28 is a diagrammatic and graphical representation of the method steps of Method 6 utilized in generating the PSP parameter as a function of ASP.
Figure 29:
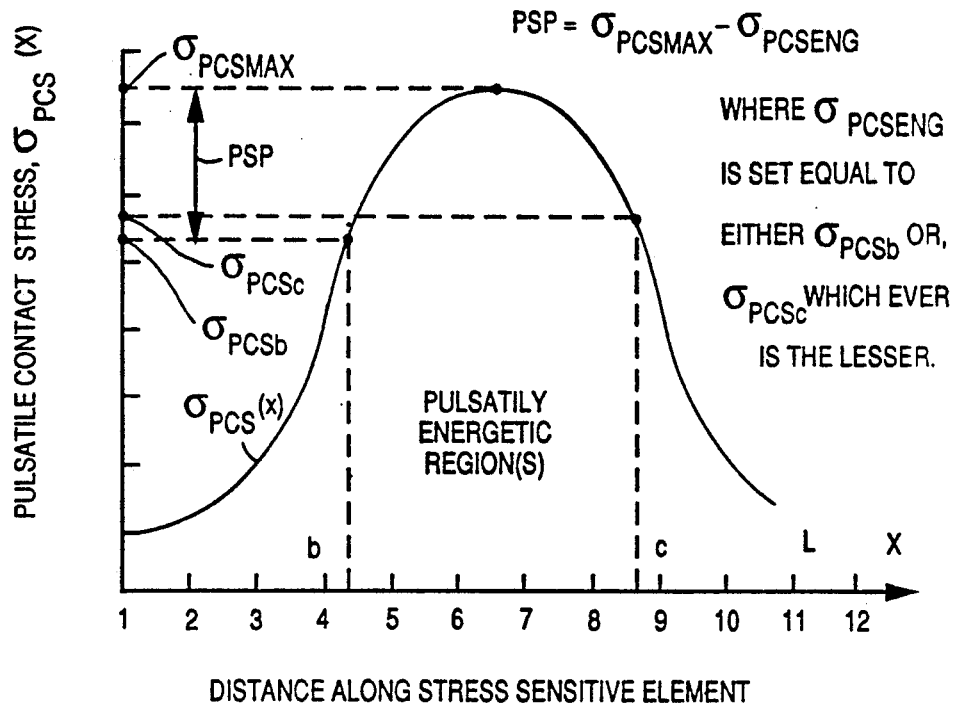
FIG. 29 is a graphical representation of the calculation of the PSP parameter for a given applanation state.

Now referring to FIGS. 28 and 29, when implementing Method 6, first the artery applanation control mechanism is used to adjust the applanation state of artery 26 through a broad range of applanation states while acquiring contact stress data (spatially distributed across the length of stress sensitive element 32) at each applanation state. Then, for each applanation state, the PSP and ASP are calculated. The preferred ASP for use in Method 6 is mean diastolic stress, computed as follows:

$$\sigma_{DCSAVG} = \frac{1}{L} \int_0^L \sigma_{DCS}(x) \cdot dx$$

Next, a function is created PSP(ASP) between PSP and ASP and a new function is computed PSP'(ASP). The optimum applanation state is defined to be that state of artery applanation which occurs when PSP'(ASP) is a maximum. From the function PSP'(ASP), the optimum value of the ASP is found according to the following formula:

$$PSP'_{OPT} = PSP'_{MAX}$$

SUMMARY OF METHOD 6

AOP: $PSP = \sigma_{PCSMAX} - \sigma_{PCSENG}$ where $\sigma_{PCSENG}$ equals either $\sigma_{PCSB}$ or $\sigma_{PCSC}$, whichever is the lesser.

Preferred ASP: $\sigma_{DCSAVG} = \frac{1}{L} \int_0^L \sigma_{DCS}(x) \cdot dx$ Optimization Rule: PSP' = a maximum.

AOP Definition: The pulse spread parameter is defined as the maximum spread (or deviation) in pulse stress occurring in a region (or multiple non-contiguous regions) of the stress sensitive element selected as having the greatest pulse energy content.

Theory Behind the Method: The largest value of PSP' occurs when the localized artery wall collapses due to an internal versus external pressure imbalance.

Method Steps:
1. Using the artery applanation control mechanism, the applanation state of artery 26 is changed over a broad range of arterial applanation states while acquiring contact stress data (spatially distributed across the length of stress sensitive element 32) at each applanation state.
2. For each applanation state, computing PSP and ASP.
3. Creating a function PSP(ASP), and from that function creating a second function PSP'(ASP).
4. Defining the optimum applanation state to occur when PSP' is a maximum.

5. Determining the optimum applanation state as defined by that value of ASP which corresponds to:

$$PSP'_{OPT} = PSP'_{MAX}$$

DETAILED DISCUSSION OF METHOD 7

This method utilizes the Pulse Distribution Breadth Parameter (PDBP) and compares the first derivative of PDBP with a selected Applanation State Parameter (ASP). The PDBP is defined as the number of sampling locations along the stress sensitive element (or cumulative amount of length along the stress sensitive element) having normalized pulse stress values $\sigma_{PCSNOR}(x)$ where, $$\sigma_{PCSNOR}(x) = \frac{\sigma_{PCS}(x)}{\sigma_{PCSMAX}}$$

greater than a preselected threshold value. PDBP is a measure of the spatial uniformity of the pulse stress distribution profile over the entire length of the stress sensitive element. It indicates the broadening out (or widening) of the pulsatily active regions of the diaphragm with change in applanation state. For a given applanation state, it is calculated according to the following formula:

$$PDBP = \int_b^c dx = W_{TH}$$

$\sigma_{PCS}(x)$ where:
$W_{TH}$ = cumulative width at threshold $\sigma_{PCSTHR}$ along normalized plot of pulsatile contact stress $\sigma_{PCSNOR}(x)$
b,c = limits of integration defined by 60% of $\sigma_{PCSMAX}$ The graphical illustration of calculating PDBP for a given applanation state is shown in FIG. 30.

The optimum value of the applanation state parameter occurs when the first derivative of PDBP is a maximum. The implementation of Method 7 will now be discussed in conjunction with FIGS. 30 and 31.

Figure 30:
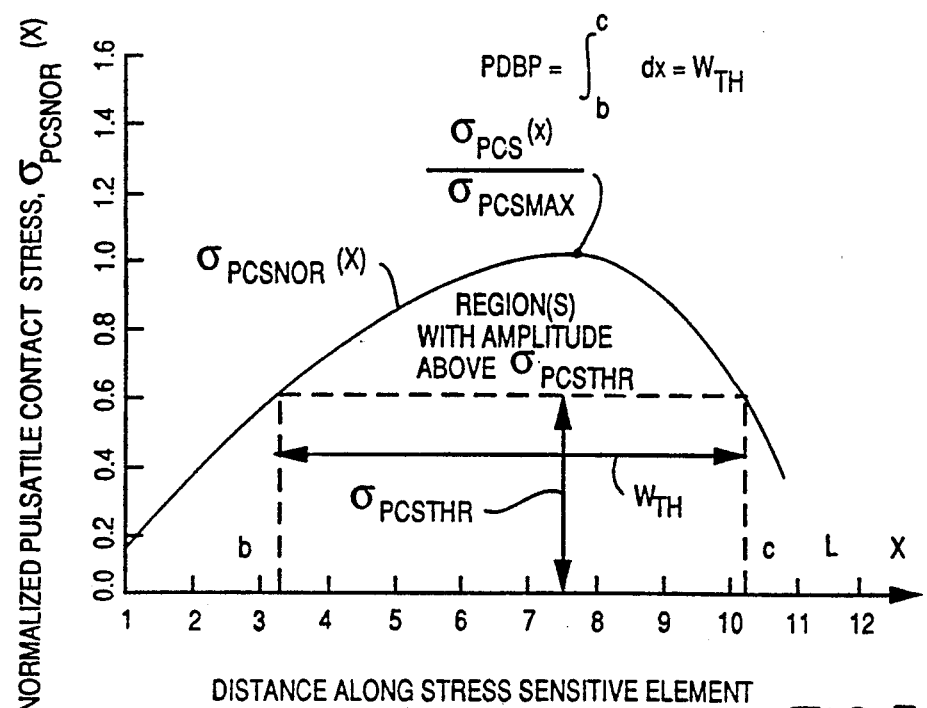
FIG. 30 is a graphical representation of the calculation of the PDBP parameter for a given applanation state.
Figure 31:
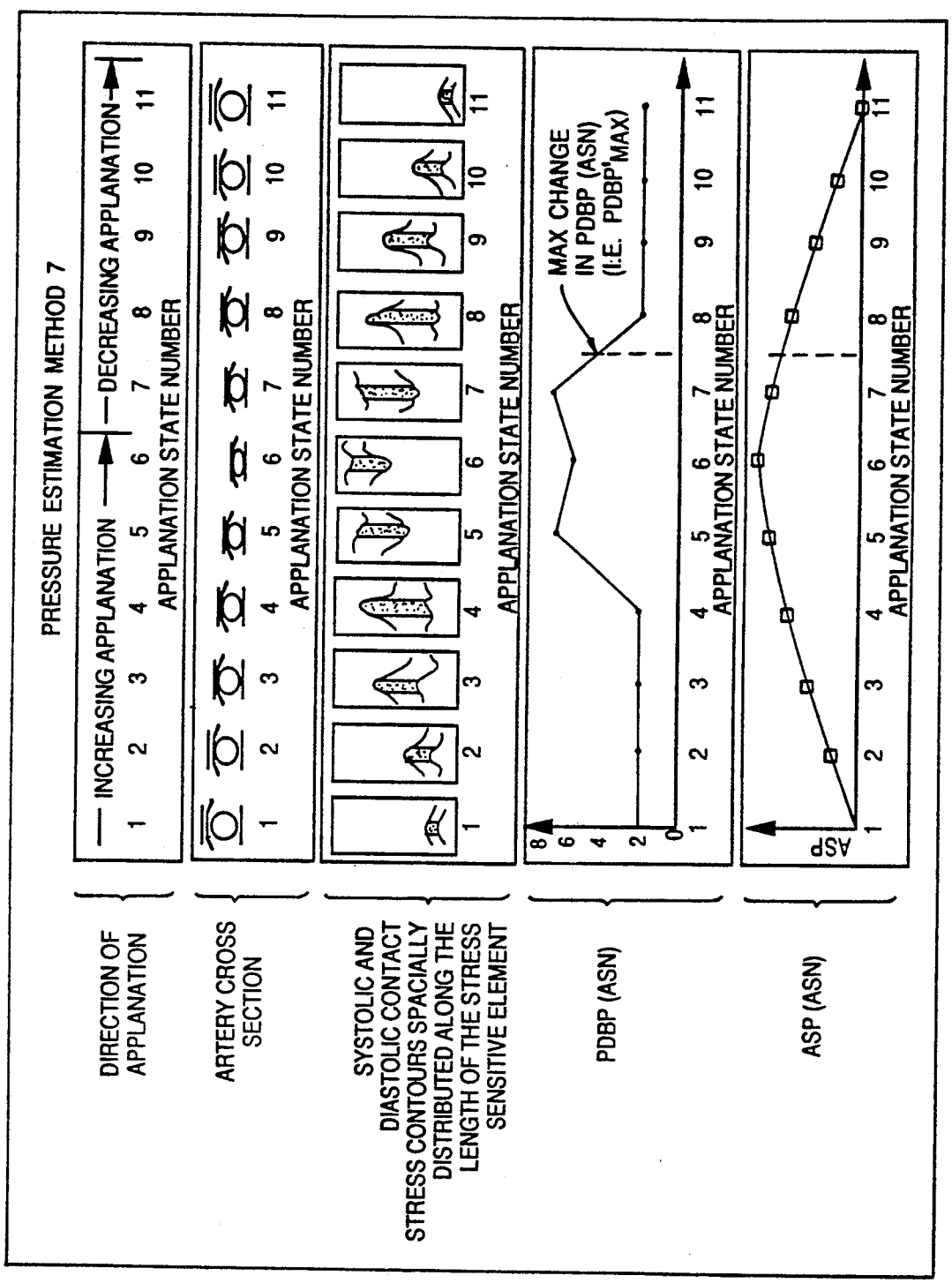
FIG. 31 is a diagrammatic and graphical representation of the method steps of Method 7 utilized in generating the PDBP parameter as a function of ASP.

Now referring to FIGS. 30 and 31, when implementing Method 7, first the artery applanation control mechanism is used to adjust the applanation state of artery 26 through a broad range of applanation states while acquiring contact stress data (spatially distributed across the length of stress sensitive element 32) at each applanation state. For each applanation state, the PDBP and ASP are calculated. The preferred ASP for use in Method 7 is mean diastolic stress computed as follows:

$$\sigma_{DCSAVG} = \frac{1}{L} \int_0^L \sigma_{DCS}(x) \cdot dx$$

Next, a special function is created between PDBP and ASP, PDBP(ASP). And a new function is computed PDBP'(ASP). The optimum applanation state is defined to be that state of artery applanation which occurs when PDBP'(ASP) is a maximum. Mathematically, this is expressed as follows:

$PDBP'_{OPT} = PDBP'_{MAX}$

SUMMARY OF METHOD 7

$$AOP: PDBP = \int_b^c dx = W_{TH}$$

where:

$W_{TH}$=cumulative width at threshold $\sigma_{PCSTHR}$ along normalized plot of pulsatile contact stress $\sigma_{PCSNOR}(x)$ b,c=limits of integration defined by 60% of $\sigma_{PCSMAX}$ $$\text{Preferred } ASP: \sigma_{DCSAVG} = \frac{1}{L} \int_0^L \sigma_{DCS}(x) \cdot dx$$

Optimization Rule: PDBP'=a maximum.

AOP Definition: The PDBP is defined as the number of sampling locations along the stress sensitive element (or cumulative amount of segment lengths across the stress sensitive element) having normalized pulse stress values greater than a preselected threshold.

Theory Behind the Method: The largest value in the first derivative of PDBP occurs when the localized vessel wall collapses due to localized internal versus external pressure imbalances.

Method Steps:

1. Using the artery applanation control mechanism, the applanation state of artery 26 is changed to over a broad range of arterial applanation states while acquiring stress data (spatially distributed across the length of stress sensitive element 32) at each applanation state.

2. For each applanation state, computing PDBP, and ASP.

3. Creating a function PDBP(ASP), and from that function creating a second function PDBP'(ASP); where PDBP'(ASP) is defined as the first derivative of PDBP(ASP) with respect to ASP.

4. Defining the optimum applanation state to occur when PDBP'(ASP) is a maximum.

5. Determining the optimum applanation state as defined by that value of ASP which corresponds to: $PDBP'_{OPT} = PDBP'_{MAX}$

DETAILED DISCUSSION OF METHOD 8

This method utilizes the Diastolic Distribution Breadth Parameter (DDBP) to determine the optimum applanation state of the artery of interest. The DDBP is defined as the ratio of the average diastolic stress over the entire length of the stress sensitive element to the average diastolic stress in a localized region of the stress sensitive element containing the maximum pulse energy. The DDBP is a measure of the spatial uniformity of the diastolic stress distribution profile over the diaphragm length (normalized to the pulsatily energetic region(s) of the stress sensitive element). DDBP can be thought of as the relationship between representative diastolic stresses in the pulsatily inactive versus active regions of the stress sensitive element. A graphical representation of the method of calculating DDBP for a given applanation state is disclosed in FIG. 33. Mathematically, DDBP is defined (at any applanation state) as follows:

$$DDBP = \frac{\frac{1}{L}\int_0^L \sigma_{DCS}(x) \cdot dx}{\frac{1}{c-b}\int_b^c \sigma_{DCS}(x) \cdot dx}$$

Method 8 estimates the optimum applanation state of the artery of interest by computing the first derivative of DDBP(ASP). Thus, when DDBP'(ASP) is a maximum, the optimum arterial applanation state occurs. The implementation of Method 8 will now be discussed in conjunction with FIGS. 32 and 33.

Figure 32:
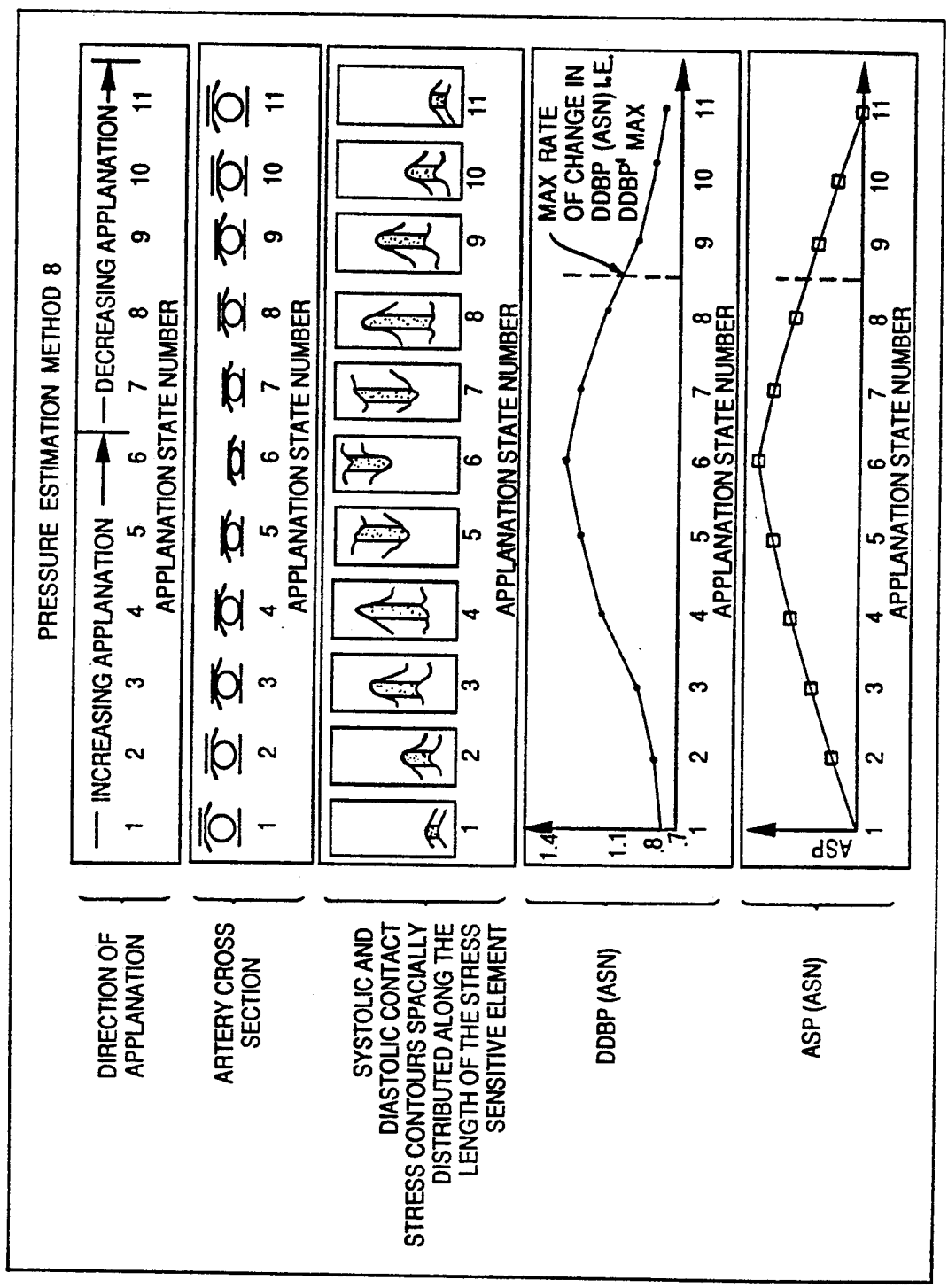
FIG. 32 is a diagrammatic and graphical representation of the method steps of Method 8 utilized in generating the DDBP parameter as a function of ASP.
Figure 33:
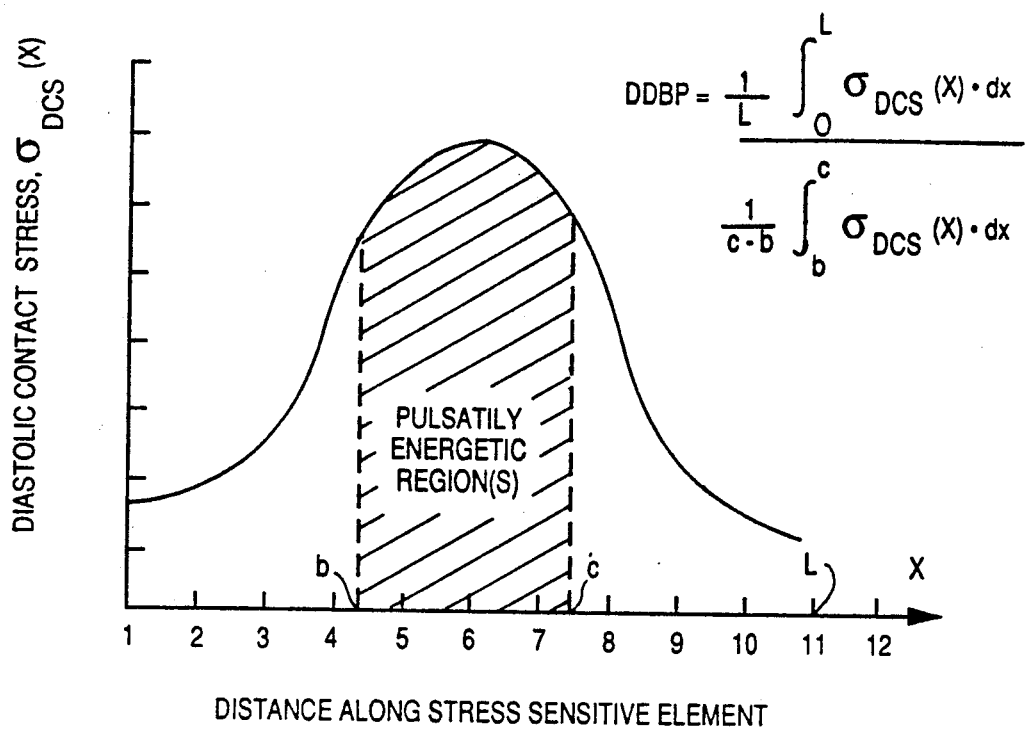
FIG. 33 is a graphical representation of the calculation of the DDBP parameter for a given applanation state.

Now referring to FIGS. 32 and 33, when implementing Method 8, first the artery applanation control mechanism is used to adjust the applanation state of artery 26 through a broad range of applanation states while acquiring contact stress data (spatially distributed across the length of the stress sensitive element 32 at each applanation state). For each applanation state, the DDBP and ASP are calculated. The preferred ASP for use in Method 8 is mean diastolic stress computed as follows:

$$\sigma_{DCSAVG} = \frac{1}{L}\int_0^L \sigma_{DCS}(x) \cdot dx$$

Next, a special function is created DDBP(ASP) and a new function is computed DDBP'(ASP). The optimum applanation state is defined to be that state of artery applanation which occurs when DDBP'(ASP) is a maximum. From the function DDBP'(ASP), the optimum value of the ASP is found according to the following formula:

$DDBP'_{OPT} = DDBP'_{MAX}$

SUMMARY OF METHOD 8

$$AOP: DDBP = \frac{\frac{1}{L}\int_0^L \sigma_{DCS}(x) \cdot dx}{\frac{1}{c-b}\int_b^c \sigma_{DCS}(x) \cdot dx}$$

$$\text{Preferred } ASP: \sigma_{DCSAVG} = \frac{1}{L}\int_0^L \sigma_{DCS}(x) \cdot dx$$

Optimization Rule: DDBP'=a maximum.

AOP Definition: The DDBP is defined as the ratio of the average diastolic stress over the entire length of the stress sensitive element to the average diastolic stress in the region of the stress sensitive element containing the maximum pulse energy.

Theory Behind the Method: The largest value of the first derivative of DDBP occurs with localized arterial wall collapse due to localized internal versus external pressure imbalance.

Method Steps:

1. Using the artery applanation control mechanism, the applanation state of artery 26 is changed over a broad range of arterial applanation states while acquiring contact stress data (spatially distributed along the length of the stress sensitive element 32) at each applanation state.)

2. For each applanation state, computing DDBP and ASP.

3. Creating a function DDBP(ASP), and from that function creating a second function DDBP'(ASP).

4. Defining the optimum applanation state to occur when DDBP' is a maximum.

5. Determining the optimum applanation state as defined by that value of ASP which corresponds to:

$$DDBP'_{OPT} = DDBP'_{MAX}$$

DETAILED DISCUSSION OF METHOD 9

This method utilizes the Spatially Averaged Stress Parameters SASPs to determine the optimum applanation state of the artery of interest. The SASPs are a group of four parameters each of which are defined as follows:

1). PULSATILE STRESS PARAMETER (PPAR)
At any given state of applanation, it is a measure of the spatial average (or weighted spatial average) change in stress between systole and diastole [pulse stress] in the region of the sensor receiving maximum pulse energy.

2). DIASTOLIC STRESS PARAMETER (DPAR)
At any given state of applanation, it is a measure of the spatial average (or weighted spatial average) contact stress at diastole in the region of the sensor receiving maximum pulse energy.

3). SYSTOLIC STRESS PARAMETER (SPAR) p1
At any given state of applanation, it is a measure of the spatial average (or weighted spatial average) contact stress at systole in the region of the sensor receiving maximum pulse energy.

4). MEAN STRESS PARAMETER (MPAR)
At any given state of applanation, it is a measure of the spatial average (or weighted spatial average) contact stress corresponding to the blood pressure waveform mean in the region of the sensor receiving maximum pulse energy.

Figure 34:
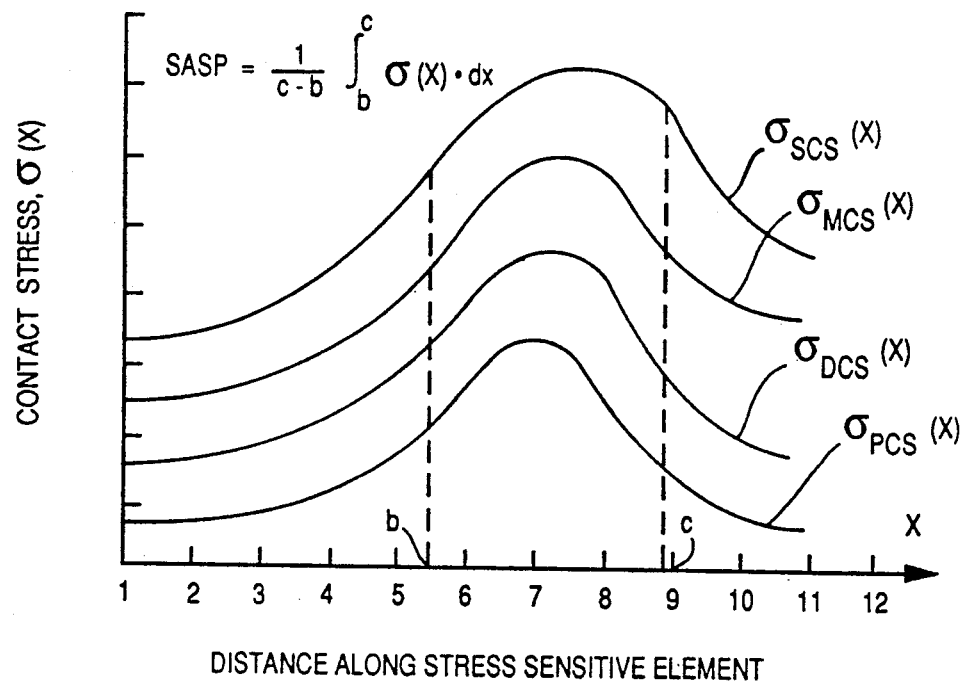
FIG. 34 is a graphical representation of the calculation of the SASP parameters for a given applanation state.

A graphical representation of the method of calculating the SASPs for a given applanation state is disclosed in FIG. 34. Mathematically, the SASPs are defined as follows:

$$PPAR = \frac{1}{c-b} \int_b^c \sigma_{PCS}(x) \cdot dx \quad 1)$$

$$DPAR = \frac{1}{c-b} \int_b^c \sigma_{DCS}(x) \cdot dx \quad 2)$$

$$SPAR = \frac{1}{c-b} \int_b^c \sigma_{SCS}(x) \cdot dx \quad 3)$$

$$MPAR = \frac{1}{c-b} \int_b^c \sigma_{MCS}(x) \cdot dx \quad 4)$$

Figure 35:
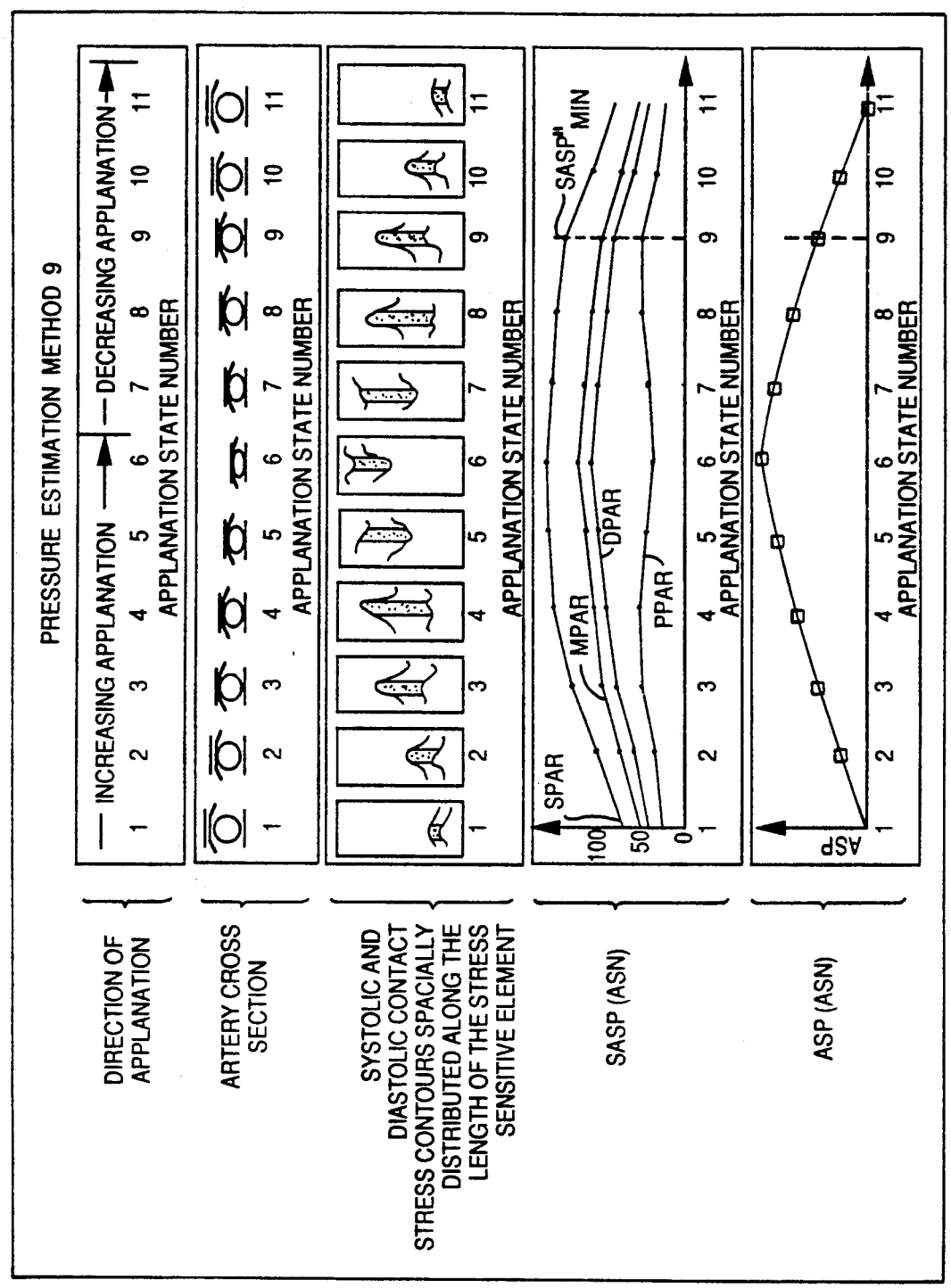
FIG. 35 is a diagrammatic and graphical representation of the method steps of Method 9 utilized in generating the SASP parameters as a function of ASP.
Figure 36:
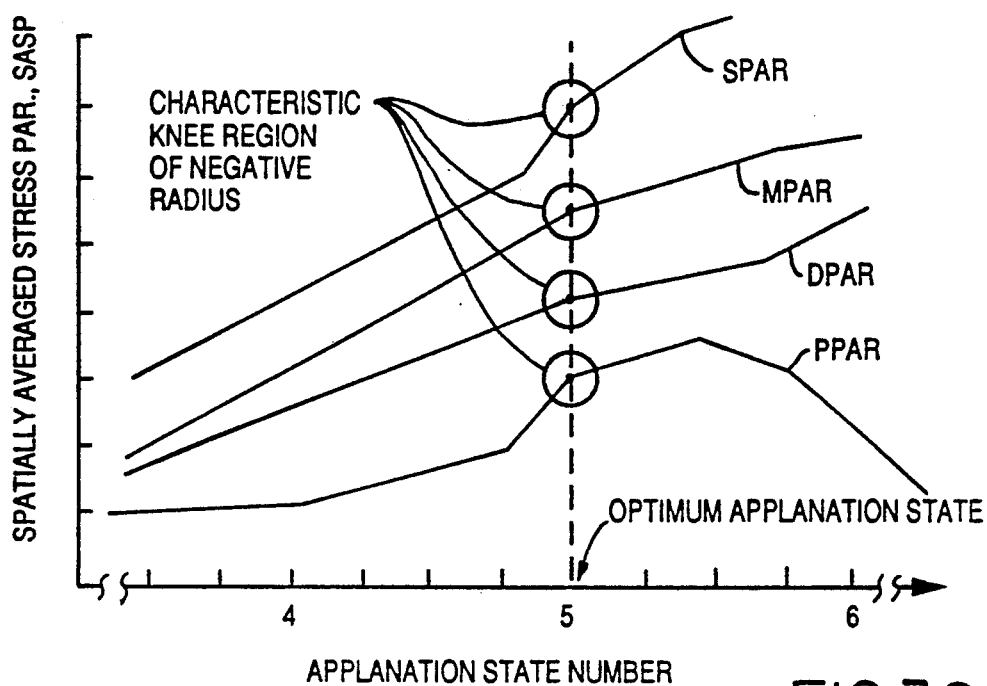
FIG. 36 is a graphical representation of the spatially averaged stress parameters showing the characteristic knee regions about the optimum applanation state.

Method 9 estimates the optimum applanation state of the artery of interest by computing the second derivative of at least one of the SASPs with respect to the selected ASP. After the second derivative is found (SASP''), the minimum of the second derivative is calculated and the optimum arterial applanation state is defined as being equal to SASP$_{MIN}$. The approach set forth in Method 9 takes advantages of a feature found in the second derivative of the SASP functions. Namely, when the second derivative of the SASP functions is a mimimum, this empirically corresponds to the "best applanation point" as it locates the abrupt "knee" in each tonometric parameter function. Thus, as is shown in FIG. 35, assuming that the optimum applanation state appears at applanation state number 5, each one of the SASPs demonstrates a change in slope going from a greater slope prior to applanation state number to a lesser slope after applanation state number 5. This sharp demarkation in slope across applanation state from greater to lesser slope 5 is a characteristic "knee" region of negative radius. FIG. 36 amplifies the area of negative radius as seen in FIG. 35 to better demonstrate the decreasing slope which occurs in all of the SASPs as they cross the optimum applanation state. The abrupt "knee" in these functions is recognized as the region having a localized prominent tight negative radius generally occurring in the neighborhood of (or somewhat below) the applanation state associated with the maximum value of the pulsatile parameter. This knee region is the region of change in behavior of contact stress versus applanation state associated with the collapse or buckling of a portion of the arterial wall. This region marks the applanation state where the contact stress over a portion of the arterial wall becomes equilibrated with the arterial internal pressure.

Figure 37:
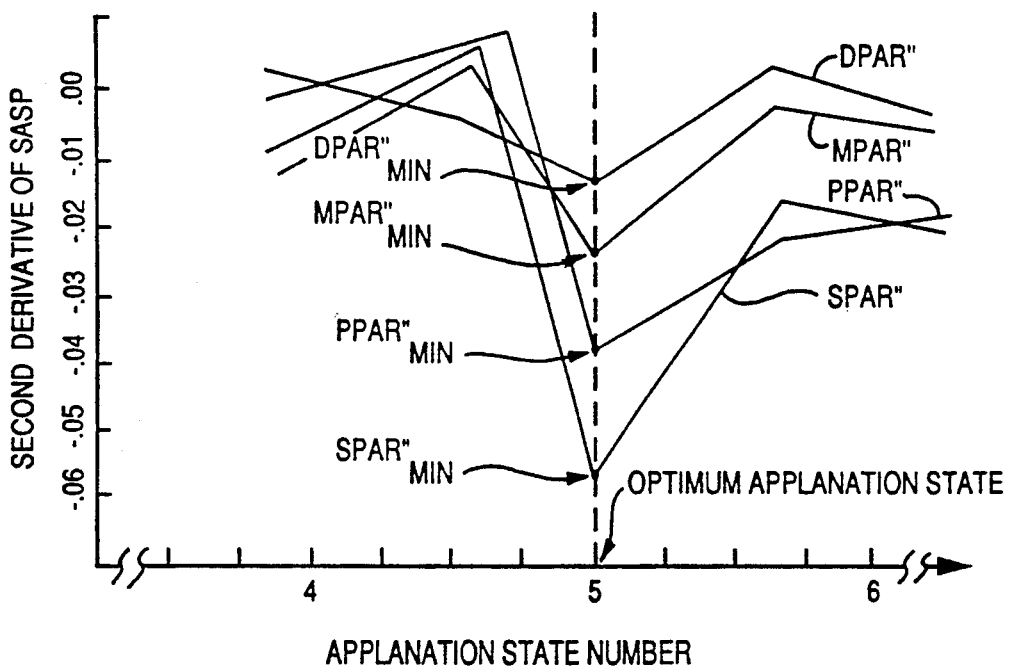
FIG. 37 is a graphical representation of the second derivative of the functions of FIG. 36.

FIG. 37 depicts the second derivative of the SASP functions versus the applanation state. Note the existence of the prominent minima in the second derivative functions and their association with the characteristic knee regions in the SASP parameters shown in FIG. 36.

When implementing Method 9, any one of the four SASPs can be used separately to achieve the determination of optimum applanation state. Also, a composite indicator can be formed from two or more of the SASPs and the resulting composite can be used to estimate the optimum applanation state. The implementation of Method 9 will now be discussed in conjunction with FIGS. 34-37.

Now referring to FIGS. 34-37, when implementing Method 9, first the artery applanation control mechanism is used to adjust the applanation state of artery 26 through a broad range of applanation states while acquiring contact stress data (spatially distributed across the length of the stress sensitive element 32) at each applanation state. For each applanation state, each of the four SASPs are calculated along with a preferred ASP. The preferred ASP for use in Method 9 is the mean diastolic stress computed as follows:

$$\sigma_{DCSAVG} = \frac{1}{L} \int_0^L \sigma_{DCS}(x) \cdot dx$$

Next, a special function is created between each of the four SASPs and the ASP. The optimum applanation state is defined to be that state of artery applanation which occurs when SASP''(ASP) is a minimum. From the function SASP''(ASP), the optimum value of the ASP is found according to the following formula:

$$SASP''_{OPT} = SASP''_{MIN}$$

SUMMARY OF METHOD 9

AOP:

-continued $$DPAR = \frac{1}{c-b} \int_b^c \sigma_{DCS}(x) \cdot dx$$

$$SPAR = \frac{1}{c-b} \int_b^c \sigma_{SCS}(x) \cdot dx$$

$$MPAR = \frac{1}{c-b} \int_b^c \sigma_{MCS}(x) \cdot dx$$

$$PPAR = \frac{1}{c-b} \int_b^c \sigma_{PCS}(x) \cdot dx$$

$$\text{Preferred } ASP: \sigma_{DCSAVG} = \frac{1}{L} \int_0^L \sigma_{DCS}(x) \cdot dx$$

Optimization Rule: SASP″=a minimum.
AOP Definition:

1). PULSATILE STRESS PARAMETER (PPAR)

At any given state of applanation, it is a measure of the spatial average (or weighted spatial average) change in stress between systole and diastole [pulse stress] in the region of the sensor receiving maximum pulse energy.

2). DIASTOLIC STRESS PARAMETER (DPAR)

At any given state of applanation, it is a measure of the spatial average (or weighted spatial average) contact stress at diastole in the region of the sensor receiving maximum pulse energy.

3). SYSTOLIC STRESS PARAMETER (SPAR)

At any given state of applanation, it is a measure of the spatial average (or weighted spatial average) contact stress at systole in the region of the sensor receiving maximum pulse energy.

4). MEAN STRESS PARAMETER (MPAR)

At any given state of applanation, it is a measure of the spatial average (or weighted spatial average) contact stress corresponding to the blood pressure waveform mean in the region of the sensor receiving maximum pulse energy.

Theory Behind the Method: The knee region of negative radius shows up prominently in the second derivative of each of the four SASPs. This negative radius region is the region of change of behavior of contact stress associated with the collapse or buckling of a portion of the vessel wall. This marks the applanation state where arterial contact stress over a portion of the vessel wall becomes equilibrated with the arterial internal pressure.

Method Steps:

1. Using the artery applanation control mechanism, the applanation state of artery 26 is changed over a broad range of arterial applanation states while acquiring contact stress data (spatially distributed across the length of the stress sensitive element 32) at each applanation state.

2. For each applanation state, the four SASP functions are computed along with a preferred ASP.

3. Creating a function between each of the four SASPs and ASP, and from those four functions creating a second derivative function of each of the four SASPs.

4. Determining the optimum applanation state as defined by that value of ASP which corresponds to the minima of a second derivative of one or more of the SASPs.

Computational Approach: Closed form mathematical expressions of each of the four SASP functions can be generated using polynomial functions (e.g. fourth or fifth order expressions) derived by using a best fit (e.g. least squares fit) of the data generated in step 1 above. Also, in one computing the second derivative of the SASP functions, the second derivative can be estimated numerically using second differences with respect to applanation state by operating on the numerical data established in step 2.

DETAILED DISCUSSION OF METHOD 10

This method utilizes the Stress Spatial Curvature Parameters SSCPs to determine the optimum applanation state of the artery of interest. The SSCPs are comprised of four parameters defined as follows:

(1) PULSATILE CURVATURE PARAMETER (PCPAR)

At any given state of applanation, it is a measure of the spatial curvature of the pulsatile contact stress versus distance (along the stress sensitive element) in the pulsatily active region of the stress sensitive element. It is defined as the 2nd derivative of the pulsatile contact stress versus distance function evaluated at the effective center of the pulsatily active region of the stress sensitive element.

$$PCPAR = \left. \frac{\partial^2 \sigma_{PCS}(x)}{\partial x^2} \right|_{x=\bar{x}}$$

(2) DIASTOLIC CURVATURE PARAMETER (DCPAR)

At any given state of applanation, it is a measure of the spatial curvature of the diastolic contact stress versus distance (along the stress sensitive element) in the pulsatily active region of the stress sensitive element. It is defined as the 2nd derivative of the diastolic contact stress versus distance function evaluated at the effective center of the pulsatily active region of the stress sensitive element.

$$DCPAR = \left. \frac{\partial^2 \sigma_{DCS}(x)}{\partial x^2} \right|_{x=\bar{x}}$$

(3) SYSTOLIC CURVATURE PARAMETER (SCPAR)

At any given state of applanation, it is a measure of the spatial curvature of the systolic contact stress versus distance (along the stress sensitive element) in the pulsatily active region of the stress sensitive element. It is defined as the 2nd derivative of the systolic contact stress versus distance function evaluated at the effective center of the pulsatily active region of the stress sensitive element.

$$SCPAR = \left. \frac{\partial^2 \sigma_{SCS}(x)}{\partial x^2} \right|_{x=\bar{x}}$$

(4) MEAN CURVATURE PARAMETER (MCPAR)

At any given state of applanation, it is a measure of the spatial curvature of the mean contact stress versus distance (along the stress sensitive element) in the pulsatily active region of the stress sensitive element. It is defined as the 2nd derivative of the mean contact stress versus distance function evaluated at the effective center of the pulsatily active region of the stress sensitive element.

$$MCPAR = \frac{\partial^2 \sigma_{MCS}(x)}{\partial x^2}\bigg|_{x=\bar{x}}$$

Figure 38:
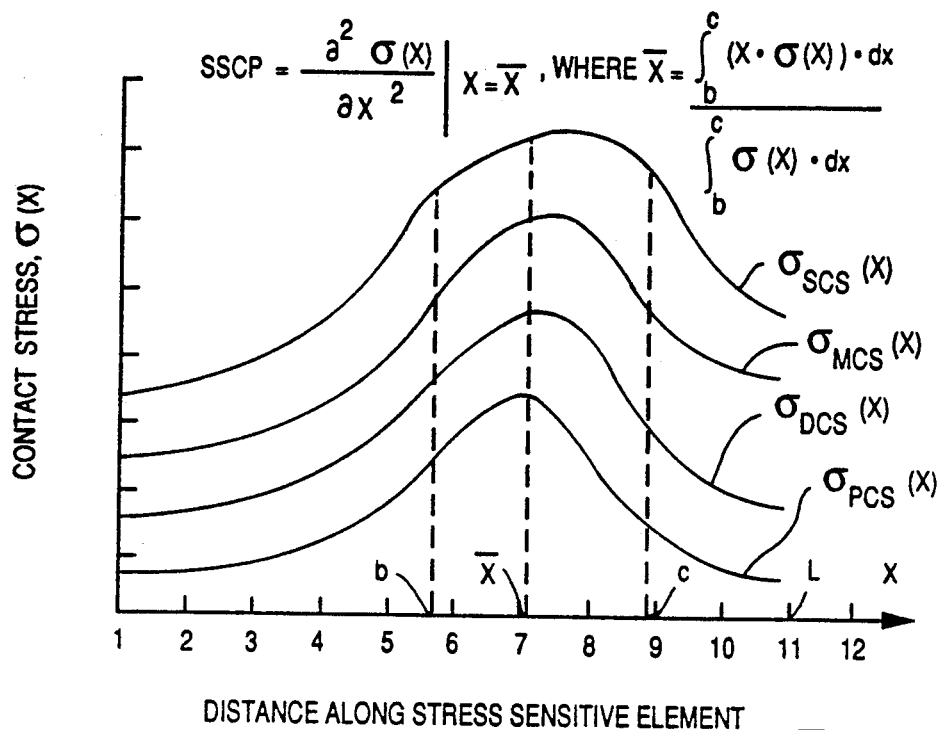
FIG. 38 is a graphical representation of the calculation of the SSCP parameters for a given applanation state.
Figure 43:
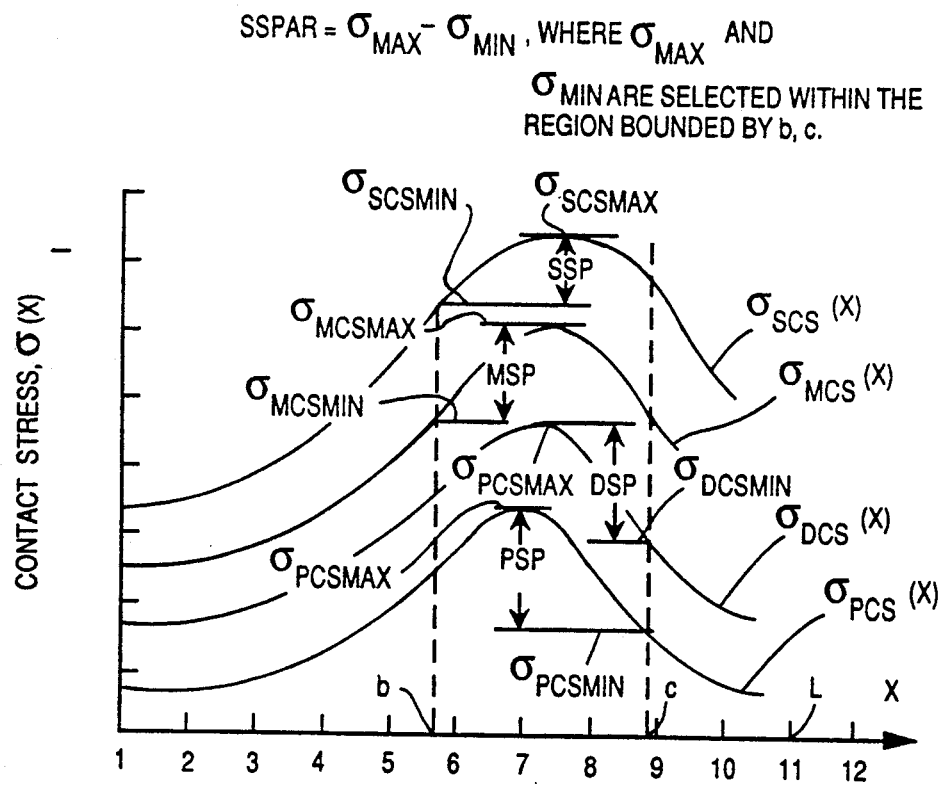
FIG. 43 is a graphical representation of the calculation of the SSPAR parameters for a given applanation state.

The SSCPs focus on the importance of spatial contours of constituent components of the tissue contact stress distribution along the length of the stress sensitive element and also highlight the changing nature of the spatial contours with respect to applanation state. The focus of each of the four SSCPs is the spatial curvature of the tissue contact stress distribution function in the pulsatily active region of the stress sensitive element. A graphical representation of the method of calculating the SSCPs for a given applanation state is disclosed in FIG. 38. Mathematically, the SSCPs are defined as follows:

$$SSCP = \frac{\partial^2 \sigma(x)}{\partial x^2}\bigg|_{x=\bar{x}}$$

$$\text{where: } \bar{x} = \frac{\int_b^c (x \cdot \sigma(x)) \cdot dx}{\int_b^c \sigma(x) \cdot dx}$$

Figure 39:
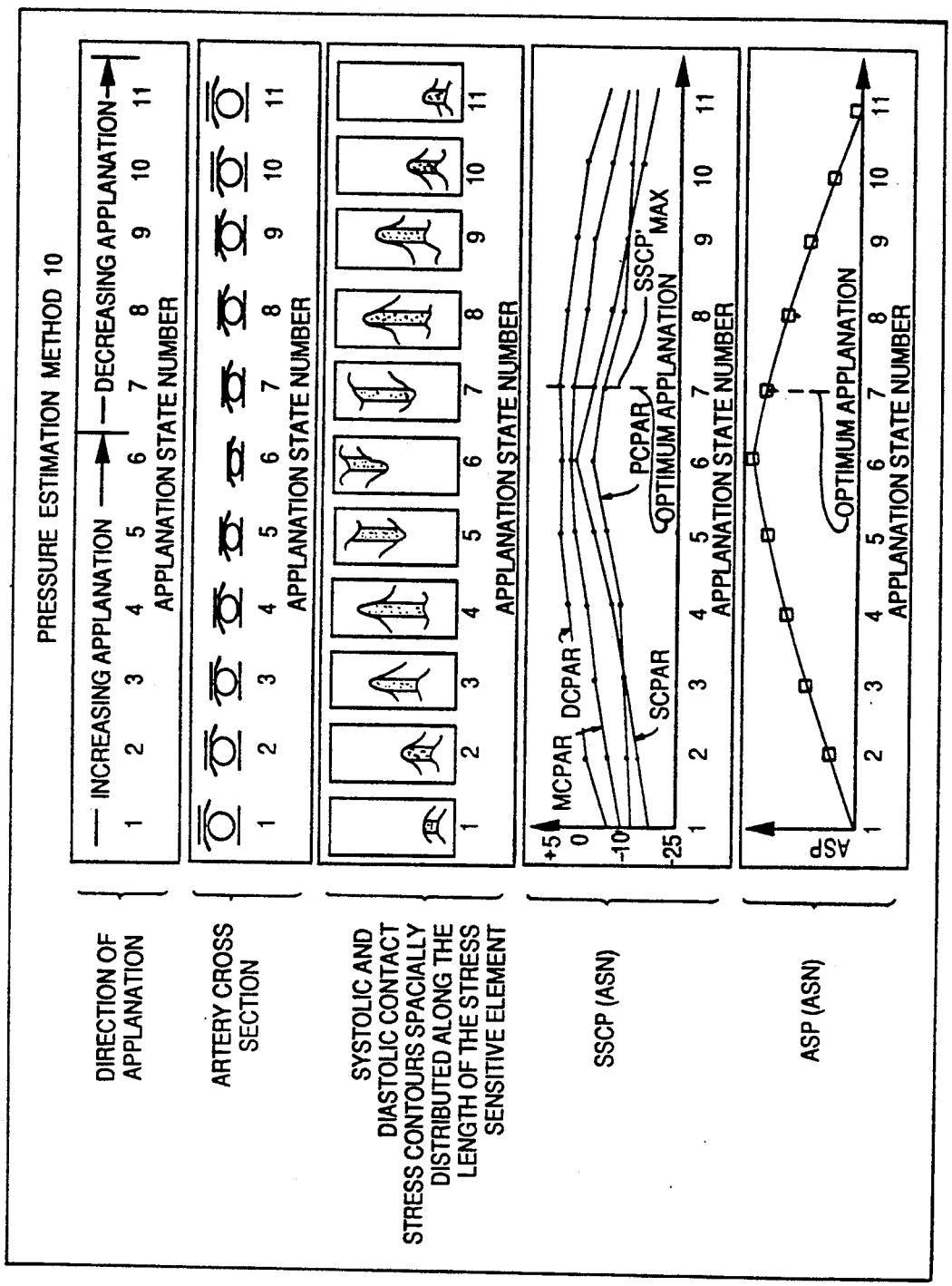
FIG. 39 is a diagrammatic and graphical representation of the method steps of Method 10 utilized in generating the SSCP parameters as a function of ASP.
Figure 40:
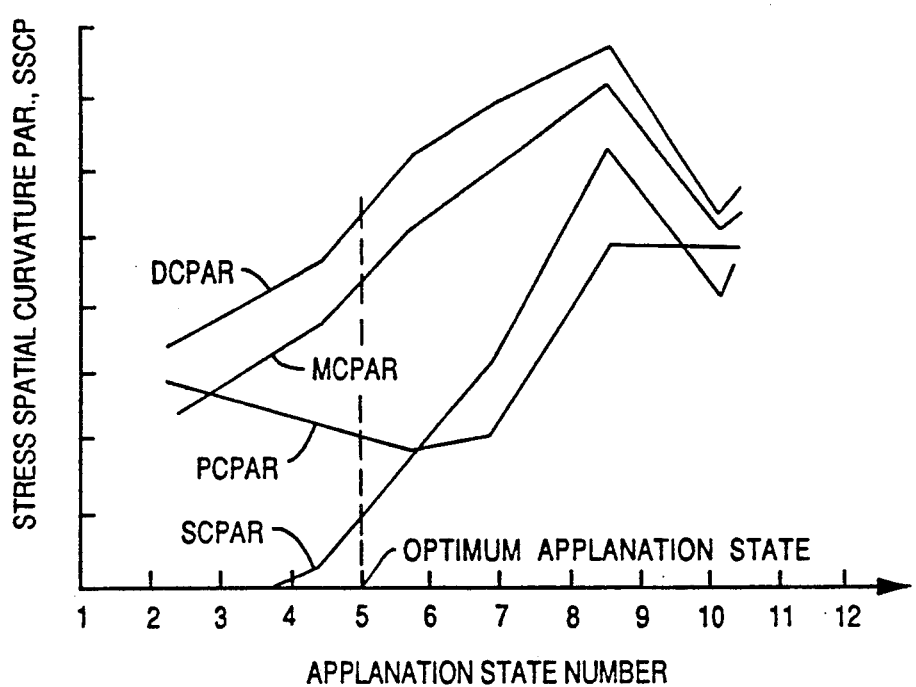
FIG. 40 is a graphical representation of the SSC parameters as a function of applanation state number.
Figure 41:
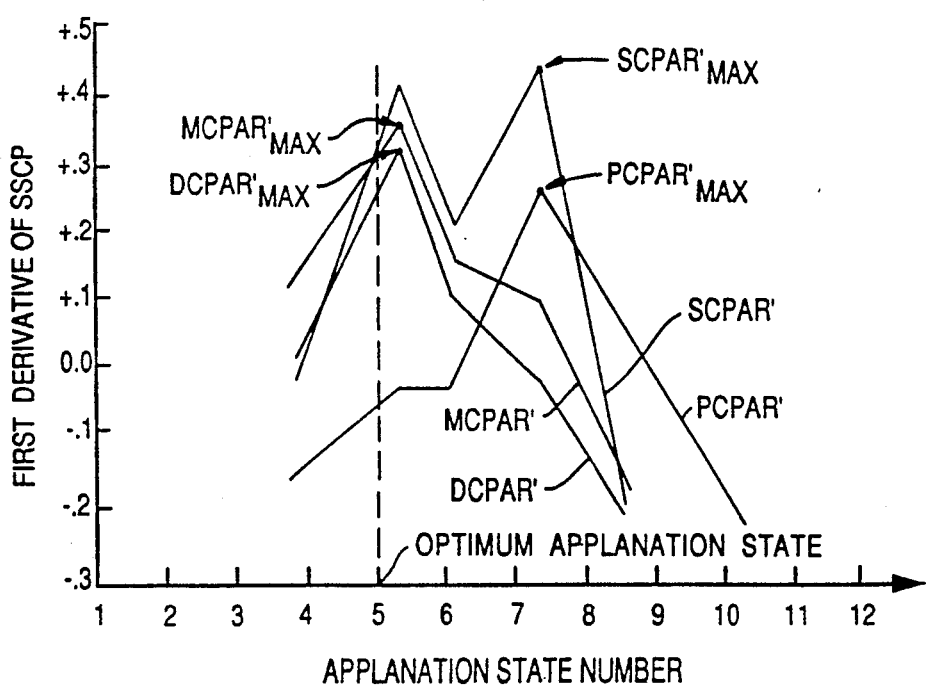
FIG. 41 is a graphical representation of the first derivative of the functions of FIG. 40.
Figure 42:
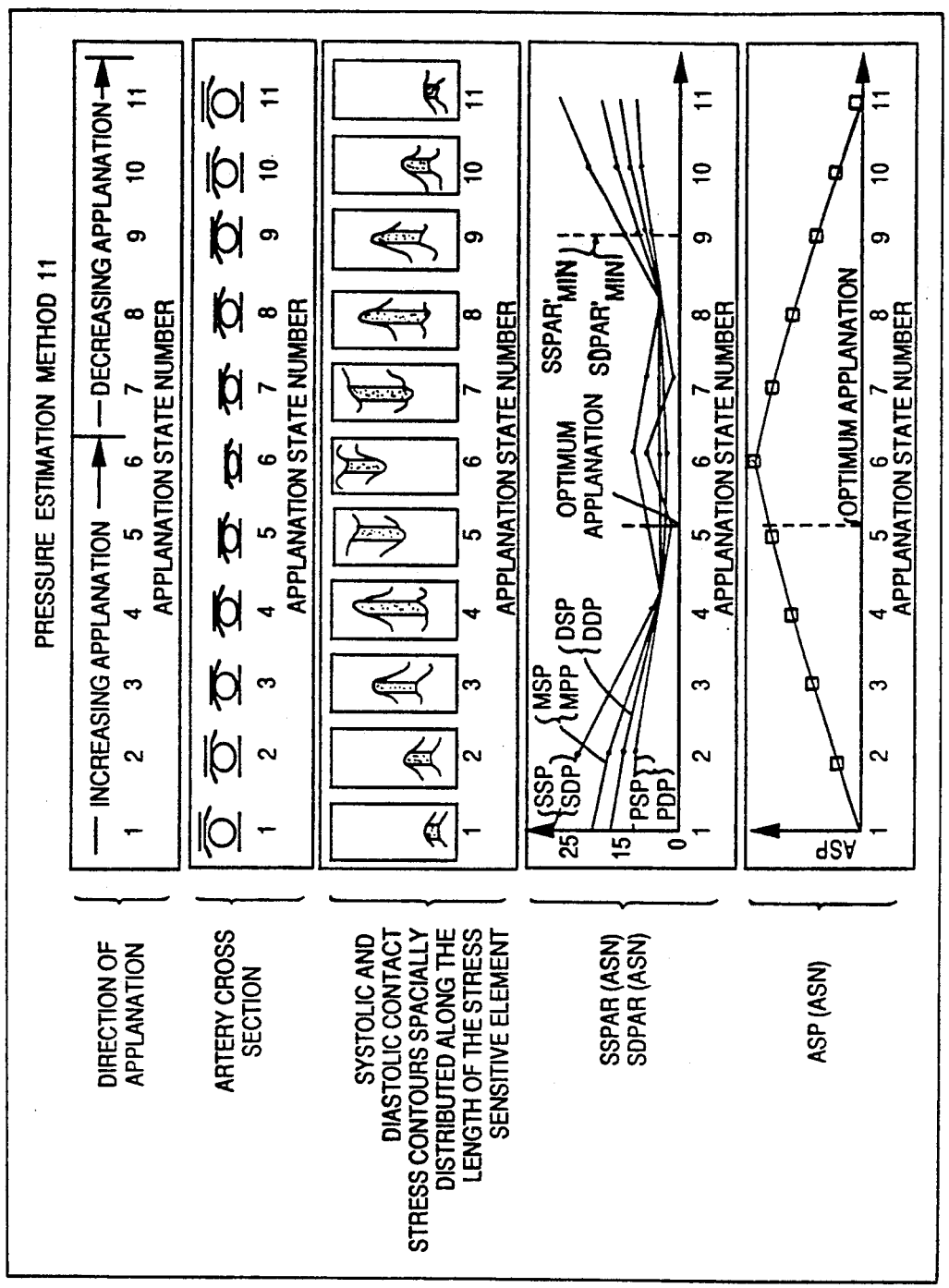
FIG. 42 is a diagrammatic and graphical representation of the method steps of Method 11 utilized in generating the SSPAR and the SDPAR parameters as a function of ASP.

Additionally, $\bar{x}$ could be established using any of the centroidal methods disclosed in co-pending U.S. patent application entitled "Method of Determining Which Portion of a Stress Sensor is Best Positioned For Use In Determining Intra-Arterial Blood Pressure"; Ser. No. 07/835,635 filed Feb. 3, 1992, which is hereby incorporated by reference. The behavior of the SSCPs with changing applanation state is an important ingredient of Methodology 10. Like the previous methodologies, the SSCPs are defined as a function of a selected ASP. FIGS. 39 and 40 show the SSCPs plotted as a function of an applanation states number. A careful look at the behavior as depicted in FIGS. 39 and 40 shows an applanation is increased through and above the region of optimum applanation, a characteristic and prominent sudden increase in each of the spatial curvatures is found to occur at or around the optimum state of applanation. This behavior is most apparent when viewing the graph of FIG. 41 which is a graph of the first derivative of the SSCPs. In FIG. 41, the prominent maximum is seen in the close neighborhood of the optimum applanation state. The region of "maxima" in the first derivative functions corresponds to an applanation state associated with the collapse or buckling of a portion of the arterial wall. This occurs at the applanation state where the arterial external contact stress over a portion of the arterial wall becomes equilibrated with the arterial internal pressure.

Any one of the four listed SSCP parameters can be used to find the optimum applanation state. Additionally, a composite of two or more of the SSCPs can be used in conjunction with one another to provide a composite resulting estimated optimum applanation state. The implementation of Method 10 will now be discussed in conjunction with FIGS. 38-41.

Now referring to FIGS. 38-41, when implementing Method 10, first the artery applanation control mechanism is used to adjust the applanation state of artery 26 through a broad range of applanation states while acquiring contact stress data (spatially distributed across the length of stress sensitive element 32) at each applanation state. For each applanation state, one or more of the SSCPs are calculated along with a corresponding preferred ASP. The preferred ASP for use in Method 10 is mean diastolic stress computed as follows:

$$\sigma_{DCSAVG} = \frac{1}{L}\int_0^L \sigma_{DCS}(x) \cdot dx$$

Next, a special function is created between each of the SSCPs and the ASP, SSCP(ASP) and the first derivative of each of the SSCP functions are also computed as a function of ASP. The optimum applanation state is defined to be that state of artery applanation which occurs when the first derivative of one or more of the SSCP(ASP)s is a maximum. From the function SSCP'(ASP) the optimum value of the ASP is found according to the following formula:

$$SSCP'_{OPT} = SSCP'_{MAX}$$

SUMMARY OF METHOD 10

$$AOP: SSCP = \frac{\partial^2 \sigma(x)}{\partial x^2}\bigg|_{x=\bar{x}}$$

$$\text{where: } \bar{x} = \frac{\int_b^c (x \cdot \sigma(x)) \cdot dx}{\int_b^c \sigma(x) \cdot dx}$$

$$\text{Preferred } ASP: \sigma_{DCSAVG} = \frac{1}{L}\int_0^L \sigma_{DCS}(x) \cdot dx$$

Optimization Rule: SSCP' = a maximum.

AOP Definition: The SSCP are defined as the spatial curvature of the tissue contact stress distribution function in the pulsatily active regions of the stress sensitive element.

Theory Behind the Method: The region of "maxima" in the first derivative functions of each of the SSCPs corresponds to an applanation state associated with collapse or buckling of a portion of the artery wall. This occurs at an applanation state where contact stress external to the artery wall becomes equilibrated with the arterial internal pressure.

Method Steps:

1. Using the artery applanation control mechanism, the applanation state of artery 26 is changed over a broad range of arterial applanation states while acquiring contact stress data (spatially distributed across the length of the stress sensitive element 32) at each applanation state.

2. For each applanation state, computing each of the four SSCPs and a corresponding preferred ASP.

3. Creating a function SSCP(ASP) and from that function creating a second function SSCP'(ASP).

4. Defining the optimum applanation state to occur when SSCP' is a maximum.

5. Determining the optimum applanation state as defined by that value of ASP which corresponds to:

$$SSCP'_{OPT} = SSCP'_{MAX}$$

Computational Approach: Closed form mathematical expressions of each of the four SSCP functions can be generated using polynomial functions (e.g. fourth or fifth order expressions) derived by using a best fit (e.g. least squares fit) of the data generated in step 1 above. Also, in one computing the first derivative of the SSCP functions, the first derivative can be estimated numerically using differences with respect to applanation state by operating on the numerical data established in step 2.

DETAILED DISCUSSION OF METHOD 11

This method utilizes parameters defined as Stress Variation Parameters SVPARs to determine the optimum applanation state of the artery of interest. Stress Variation Parameters SVPARs fall into one of two possible sub-classes—Stress Spread Parameters (SSPAR) and Stress Deviation Parameters (SDPAR). This Method is based upon the importance of local deviations existing in constituent components of the tissue contact stress occurring over the pulstily energetic region of the stress sensitive element. More particularly, Method 11 focuses on the behavior of the contact stress deviations with changing state of applanation as the applanation and control system displaces the sensor into the tissue to create a variety of artery applanation states.

The SSPAR applanation optimization parameters used to indicate local deviation in the contact stresses are:

(1) Pulsatile Spread Parameter (PSP)
At any given state of applanation, it is a measure of the maximum spread or difference between the maximum pulsatile stress and the minimum pulsatile stress occurring in the region of the stress sensitive element receiving maximum pulse energy $PSP = \sigma_{PCSMAX} - \sigma_{PCSMIN}$ within the pulsatily energetic region of the stress sensitive element as defined by bounding limits b,c.

(2) Diastolic Spread Parameter (DSP)
At any given state of applanation, it is a measure of the maximum spread or difference between the maximum diastolic stress and the minimum diastolic stress occurring in the region of the stress sensitive element receiving maximum pulse energy. $DSP = \sigma_{DCSMAX} - \sigma_{DCSMIN}$ within the pulsatily energetic region of the stress sensitive element as defined by bounding limits b,c.

(3) Systolic Spread Parameter (SSP)
At any given state of applanation, it is a measure of the maximum spread or difference between the maximum systolic stress and the minimum systolic stress occurring in the region of the stress sensitive element receiving maximum pulse energy. $SSP = \sigma_{SCSMAX} - \sigma_{SCSMIN}$ within the pulsatily energetic region of the stress sensitive element as defined by bounding limits b,c.

(4) Mean Spread Parameter (MSP)
At any given state of applanation, it is a measure of the maximum spread of difference between the maximum waveform mean stress and the minimum waveform means stress occurring in the region of the stress sensitive element receiving maximum pulse energy. $MSP = \sigma_{MCSMAX} - \sigma_{MCSMIN}$ within the pulsatily energetic region of the stress sensitive element as defined by bounding limits b,c.

In an alternate means of describing variations in contact stress over a local pulsatily energetic region of the stress sensitive element, the standard deviation is computed for all the sample points located in the local pulsatily energetic region. The SDPAR applanation optimization parameters used to indicate local deviation in the contact stresses are:

(1) Pulsatile Deviation Parameter (PDP)
At any state of applanation, it is a measure of standard deviation in pulsatile stress values $\sigma_{PCS}(x)$ sampled along the stress sensitive element in the region of the stress sensitive element receiving maximum pulse energy as defined by bounds b,c.

(2) Diastolic Deviation Parameter (DDP)
At any state of applanation, it is a measure of standard deviation in diastolic stress values $\sigma_{DCS}(x)$ sampled along the stress sensitive element in the region of the stress sensitive element receiving maximum pulse energy as defined by bounds b,c.

(3) Systolic Deviation Parameter (SDP)
At any state in applanation, it is a measure of standard deviation in systolic stress values $\sigma_{SCS}(x)$ sampled along the stress sensitive element in the region of the stress sensitive element receiving maximum pulse energy as defined by bounds b,c.

(4) Mean Deviation Parameter (MDP)
At any state of applanation, it is a measure of standard deviation in means stress values $\sigma_{MCS}(x)$ sampled along the stress sensitive element in the region of the stress sensitive element receiving maximum pulse energy as defined by bounds b,c.

The characteristic behavior of these local tissue stress spread and deviations parameters with changing state of applanation is an especially important aspect of Method 11. These applanation optimization spread and deviation parameters are described as functions of a preferred ASP. Although the remainder of this discussion focuses on the stress spread parameters SSPARs it is understood that all such discussions relate equally as well to the spread deviation parameters SDPARs.

Figure 44:
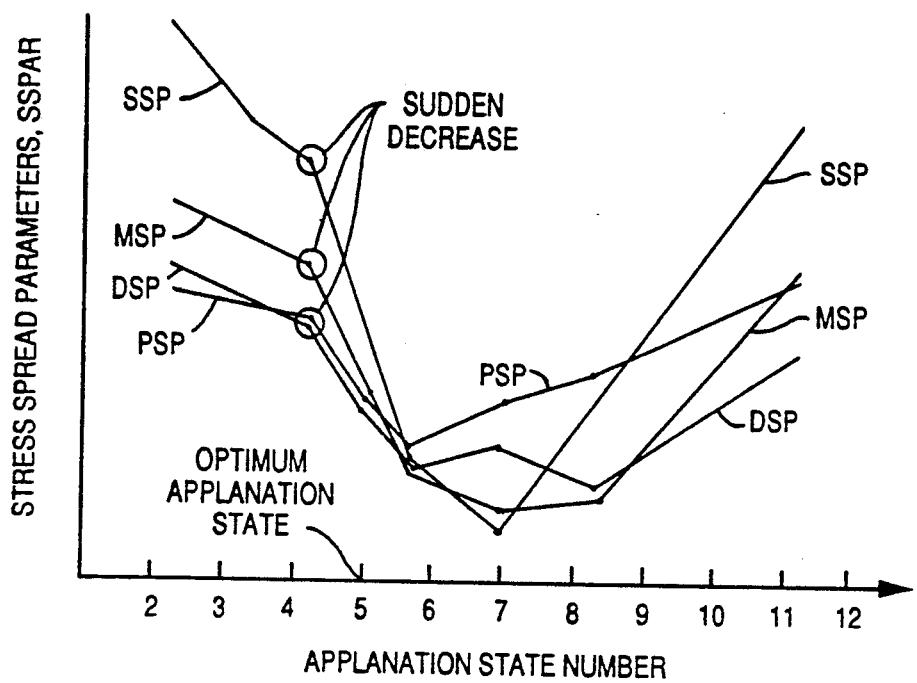
FIG. 44 is a graphical representation of the stress spread parameters as a function of applanation state number.
Figure 45:
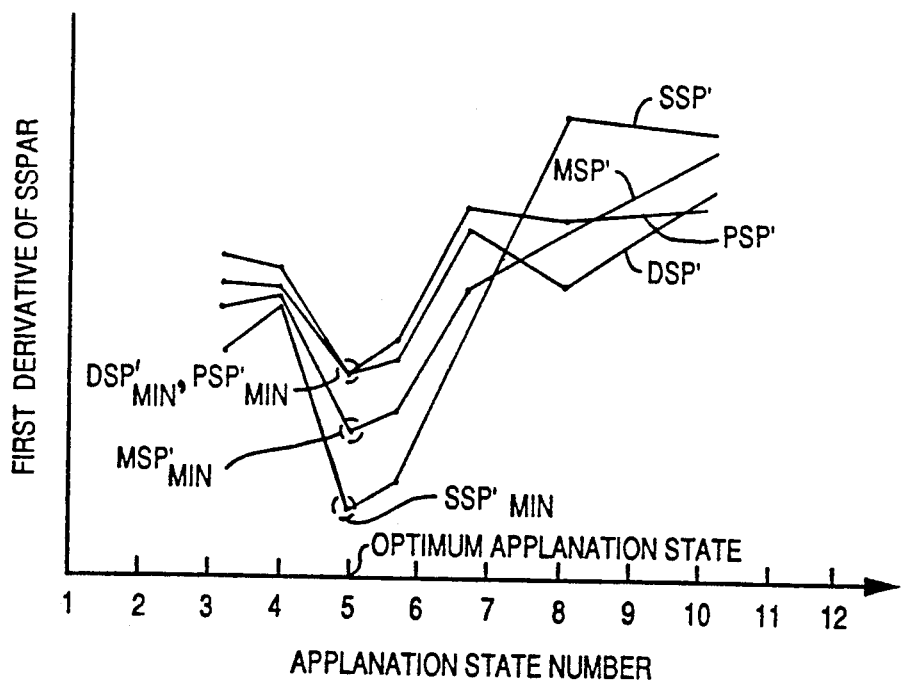
FIG. 45 is a graphical representation of the first derivative of the functions of FIG. 44 as a function of applanation state number.

Now referring to FIG. 44, examination of the behavior of the stress spread parameters as a function of ASP shows that as applanation is increased through and above the region of optimum applanation, a prominent sudden decrease in each of these functions is found to occur at or around the optimum applanation state. This characteristic behavior is most apparent upon investigation of the first derivatives of SSPAR(ASP) and SDPAR(ASP). The first derivative of the SSPARs is shown in FIG. 45.

An understanding of the physical mechanism involved which causes the sudden decrease as shown in FIG. 44 will now be explained. The region of a "minima" in each of the first derivative functions (see FIG. 45) corresponds to an applanation state associated with collapse or buckling of a portion of the arterial wall. This occurs at an applanation state where external contact stress in compression over a portion of the artery wall becomes equilibrated with the internal pressure of the artery. The local buckling or collapse occurs in a small region of the arterial wall under these conditions because the vessel wall itself cannot carry significant hoop compression loading. The implementation of Method 11 will now be discussed in conjunction with FIGS. 42–45.

Now referring to FIGS. 42–45, when implementing Method 11, first the artery applanation control mechanism is used to adjust the applanation state of artery 26 through a broad range of applanation states while acquiring contact stress data (spatially distributed along the length of stress sensitive element 32 at each applanation state. For each applanation state, the SSPARs are calculated along with a corresponding preferred ASP. The preferred ASP for use in Method 11 is mean diastolic stress computed as follows:

$$\sigma_{DCSAVG} = \frac{1}{L} \int_0^L \sigma_{DCS}(x) \cdot dx$$

Next, a special function is created between one or more SSPAR and the ASP and a new function (first derivative) is computed SSPAR'(ASP). The optimum applanation state is defined to be that state of artery applanation which occurs when SSPAR'(ASP) is a minimum. From the function SSPAR'(ASP) the optimum value of the ASP is found according to the following formula:

$$SSPAR'_{OPT} = SSPAR'_{MIN}$$

SUMMARY OF METHOD 11

AOP:

$$PSP = \sigma_{PCSMAX} - \sigma_{PCSMIN}$$

where $\sigma_{PCSMAX}$ and $\sigma_{PCSMIN}$ are selected from the pulsatily energetic region.

$$DSP = \sigma_{DCSMAX} - \sigma_{DCSMIN}$$

where $\sigma_{DCSMAX}$ and $\sigma_{DCSMIN}$ are selected from the pulsatily energetic region.

$$SSP = \sigma_{SCSMAX} - \sigma_{SCSMIN}$$

where $\sigma_{SCSMAX}$ and $\sigma_{SCSMIN}$ are selected from the pulsatily energetic region.

$$MSP = \sigma_{MCSMAX} - \sigma_{MCSMIN}$$

where $\sigma_{MCSMAX}$ and $\sigma_{MCSMIN}$ are selected from the pulsatily energetic region.

$$\text{Preferred } ASP: \sigma_{DCSAVG} = \frac{1}{L} \int_0^L \sigma_{DCS}(x) \cdot dx$$

Optimization Rule: SSPAR' = a minimum

AOP Definition: The SSPAR and the SDPAR are measures of the spread or deviation within the contact stress profile over the pulsatily energetic region of the stress sensitive element.

Theory Behind the Method: A sudden decrease in the contour of both SSPAR and SDPAR takes place at or around the optimum applanation state. This is because collapse or buckling takes place within the artery wall at or around the optimum applanation state.

Method Steps:

1. Using the artery applanation control mechanism, the applanation state of artery 26 is changed over a broad range of arterial applanation states while acquiring contact stress data (spatially distributed across the length of the stress sensitive element 32) at each applanation state.

2. For each applanation state computing one or more of the following arterial optimization parameters:
   a. pulsatile spread or deviation parameter PSP or PDP
   b. diastolic spread or deviation parameter, DSP or DDP
   c. systolic spread or deviation parameter, SSP or SDP
   d. means spread or deviation parameter, MSP or MDP.

In addition to computing the above optimization parameters, for each applanation state a preferred ASP is computed.

3. Creating a function of one or more of the above-referenced applanation optimization parameters versus ASP:
   a. PSP(ASP) or PDP(ASP)
   b. DSP(ASP) or DDP(ASP)
   c. SSP(ASP) or SDP(ASP)
   d. MSP(ASP) or MDP(ASP).

4. Creating functions of the first derivatives of the applanation optimization parameters with respect to ASP:
   a. PSP'(ASP) or PDP'(ASP)
   b. DSP'(ASP) or DDP'(ASP)
   c. SSP'(ASP) or SDP'(ASP)
   d. MSP'(ASP) or MDP'(ASP).

5. Defining the Optimum Application state to occur when the first derivative of one of the applanation optimization parameters is a minimum.

6. Determining the optimum applanation state as defined by that value of ASP which corresponds to:

$$PSP'(ASP_{OPT}) = PSP'_{MIN}$$

$$DSP'(ASP_{OPT}) = DSP'_{MIN}$$

$$SSP'(ASP_{OPT}) = DSP'_{MIN}$$

$$MSP'(ASP_{OPT}) = MSP'_{MIN}$$

And similarly for the optimization functions based on the deviation parameters:

$$PDP'(ASP_{OPT}) = PDP'_{MIN}$$

$$DDP'(ASP_{OPT}) = DDP'_{MIN}$$

$$SDP'(ASP_{OPT}) = DDP'_{MIN}$$

$$MDP'(ASP_{OPT}) = MDP'_{MIN}$$

When calculating the SSPARs and the SDPARs closed form mathematical expressions of these functions can be generated using polynomial functions (e.g., fourth or fifth order expressions) derived using best fit (e.g. least squares fit) of the data. These functions can also be expressed in tabular or numerical form. Also, the derivatives can be numerically approximated utilizing difference methods.

Method 11 should be considered more general than simply the detailed mathematical definitions given above. Method 11 should be considered as encompassing the general concept of using any mathematical description, function, or formula that examines the property of spread or deviation in contact stress profiles occurring over a defined pulsatily energetic region of the stress sensitive element. The mathematical definitions defined herein are merely important examples of the general concept. The procedure herein described in conjunction with Method 11 can be used independently with any one of the eight listed spread/deviation functions to achieve a resulting optimum applanation point. Additionally, a composite of two or more of the spread/deviation functions may be used to generate an optimum applanation point.

DETAILED DISCUSSION OF METHOD 12

This method of estimating optimum applanation is based on the concept that a better result is obtained from a consideration and use of some or all of the "best" applanation estimates from the 11 individual methods that have been previously described. The best overall estimate of the optimum applanation is a weighted average utilizing results of several of the optimum applanation methods.

The combined best applanation point is estimated by the following mathematical equation:

$$AOPCOM_{OPT} = \frac{\Sigma_i F[i] \cdot [AOP_{OPT}(i)]}{\Sigma_i F[i]}$$

where:
$AOPCOM_{OPT}$ = composite value of optimum applanation estimate
$AOP_{OPT}(i)$ = the value of the applanation optimization parameter associated with the ith Method of estimating optimum arterial compression
$i = 1-11$
$F$ = some predetermined weighting function as applied to $AOP_{OPT}(i)$ The implementation of Method 12 is preferably as follows. First, the artery applanation control mechanism is used to adjust the applanation state of artery 26 through a broad range of applanation states while acquiring contact stress data (spatially distributed across the length of stress sensitive element 32) at each applanation state. Next, the "best" applanation estimation methods are selected. For each selected method, using the step by step procedure for estimating the best applanation (as previously described in Method 1-11). For each selected method, choose the appropriate weighting factor to use in computing the combined applanation estimate. Finally, computing the combined estimated optimum applanation point using the combined equation:

$$AOPCOM_{OPT} = \frac{\Sigma_i F[i] \cdot [AOP_{OPT}(i)]}{\Sigma_i F[i]}$$

where:
$AOPCOM_{OPT}$ = composite value of optimum applanation estimate
$AOP_{OPT}(i)$ = the value of the applanation optimization parameter associated with the ith Method of estimating optimum arterial compression
$i = 1-11$
$F$ = some predetermined weighting function as applied to $AOP_{OPT}(i)$ The foregoing detailed description shows that the preferred embodiments of the present invention are well suited to fulfill the objects of the invention. It is recognized that those skilled in the art may make various modifications or additions to the preferred embodiments chosen here to illustrate the present invention, without departing from the spirit of the present invention. For example, although most of the methods disclosed herein deal primarily with discrete samples, and discrete sample sets, all of the disclosed methods apply equally as well to continuous functions. Thus, an alternative method to interpolating between finite applanation states would be to fit polynomial functions to the discrete data points so that closed form mathematical expressions are created and analyzed for all of the tonometric parameters of interest. Therefore, Methods 1-12 may be utilized by way of closed form mathematical functions, thereby providing an alternative to the use of the interpolation schemes. As another example, many of the methodologies have been defined in terms of finding the maximum or the minimum of a particular function and thereby locating the optimum applanation state. It will be understood by those skilled in the art that by simply altering the sign conventions used in constructing the various functions, that a minima on a graph can be mathematically transformed into a maxima and visea-versa. Accordingly, it is to be understood that the subject matter sought to be afforded protection hereby should be deemed to extend to the subject matter defined in the appended claims, including all fair equivalents thereof.

What is claimed is:

1. For use in a non-invasive blood pressure monitoring system, a method of estimating optimum arterial compression by measuring the stress of tissue overlying an artery of interest, said system of the type including a tissue stress sensor having a stress sensitive element, said stress sensitive element having a length that exceeds the lumen of said artery of interest, said method including the steps of:

(A) placing said stress sensitive element of said tissue stress sensor in communication with said tissue overlying said artery of interest, (B) orienting said stress sensitive element such that said length spans beyond the lumen of said artery of interest, (C) using said stress sensitive element to varyingly compress said artery of interest thereby applanating said artery of interest through a plurality of stages, and at each said applanation stage, (D) obtaining from said tissue stress sensor at least one electrical signal representing stress data across the length of said stress sensitive element, said stress data including a plurality of stress datum, each stress datum representing stress communicated to a predetermined portion of said stress sensitive element from said tissue overlying said artery of interest, each said predetermined portion of said stress sensitive element lying along said length of said stress sensitive element, and for each applanation stage, using said data for, (E) computing a pulse parameter and an applanation state parameter, (F) relating said pulse parameter to said applanation state parameter, (G) determining the value of said applanation state parameter which corresponds to a predetermined percentage of a maximum value of said pulse parameter, (H) estimating the optimum arterial compression to be that degree of artery applanation which produces the applanation state parameter value of step (G).

2. The method of claim 1, wherein step (E) includes computing said pulse parameter as follows:

$$PPAR = \frac{1}{c-b} \int_b^c \sigma_{PCS}(x) \cdot dx$$

where:
b,c = limits of integration
$\sigma_{PCS}(x)$ = pulsatile contact stress as a function of x
x = distance along the stress sensitive diaphragm.

3. The method of claim 1, wherein said applanation state parameter is computed as follows:

$$\sigma_{DCSAVG} = \frac{1}{L} \int_0^L \sigma_{DCS}(x) \cdot dx$$

where:
$\sigma_{DCSAVG}$ = average diastolic stress across the length of the stress sensitive element
L = length of stress sensitive element
$\sigma_{DCS}(x)$ = diastolic stress as a function of x
x = location along the stress sensitive element.

4. The method of claim 1, wherein said predetermined percentage is equal to generally 95 percent.

5. The method of claim 1, wherein step (G) further includes the sub-steps of,
  (i) increasing arterial applanation until said pulse parameter reaches a first maximum value, and then diminishes by a predetermined fraction of said first maximum value, then
  (ii) decreasing arterial applanation until said pulse parameter reaches a second maximum value, then
  (iii) continuing decreasing said arterial applanation until said pulsatile parameter reaches generally 95 percent of said second maximum value.

6. The method of claim 2, wherein said limits of integration b,c are computed by determining which portion of the stress sensitive element is in receipt of a predetermined quantity of the stress energy imparted to the stress sensitive element from said tissue overlying said artery of interest.

7. For use in a non-invasive blood pressure monitoring system, a method of estimating optimum arterial compression by measuring the stress of tissue overlying an artery of interest, said system of the type including a tissue stress sensor having a stress sensitive element, said stress sensitive element having a length that exceeds the lumen of said artery of interest, said method including the steps of:
  (A) placing said stress sensitive element of said tissue stress sensor in communication with said tissue overlying said artery of interest,
  (B) orienting said stress sensitive element such that said length spans beyond the lumen of said artery of interest,
  (C) using said stress sensitive element to varyingly compress said artery of interest thereby applanating said artery of interest through a plurality of stages, and at each said applanation stage,
  (D) obtaining from said tissue stress sensor at least one electrical signal representing stress data across the length of said stress sensitive element, said stress data including a plurality of stress datum, each stress datum representing stress communicated to a predetermined portion of said stress sensitive element from said tissue overlying said artery of interest, each said predetermined portion of said stress sensitive element lying along said length of said stress sensitive element, and for each applanation stage, using said data for,
  (E) computing a mean distribution breadth parameter and an applanation state parameter,
  (F) relating said mean distribution breadth parameter to said applanation state parameter,
  (G) determining the value of said applanation state parameter that corresponds to a mean distribution breadth parameter approximately equal to one,
  (H) estimating the optimum arterial compression to be that degree of artery applanation which produces the applanation state parameter value of step (G).

8. The method of claim 7, wherein step (E) includes computing said mean distribution breadth parameter as follows:

$$MDBP = \frac{\frac{1}{L} \int_0^L \sigma_{MCS}(x) \cdot dx}{\frac{1}{c-b} \int_b^c \sigma_{MCS}(x) \cdot dx}$$

where:
L = length of stress sensitive element
b,c = limits of integration
$\sigma_{MCS}(x)$ = mean contact stress as a function of x
x = distance along length of stress sensitive element.

9. The method of claim 8, wherein said mean contact stress is computed as follows:

$$\sigma_{MCS}(x) = \frac{\int_{t_1}^{t_1 + n\tau} \sigma(x, t) \cdot dt}{\int_{t_1}^{t_1 + n\tau} dt}$$

where:
$\tau$ = time period of one heartbeat
n = the number of heartbeats selected for time averaging.

10. The method of claim 7, wherein said applanation state parameter is computed as follows:

$$\sigma_{DCSAVG} = \frac{1}{L} \int_0^L \sigma_{DCS}(x) \cdot dx$$

where:
$\sigma_{DCSAVG}$ = average diastolic stress across the length of the stress sensitive element
L = length of stress sensitive element
$\sigma_{DCS}(x)$ = diastolic stress as a function of x
x = location along the stress sensitive element.

11. The method of claim 8, wherein said limits of integration b,c are computed by determining which portion of the stress sensitive element is in receipt of a predetermined quantity of the stress energy imparted to the stress sensitive element from said tissue overlying said artery of interest.

12. For use in a non-invasive blood pressure monitoring system, a method of estimating optimum arterial compression by measuring the stress of tissue overlying an artery of interest, said system of the type including a tissue stress sensor having a stress sensitive element, said stress sensitive element having a length that exceeds the lumen of said artery of interest, said method including the steps of:

(A) placing said stress sensitive element of said tissue stress sensor in communication with said tissue overlying said artery of interest, (B) orienting said stress sensitive element such that said length spans beyond the lumen of said artery of interest, (C) using said stress sensitive element to varyingly compress said artery of interest thereby applanating said artery of interest through a plurality of stages, and at each said applanation stage, (D) obtaining from said tissue stress sensor at least one electrical signal representing stress data across the length of said stress sensitive element, said stress data including a plurality of stress datum, each stress datum representing stress communicated to a predetermined portion of said stress sensitive element from said tissue overlying said artery of interest, each said predetermined portion of said stress sensitive element lying along said length of said stress sensitive element, and for each applanation stage, using said data for, (E) computing a diastolic distribution breadth parameter and an applanation state parameter, (F) relating said diastolic distribution breadth parameter to said applanation state parameter, (G) determining the value of said applanation state parameter that corresponds to a diastolic distribution breadth parameter value approximately equal to 1.05, (H) estimating the optimal arterial compression to be that degree of artery applanation which produces the applanation state parameter value of step (G).

13. The method of claim 12, wherein step (E) includes computing said diastolic distribution breadth parameter as follows:

$$DDBP = \frac{\frac{1}{L} \int_0^L \sigma_{DCS}(x) \cdot dx}{\frac{1}{c-b} \int_b^c \sigma_{DCS}(x) \cdot dx}$$

where:
L = length of stress sensitive element
b,c = limits of integration
$\sigma_{DCS}(x)$ = mean contact stress as a function of x
x = distance along length of stress sensitive element.

14. The method of claim 12, wherein said applanation state parameter is computed as follows:

$$\sigma_{DCSAVG} = \frac{1}{L} \int_0^L \sigma_{DCS}(x) \cdot dx$$

where:
$\sigma_{DCSAVG}$ = average diastolic stress across the length of the stress sensitive element
L = length of stress sensitive element
$\sigma_{DCS}(x)$ = diastolic stress as a function of x
x = location along the stress sensitive element.

15. The method of claim 13, wherein said limits of integration b,c are computed by determining which portion of the stress sensitive element is in receipt of a predetermined quantity of the stress energy imparted to the stress sensitive element from said tissue overlying said artery of interest.

16. For use in a non-invasive blood pressure monitoring system, a method of estimating optimum arterial compression by measuring the stress of tissue overlying an artery of interest, said system of the type including a tissue stress sensor having a stress sensitive element, said stress sensitive element having a length that exceeds the lumen of said artery of interest, said method including the steps of:

(A) placing said stress sensitive element of said tissue stress sensor in communication with said tissue overlying said artery of interest, (B) orienting said stress sensitive element such that said length spans beyond the lumen of said artery of interest, (C) using said stress sensitive element to varyingly compress said artery of interest thereby applanating said artery of interest through a plurality of stages, and at each said applanation stage, (D) obtaining from said tissue stress sensor at least one electrical signal representing stress data across the length of said stress sensitive element, said stress data including a plurality of stress datum, each stress datum representing stress communicated to a predetermined portion of said stress sensitive element from said tissue overlying said artery of interest, each said predetermined portion of said stress sensitive element lying along said length of said stress sensitive element, and for each applanation stage, using said data for, (E) computing a pulse distribution breadth parameter and an applanation state parameter, (F) relating said pulse distribution breadth parameter to said applanation state parameter, (G) determining a maximum value of said pulse distribution breadth parameter and the corresponding applanation state parameter value, (H) selecting a range of applanation state parameter values occurring at applanation stages of less applanation than the applanation state corresponding to the maximum pulse distribution breadth parameter value of step (G), (I) determining a mid-point value in the range selected in step (H), (J) determining the optimum arterial compression to be that degree of arterial applanation which produces the applanation state parameter mid-point value of step (I).

17. The method of claim 16, wherein step (E) includes computing said pulse distribution breadth parameter as follows:

$$PDBP = \int_b^c dx = W_{TH}$$

where:
$W_{TH}$ = cumulative width at $\sigma_{PCSTHR}$
$\sigma_{PCSTHR}$ = predetermined threshold value of pulsatile contact stress
b,c = limits of integration.

18. The method of claim 17, wherein two or more pulse distribution breadth parameter values are computed using respectively associated predetermined threshold values of pulsatile contact stress, wherein an overall pulse distribution breadth parameter value is derived by mathematically combining said two or more pulse distribution breadth parameter values.

19. The method of claim 16, wherein said applanation state parameter is computed as follows:

$$\sigma_{DCSAVG} = \frac{1}{L} \int_0^L \sigma_{DCS}(x) \cdot dx$$

where:

$\sigma_{DCSAVG}$ = average diastolic stress across the length of the stress sensitive element
L = length of stress sensitive element
$\sigma_{DCS}(x)$ = diastolic stress as a function of x
x = location along the stress sensitive element.

20. The method of claim 17, wherein said limits of integration b,c are computed by determining which portion of the stress sensitive element is in receipt of a predetermined quantity of the stress energy imparted to the stress sensitive element from said tissue overlying said artery of interest.

21. For use in a non-invasive blood pressure monitoring system, a method of estimating optimum arterial compression by measuring the stress of tissue overlying an artery of interest, said system of the type including a tissue stress sensor having a stress sensitive element, said stress sensitive element having a length that exceeds the lumen of said artery of interest, said method including the steps of:

(A) placing said stress sensitive element of said tissue stress sensor in communication with said tissue overlying said artery of interest,
(B) orienting said stress sensitive element such that said length spans beyond the lumen of said artery of interest,
(C) using said stress sensitive element to varyingly compress said artery of interest thereby applanating said artery of interest through a plurality of stages, and at each said applanation stage,
(D) obtaining from said tissue stress sensor at least one electrical signal representing stress data across the length of said stress sensitive element, said stress data including a plurality of stress datum, each stress datum representing stress communicated to a predetermined portion of said stress sensitive element from said tissue overlying said artery of interest, each said predetermined portion of said stress sensitive element lying along said length of said stress sensitive element, and for each applanation stage, using said data for,
(E) computing a pulse distribution breadth parameter, an applanation state parameter, and a change in pulse distribution breadth parameter with respect to the applanation state parameter,
(F) relating said change in said pulse distribution breadth parameter to said applanation state parameter,
(G) determining the value of said applanation state parameter that corresponds to a maximum value of said pulse distribution breadth parameter,
(H) estimating the optimum arterial compression to be that degree of arterial applanation which produces the applanation state parameter value of step (G).

22. The method of claim 21, wherein step (E) includes computing said pulse distribution breadth parameter as follows:

$$PDBP = \int_b^c dx = W_{TH}$$

where:
$W_{TH}$ = cumulative width at $\sigma_{PCSTHR}$
$\sigma_{PCSTHR}$ = predetermined threshold value of pulsatile contact stress
b,c limits of integration.

23. The method of claim 22, wherein step (E) includes computing said change in said pulse distribution breadth parameter as follows:

$$\Delta PDBP(i) = W_{TH}(i) - W_{TH}(i+1)$$

where:
$\Delta PDBP(i)$ = change in pulse distribution breadth parameter for the ith applanation state
$W_{TH}(i)$ = cumulative width at $\sigma_{PCSTHR}$ for the ith applanation state
$W_{TH}(i+1)$ = cumulative width at $\sigma_{PCSTHR}$ for the i+1 applanation state
i = a given applanation state.

24. The method of claim 21, wherein said applanation state parameter is computed as follows:

$$\sigma_{DCSAVG} = \frac{1}{L} \int_0^L \sigma_{DCS}(x) \cdot dx$$

where:
$\sigma_{DCSAVG}$ = average diastolic stress across the length of the stress sensitive element
L = length of stress sensitive element
$\sigma_{DCS}(x)$ = diastolic stress as a function of x
x = location along the stress sensitive element.

25. The method of claim 22, wherein said limits of integration b,c are computed by determining which portion of the stress sensitive element is in receipt of a predetermined quantity of the stress energy imparted to the stress sensitive element from said tissue overlying said artery of interest.

26. For use in a non-invasive blood pressure monitoring system, a method of estimating optimum arterial compression by measuring the stress of tissue overlying an artery of interest, said system of the type including a tissue stress sensor having a stress sensitive element, said stress sensitive element having a length that exceeds the lumen of said artery of interest, said method including the steps of:

(A) placing said stress sensitive element of said tissue stress sensor in communication with said tissue overlying said artery of interest,
(B) orienting said stress sensitive element such that said length spans beyond the lumen of said artery of interest,
(C) using said stress sensitive element to varyingly compress said artery of interest thereby applanating said artery of interest through a plurality of stages, and at each said applanation stage,
(D) obtaining from said tissue stress sensor at least one electrical signal representing stress data across the length of said stress sensitive element, said stress data including a plurality of stress datum, each stress datum representing stress communicated to a predetermined portion of said stress sensitive element from said tissue overlying said artery of interest, each said predetermined portion of said stress sensitive element lying along said length of said stress sensitive element, and for each applanation stage, using said data for, (E) computing a pulse spread parameter, an applanation state parameter, and the derivative of the pulse spread parameter with respect to the applanation state parameter, (F) relating said derivative of said pulse spread parameter to said applanation state parameter, (G) determining the value of said applanation state parameter that corresponds to a maximum value of said derivative of said pulse spread parameter, (H) estimating the optimum arterial compression to be that degree of arterial applanation which produces the applanation state parameter of step (G).

27. The method of claim 26, wherein step (E) includes computing said pulse spread parameter as follows:

$$PSP = \sigma_{PCSMAX} - \sigma_{PCSENG}$$

where:

$\sigma_{PCSENG} = \sigma_{PCSB}$ or $\sigma_{PCSc}$, which ever is the lesser
$\sigma_{PCSMAX}$ = Maximum pulsatile contact stress value for a given applanation state
$\sigma_{PCSb}$, $\sigma_{PCSc}$ = points along $\sigma_{PCS}(x)$ which intersect region bounded by b,c.

28. The method of claim 26, wherein said applanation state parameter is computed as follows:

$$\sigma_{DCSAVG} = \frac{1}{L} \int_0^L \sigma_{DCS}(x) \cdot dx$$

where:

$\sigma_{DCSAVG}$ = average diastolic stress across the length of the stress sensitive element
L = length of stress sensitive element
$\sigma_{DCS}(x)$ = diastolic stress as a function of x
x = location along the stress sensitive element.

29. The method of claim 27, wherein said limits of integration b,c are computed by determining which portion of the stress sensitive element is in receipt of a predetermined quantity of the stress energy imparted to the stress sensitive element from said tissue overlying said artery of interest.

30. For use in a non-invasive blood pressure monitoring system, a method of estimating optimum arterial compression by measuring the stress of tissue overlying an artery of interest, said system of the type including a tissue stress sensor having a stress sensitive element, said stress sensitive element having a length that exceeds the lumen of said artery of interest, said method including the steps of:

(A) placing said stress sensitive element of said tissue stress sensor in communication with said tissue overlying said artery of interest, (B) orienting said stress sensitive element such that said length spans beyond the lumen of said artery of interest, (C) using said stress sensitive element to varyingly compress said artery of interest thereby applanating said artery of interest through a plurality of stages, and at each said applanation stage, (D) obtaining from said tissue stress sensor at least one electrical signal representing stress data across the length of said stress sensitive element, said stress data including a plurality of stress datum, each stress datum representing stress communicated to a predetermined portion of said stress sensitive element from said tissue overlying said artery of interest, each said predetermined portion of said stress sensitive element lying along said length of said stress sensitive element, and for each applanation stage, using said data for, (E) computing a pulse distribution breadth parameter, an applanation state parameter, and a derivative of said pulse distribution breadth parameter with respect to said applanation state parameter, (F) relating said derivative of said pulse distribution breadth parameter to said applanation state parameter, (G) determining the value of said applanation state parameter that corresponds to a maximum value of said derivative of said pulse distribution breadth parameter, (H) estimating the optimum arterial compression to be that degree of arterial applanation which produces the applanation state parameter value of step (G).

31. The method of claim 30, wherein step (E) includes computing said pulse spread parameter as follows:

$$PDBP = \int_b^c dx = W_{TH}$$

where:

$W_{TH}$ = cumulative width at threshold $\sigma_{PCSTHR}$ along normalized plot of pulsatile contact stress $\sigma_{PCSNOR}(x)$
b,c = limits of integration defined by 60 percent of $\sigma_{PCSMAX}$.

32. The method of claim 30, wherein said applanation state parameter is computed as follows:

$$\sigma_{DCSAVG} = \frac{1}{L} \int_0^L \sigma_{DCS}(x) \cdot dx$$

where:

$\sigma_{DCSAVG}$ = average diastolic stress across the length of the stress sensitive element
L = length of stress sensitive element
$\sigma_{DCS}(x)$ = diastolic stress as a function of x
x = location along the stress sensitive element.

33. For use in a non-invasive blood pressure monitoring system, a method of estimating optimum arterial compression by measuring the stress of tissue overlying an artery of interest, said system of the type including a tissue stress sensor having a stress sensitive element, said stress sensitive element having a length that exceeds the lumen of said artery of interest, said method including the steps of:

(A) placing said stress sensitive element of said tissue stress sensor in communication with said tissue overlying said artery of interest, (B) orienting said stress sensitive element such that said length spans beyond the lumen of said artery of interest, (C) using said stress sensitive element to varyingly compress said artery of interest thereby applanating said artery of interest through a plurality of stages, and at each said applanation stage, (D) obtaining from said tissue stress sensor at least one electrical signal representing stress data across the length of said stress sensitive element, said stress data including a plurality of stress datum, each stress datum representing stress communicated to a predetermined portion of said stress sensitive element from said tissue overlying said artery of interest, each said predetermined portion of said stress sensitive element lying along said length of said stress sensitive element, and for each applanation stage, using said data for, (E) computing a diastolic distribution breadth parameter, an applanation state parameter, and a derivative of said diastolic distribution breadth parameter with respect to the applanation state parameter, (F) relating a derivative of the diastolic distribution breadth parameter to the applanation state parameter, (G) determining the value of said applanation state parameter that corresponds to a maximum of said derivative of said diastolic distribution breadth parameter, (H) estimating the optimum arterial compression to be that degree of artery applanation which produces the applanation state parameter value of step (G).

34. The method of claim 33, wherein step (E) includes computing said diastolic distribution breadth parameter as follows:

$$DDBP = \frac{\frac{1}{L}\int_0^L \sigma_{DCS}(x) \cdot dx}{\frac{1}{c-b}\int_b^c \sigma_{DCS}(x) \cdot dx}$$

where:
L = length of stress sensitive element
b,c = limits of integration
$\sigma_{DCS}(x)$ = mean contact stress as a function of x
x = distance along length of stress sensitive element.

35. The method of claim 33, wherein said applanation state parameter is computed as follows:

$$\sigma_{DCSAVG} = \frac{1}{L}\int_0^L \sigma_{DCS}(x) \cdot dx$$

where:
$\sigma_{DCSAVG}$ = average diastolic stress across the length of the stress sensitive element
L = length of stress sensitive element
$\sigma_{DCS}(x)$ = diastolic stress as a function of x
x = location along the stress sensitive element.

36. The method of claim 34, wherein said limits of integration b,c are computed by determining which portion of the stress sensitive element is in receipt of a predetermined quantity of the stress energy imparted to the stress sensitive element from said tissue overlying said artery of interest.

37. For use in a non-invasive blood pressure monitoring system, a method of estimating optimum arterial compression by measuring the stress of tissue overlying an artery of interest, said system of the type including a tissue stress sensor having a stress sensitive element, said stress sensitive element having a length that exceeds the lumen of said artery of interest, said method including the steps of:

(A) placing said stress sensitive element of said tissue stress sensor in communication with said tissue overlying said artery of interest, (B) orienting said stress sensitive element such that said length spans beyond the lumen of said artery of interest, (C) using said stress sensitive element to varyingly compress said artery of interest thereby applanating said artery of interest through a plurality of stages, and at each said applanation stage, (D) obtaining from said tissue stress sensor at least one electrical signal representing stress data across the length of said stress sensitive element, said stress data including a plurality of stress datum, each stress datum representing stress communicated to a predetermined portion of said stress sensitive element from said tissue overlying said artery of interest, each said predetermined portion of said stress sensitive element lying along said length of said stress sensitive element, and for each applanation stage, using said data for, (E) computing a spatially averaged stress parameter, an applanation state parameter, and a second derivative of said spatially averaged stress parameter with respect to the applanation state parameter, (F) relating the second derivative of the spatially averaged stress parameter to the applanation state parameter, (G) determining the value of said applanation state parameter that corresponds to a minimum value of said second derivative of said spatially averaged stress parameter, (H) estimating the optimum arterial compression to be that degree of artery applanation which produces the applanation state parameter value of step (G).

38. The method of claim 37, wherein step (E) includes computing said spatially averaged stress parameter as follows:

$$SASP = \frac{1}{c-b}\int_b^c \sigma(x) \cdot dx$$

where:
b,c = limits of integration
x = distance along the stress sensitive diaphragm
$\sigma(x)$ = stress sensed along stress sensitive element as a function of x.

39. The method of claim 38, wherein $\sigma(x)$ is selected from the group of $\sigma_{DCS}(x)$, $\sigma_{SCS}(x)$, $\sigma_{MCS}(x)$, and $\sigma_{PCS}(x)$ where:
$\sigma_{DCS}(x)$ = diastolic contact stress as a function of x,
$\sigma_{SCS}(x)$ = systolic contact stress as a function of x,
$\sigma_{MCS}(x)$ = mean contact stress as a function of x,
$\sigma_{PCS}(x)$ = pulsatile contact stress as a function of x.

40. The method of claim 38, wherein $\sigma(x)$ is selected from the group of $F(\sigma_{DCS}(x))$, $F(\sigma_{SCS}(x))$, $F(\sigma_{MCS}(x))$, and $F(\sigma_{PCS}(x))$ where:
$F(\sigma_{DCS}(x))$ = weighted function of diastolic contact stress,
$F(\sigma_{SCS}(x))$ = weighted function of systolic contact stress,
$F(\sigma_{MCS}(x))$ = weighted function of mean contact stress,
$F(\sigma_{PCS}(x))$ = weighted function of pulsatile contact stress.

41. The method of claim 37, wherein said applanation state parameter is computed as follows:

$$\sigma_{DCSAVG} = \frac{1}{L} \int_0^L \sigma_{DCS}(x) \cdot dx$$

where:
$\sigma_{DCSAVG}$ = average diastolic stress across the length of the stress sensitive element
L = length of stress sensitive element
$\sigma_{DCS}(x)$ = diastolic stress as a function of x
x = location along the stress sensitive element.

42. The method of claim 38, wherein said limits of integration b,c are computed by determining which portion of the stress sensitive element is in receipt of a predetermined quantity of the stress energy imparted to the stress sensitive element from said tissue overlying said artery of interest.

43. For use in a non-invasive blood pressure monitoring system, a method of estimating optimum arterial compression by measuring the stress of tissue overlying an artery of interest, said system of the type including a tissue stress sensor having a stress sensitive element, said stress sensitive element having a length that exceeds the lumen of said artery of interest, said method including the steps of:

(A) placing said stress sensitive element of said tissue stress sensor in communication with said tissue overlying said artery of interest, (B) orienting said stress sensitive element such that said length spans beyond the lumen of said artery of interest, (C) using said stress sensitive element to varyingly compress said artery of interest thereby applanating said artery of interest through a plurality of stages, and at each said applanation stage, (D) obtaining from said tissue stress sensor at least one electrical signal representing stress data across the length of said stress sensitive element, said stress data including a plurality of stress datum, each stress datum representing stress communicated to a predetermined portion of said stress sensitive element from said tissue overlying said artery of interest, each said predetermined portion of said stress sensitive element lying along said length of said stress sensitive element, and for each applanation stage, using said data for, (E) computing a stress spatial curvature parameter, an applanation state parameter, and a derivative of said stress spatial curvature parameter with respect to the applanation state parameter, (F) relating the derivative of the stress spatial curvature parameter to the applanation state parameter, (G) determining a maximum of said derivative of said stress spatial curvature parameter, (H) estimating the optimum arterial compression to be that degree of artery applanation which produces the applanation state parameter value of step (G).

44. The method of claim 43, wherein step (E) includes computing said stress spatial curvature parameter as follows: where:

$$SSCP = \frac{\partial^2 \sigma(x)}{\partial x^2} \bigg|_{x=\bar{x}}$$

-continued $\frac{\partial^2}{\partial x^2}$ = second derivative with respect to x $\bar{x}$ = center of pulsatily active region of stress sensitive element
x = distance along length of stress sensitive element
$\sigma(x)$ = stress sensed along stress sensitive element as a function of x.

45. The method of claim 44, wherein $\sigma(x)$ is selected from the group of $\sigma_{DCS}(x)$, $\sigma_{SCS}(x)$, $\sigma_{MCS}(x)$, and $\sigma_{PCS}(x)$ where:
$\sigma_{DCS}(x)$ = diastolic contact stress as a function of x,
$\sigma_{SCS}(x)$ = systolic contact stress as a function of x,
$\sigma_{MCS}(x)$ = mean contact stress as a function of x,
$\sigma_{PCS}(x)$ = pulsatile contact stress as a function of x.

46. The method of claim 44, wherein $\sigma(x)$ is selected from the groups of $F(\sigma_{DCS}(x))$, $F(\sigma_{SCS}(x))$, $F(\sigma_{MCS}(x))$, and $F(\sigma_{PCS}(x))$ where:
$F(\sigma_{DCS}(x))$ = weighted function of diastolic contact stress,
$F(\sigma_{SCS}(x))$ = weighted function of systolic contact stress,
$F(\sigma_{MCS}(x))$ = weighted function of mean contact stress,
$F(\sigma_{PCS}(x))$ = weighted function of pulsatile contact stress.

47. The method of claim 44, wherein step (E) includes computing $\bar{x}$ as follows:

$$\bar{x} = \frac{\int_b^c (x \cdot \sigma(x)) \cdot dx}{\int_b^c \sigma(x) \cdot dx}$$

where:
b,c = limits of integration
x = distance along the stress sensitive diaphragm
$\sigma(x)$ = stress sensed along stress sensitive element as a function of x.

48. The method of claim 47, wherein said limits of integration b,c are computed by determining which portion of the stress sensitive element is in receipt of a predetermined quantity of the stress energy imparted to the stress sensitive element from said tissue overlying said artery of interest.

49. The method of claim 43, wherein said applanation state parameter is computed as follows:

$$\sigma_{DCSAVG} = \frac{1}{L} \int_0^L \sigma_{DCS}(x) \cdot dx$$

where:
$\sigma_{DCSAVG}$ = average diastolic stress across the length of the stress sensitive element
L = length of stress sensitive element
$\sigma_{DCS}(x)$ = diastolic stress as a function of x
x = location along the stress sensitive element.

50. For use in a non-invasive blood pressure monitoring system, a method of estimating optimum arterial compression by measuring the stress of tissue overlying an artery of interest, said system of the type including a tissue stress sensor having a stress sensitive element, said stress sensitive element having a length that exceeds the lumen of said artery of interest, said method including the steps of:

(A) placing said stress sensitive element of said tissue stress sensor in communication with said tissue overlying said artery of interest, (B) orienting said stress sensitive element such that said length spans beyond the lumen of said artery of interest, (C) using said stress sensitive element to varyingly compress said artery of interest thereby applanating said artery of interest through a plurality of stages, and at each said applanation stage, (D) obtaining from said tissue stress sensor at least one electrical signal representing stress data across the length of said stress sensitive element, said stress data including a plurality of stress datum, each stress datum representing stress communicated to a predetermined portion of said stress sensitive element from said tissue overlying said artery of interest, each said predetermined portion of said stress sensitive element lying along said length of said stress sensitive element, and for each applanation stage, using said data for, (E) computing a stress variation parameter, an applanation state parameter, and a derivative of said stress variation parameter with respect to the applanation state parameter, (F) relating the derivative of the stress variation parameter to the applanation state parameter, (G) determining a minimum of said derivative stress variation parameter, (H) estimating the optimum arterial compression to be that degree of artery applanation which produces the applanation state parameter value of step (G).

51. The method of claim 50, wherein step (E) includes computing said stress variation parameter as follows:

$$SVPAR = \sigma_{MAX} - \sigma_{MIN}$$

where:

$\sigma_{MAX}$=maximum stress occurring along $\sigma(x)$ in region of stress sensitive element receiving highest pulse energy $\sigma_{MIN}$=minimum stress occurring along $\sigma(x)$ in region of stress sensitive element receiving highest pulse energy x=distance along length of stress sensitive element $\sigma(x)$=stress sensed along stress sensitive element as a function of x.

52. The method of claim 51, wherein $\sigma(x)$ is selected from the groups of $\sigma_{DCS}(x)$, $\sigma_{SCS}(x)$, $\sigma_{MCS}(x)$, and $\sigma_{PCS}(x)$ where:

$\sigma_{DCS}(x)$=diastolic contact stress as a function of x,
$\sigma_{SCS}(x)$=systolic contact stress as a function of x,
$\sigma_{MCS}(x)$=mean contact stress as a function of x,
$\sigma_{PCS}(x)$=pulsatile contact stress as a function of x.

53. The method of claim 50, wherein step (E) includes computing said stress variation parameter as follows:

$$SVPAR = SD(\sigma(x))$$

where:

SD=standard deviation operation
$\sigma(x)$=contact stress occurring in region of stress sensitive element receiving highest pulse energy
x=distance along length of stress sensitive element.

54. The method of claim 53, wherein $\sigma(x)$ is selected from the groups of $\sigma_{DCS}(x)$, $\sigma_{SCS}(x)$, $\sigma_{MCS}(x)$, and $\sigma_{PCS}(x)$ where:

$\sigma_{DCS}(x)$=diastolic contact stress as a function of x,
$\sigma_{SCS}(x)$=systolic contact stress as a function of x,
$\sigma_{MCS}(x)$=mean contact stress as a function of x,
$\sigma_{PCS}(x)$=pulsatile contact stress as a function of x.

55. The method of claim 51, wherein said region of said stress sensitive element receiving the highest pulse energy is defined by bounding limits b,c, and wherein bounding limits b,c are computed by determining which portion of the stress sensitive element is in receipt of a predetermined quantity of the stress energy imparted to the stress sensitive element from said tissue overlying said artery of interest.

56. The method of claim 50, wherein said applanation state parameter is computed as follows:

$$\sigma_{DCSAVG} = \frac{1}{L} \int_0^L \sigma_{DCS}(x) \cdot dx$$

where:

$\sigma_{DCSAVG}$=average diastolic stress across the length of the stress sensitive element
L=length of stress sensitive element
$\sigma_{DCS}(x)$=diastolic stress as a function of x
x=location along the stress sensitive element.

57. For use in a non-invasive blood pressure monitoring system, a method of estimating optimum arterial compression by measuring the stress of tissue overlying an artery of interest, said system of the type including a tissue stress sensor having a stress sensitive element, said stress sensitive element having a length that exceeds the lumen of said artery of interest, said method including the steps of:

(A) placing said stress sensitive element of said tissue stress sensor in communication with said tissue overlying said artery of interest, (B) orienting said stress sensitive element such that said length spans beyond the lumen of said artery of interest, (C) using said stress sensitive element to varyingly compress said artery of interest thereby applanating said artery of interest through a plurality of stages, and at each said applanation stage, (D) obtaining from said tissue stress sensor at least one electrical signal representing stress data across the length of said stress sensitive element, said stress data including a plurality of stress datum, each stress datum representing stress communicated to a predetermined portion of said stress sensitive element from said tissue overlying said artery of interest, each said predetermined portion of said stress sensitive element lying along said length of said stress sensitive element, and for each applanation stage, using said data for, (E) selecting and computing an applanation optimization parameter, wherein said applanation optimization parameters is selected from the group of parameters comprising pulse parameter, distribution breadth parameter, pulse spread parameter, spatially averaged stress parameter, stress spatial curvature parameter, stress variation parameter, (F) selecting and computing an applanation state parameter, (G) relating the selected applanation optimization parameter to the applanation state parameter, (H) determining a value associated with a characteristic feature of said selected applanation optimization parameter, with respect to said artery applanation state parameter, said characteristic feature being indicative of said optimum arterial compression, (I) estimating the optimum arterial compression to be that degree of artery applanation which produces the applanation optimization parameter value of step (G).

58. The method of claim 57, wherein step (F) includes selecting two or more applanation optimization parameters from the group comprising pulse parameter, mean distribution breadth parameter, pulse spread parameter, spatially averaged stress parameter, stress spatial curvature parameter, and stress variation parameter, and wherein step (G) includes relating said two or more applanation optimization parameters to a respectively associated applanation state parameter, and wherein step (H) includes for each selected applanation optimization parameter determining a value associated with a characteristic feature of said applanation optimization parameter, and wherein step (I) includes estimating the optimum arterial compression to be that degree of artery compression which produces an applanation optimization parameter value equal to a composite value of values associated with said two or more selected applanation optimization parameters.

59. The method of claim 58, wherein said composite value of said values associated with said two or more selected applanation optimization parameters is calculated as follows:

$$AOPCOM_{OPT} = \frac{\Sigma_i F[i] \cdot [AOP_{OPT}(i)]}{\Sigma_i F[i]}, (i = 1\text{-}11)$$

where:

AOPCOMOPT = composite value of optimum applanation estimate

AOPOPT(i) = the value of the applanation optimization parameter associated with the ith Method of estimating optimum arterial compression i = 1-11

F[i] = a predetermined weighting function as applied to $AOP_{OPT}(i)$.

* * * * *

UNITED STATES PATENT AND TRADEMARK OFFICE
CERTIFICATE OF CORRECTION

PATENT NO. : 5,273,046
DATED : December 28, 1993
INVENTOR(S) : Butterfield et al It is certified that error appears in the above-identified patent and that said Letters Patent is hereby corrected as shown below:

Column 55, "PCSB" should read --"PCSb"--.

Signed and Sealed this

Twenty-eighth Day of June, 1994

Attest:

BRUCE LEHMAN

Attesting Officer    Commissioner of Patents and Trademarks